US011858967B2

(12) United States Patent
Zabriskie et al.

(10) Patent No.: US 11,858,967 B2
(45) **Date of Patent: *Jan. 2, 2024**

(54) COMPOSITIONS AND METHODS FOR ENHANCED PRODUCTION OF ENDURACIDIN IN A GENETICALLY ENGINEERED STRAIN OF STREPTOMYCES FUNGICIDICUS

(71) Applicant: Oregon State University, Corvallis, OR (US)

(72) Inventors: T. Mark Zabriskie, Corvallis, OR (US); Xihou Yin, Corvallis, OR (US)

(73) Assignee: OREGON STATE UNIVERSITY, Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,413

(22) Filed: Aug. 4, 2022

(65) Prior Publication Data

US 2023/0120672 A1 Apr. 20, 2023

Related U.S. Application Data

(62) Division of application No. 16/465,444, filed as application No. PCT/US2017/064328 on Dec. 1, 2017, now Pat. No. 11,447,530.

(60) Provisional application No. 62/479,087, filed on Mar. 30, 2017, provisional application No. 62/430,838, filed on Dec. 6, 2016.

(51) Int. Cl.

*C07K 14/36* (2006.01)
*C12P 21/02* (2006.01)
*C12N 15/76* (2006.01)
*C12N 1/20* (2006.01)
*C12N 15/71* (2006.01)
*C12R 1/465* (2006.01)

(52) U.S. Cl.

CPC .............. *C07K 14/36* (2013.01); *C12N 15/71* (2013.01); *C12P 21/02* (2013.01); *C12N 1/205* (2021.05); *C12R 2001/465* (2021.05)

(58) Field of Classification Search

CPC ........ C12N 15/76; C12N 1/205; C07K 14/36; C12P 21/02; C12R 1/465

See application file for complete search history.

(56) References Cited

U.S. PATENT DOCUMENTS 3,786,142 A 1/1974 Shibata et al.
4,465,771 A 8/1984 Nogami et al.

FOREIGN PATENT DOCUMENTS

CN 104131054 A 11/2014
CN 103374537 B 1/2015
CN 105039382 A 11/2015
WO 2008054945 A2 5/2008
WO 2018103905 A1 6/2018

OTHER PUBLICATIONS

Orlova, T.I. et al., Biologically Active Nonribosomal Peptides. I. Nonribosamal Polypeptide Antibiotics; Antibiot Khimioter. 2011;56(3-4):57-68, Russian Langugae.

Yin, X et al., "The Enduracidin Biosynthetic Gene Cluster from Streptomyces Fungicidicus"; Microbiology (2006); vol. 152, pp. 2969-2983.

Baltz, R. H. "Genetic Manipulation of Secondary Metabolite Biosynthesis for Improved Production in Streptomyces and other Actinomycetes"; J. Ind. Microbiol Biotechnol (2016); vol. 43, pp. 343-370.

Yin, X. et al., "Enduracidin Analogues with Altered Halogenation Patterns Produced by Genetically Engnerred Strains of Streptomyces Fungicidicus"; J. Nat. Prod. (2010); vol. 73; pp. 583-589.

Ostash, B. et al., "Identification and characterization of the Streptomyces globisporus 1912 regulatory gene IndYR that affects sporulation and antibiotic production"; Micobiology (2011); vol. 157; pp. 1240-1249.

Yuan, T. et al., Improvement of Antibiotic Productutive by Knock-Out of dauW in Streptomyces Coeruleobidus; Microbiology Research (2011); vol. 166; pp. 539-547.

Yepes, A. et al., "Novel Two-Component Systems Implied in Antibiotic Production in Streptomyces Coelicolor"; PLoSOne (2011); vol. 6:5; 10 pgs.

Kim, S. et al., "Transcriptome Analysis of an Antibiotic Downregulator Mutant and Synergistic Actinorhodin Stimulation via Disruption of a Precursor Flux Regulator in Streptomyces Coelicolor"; Applied and Environmental Microbiology (2011); vol. 77:5; pp. 1872-1877.

*Primary Examiner* — Maryam Monshipouri
(74) *Attorney, Agent, or Firm* — Fox Rothschild LLP

(57) ABSTRACT

This disclosure describes compositions and methods for enhanced production of enduracidin in genetically engineered strains of *Streptomyces fungicidicus*. In particular, the present disclosure describes the genetic manipulation of regulatory genes orf24 and orf18 associated with the enduracidin (enramycin) biosynthesis gene cluster from *Streptomyces fungicidicus* to generate vector constructs and recombinant strains producing greater yields of enduracidin.

21 Claims, 12 Drawing Sheets

Specification includes a Sequence Listing.

| Score | Expect | Method | Identities | Positives | Gaps |
|---|---|---|---|---|---|
| 281 bits(720) | 3e-97 | Compositional matrix adjust. | 167/311(54%) | 212/311(68%) | 8/311(2%) |

```
StrR   16   IELSRLSSASSPRTSGEDPEHVETLLSAEGELPPILVHRPTMQVLDGLHRLKVARVRGDT  75
            +E+S LS+  SPR  GE PEHVE L +A+  LPPI+VHR T +V+DG+HRL+ A + G T
Orf24  1    VEISSLSTDGSPRIDGESPEHVEMLAAADTALPPIMVHRRTGRVIDGMHRLRAAMLTGRT  60

StrR   76   KILARLVDATESDAFVLAVEANIRHGLPLSLADRKRAAVQIIGTHPQWSDRRVASATGIS  135
             I  R  D TE DAFVLAV++NI HGLPLS ADR+RAA +I+ THP+WSDR +AS  G S
Orf24  61   TIAVRFFDGTEEDAFVLAVKSNIAHGLPLSAADRRRAAGRIMATHPRWSDRMIASVVGTS  120

StrR   136  AGTVADLRRRAGEDGT--EARIGRDGRVRPSDGSERRRLAAELIRSDPGLSLRQVAKQVG  193
            A TVA++RR AG  G     RIGRDGRVRP D SE RRLA ++I  DPGLSLRQVA+  G
Orf24  121  ARTVAEIRRDAGAAGAGEPTRIGRDGRVRPVDVSEGRRLAHDMIVRDPGLSLRQVARAAG  180

StrR   194  ISPETVRDVRGRLERGESPTPDGTRRLPAKPHPLRLSEPDFGRA------VDQDRLALLER  248
            ISPETVRDVR R+ RGE P P    R   +    R +EP  G+A      +      +++R
Orf24  181  ISPETVRDVRHRMLRGEDPVPAPRPRTLVERGADRRAEP-AGKAAAPCGTEPPPAVVMKR  239

StrR   249  LKSDPALRLNEVGRILLRMLTMHSMDGQEWERILQGVPPHLHGVIAGFARDHARVWAEFA  308
            L++DPALRLNE GR LLR+L +H++   ++W RI++ VPPH    +A  AR  A  W+E A
Orf24  240  LRADPALRLNENGRDLLRLLDIHTVRLEDWNRIIESVPPHRLETVAQLARSCADKWSEIA  299

StrR   309  DHLESPATELA  319
              +ES A+ LA
Orf24  300  SRIESNASHLA  310
```

Fig. 9

```
Bbr      MDPTR-------VDIFALPA-------------VEIELSRLSSASSPRT
KasT     MAETVRAIGSFLKSSIRRVPAAEVQGSGLSVGQKTTRIAISSLLAADSPRS
NovG     MTNSG-------DEBIT-P------ASLKATRKGERVSIGSLLPPSELVR
SgcR1    MKSDS-------AQRAVER-------------SRRVVRIDELIPADSPRL
StrR     MDPTR-------VDIFALPA-------------VEIELSRLSSASSPRT
Tei15*   MTPDE-------EALNRQPI-------------MEMEISSLSLGGSPRL
Orf24    ---------------------------------VEISSLSTDGSPRI
                                          : :. *    ..

Bbr      SGEDPEHVETLLSAEGELPPILVHRPTMQVLDGLHRLKVAEVEGDTKILA
KasT     AGENAEHIRLLADSGARLPPIVVQRSTMRVIDGMHRLRAAALRGRTEIEV
NovG     SGESTEHIRVLAETDEDLPPIVVHRGTRRVVDGMHRLWAAARFRGDESIEV
SgcR1    NSIDRSHVQRLATVYASLPPVLVHRPTMRVVDGMHRISAAELKGLDTVEV
StrR     SGEDPEHVETLLSAEGELPPILVHRPTMQVLDGLHRLKVAEVEGDTKILA
Tei15*   AGGDPVHLEAMVAAQGELPPIVVHRPTMRVIDGSHRIQAALRRGETTIAG
Orf24    DGESPEHVEMLAAADTALPPIMVHRRTGRVIDGMHRLRAAMLTGRTTIAV
          *.  *:. :       ***::*:* * :*:** **: .*   *   :

Bbr      RLVDATESDAFVLAVEANIRHGLPLSLADRKRAAVQIIGTHPQWSDRPVA
KasT     RFFDGAEEDSFLLAVRSNIAHGLPLSQEEPAAAAQRIIRSHAQWSNQAIG
NovG     VFVDGSPADVFVLAVELNRAHGLPLTLDERRSAAAQIMDSHPHWSDRKIA
SgcR1    TFFEGAEEQVFLRSVAANITNGLPLSVADRKTAAARILASHPTLSDRAVA
StrR     RLVDATESDAFVLAVEANIRHGLPLSLADRKRAAVQIIGTHPQWSDRPVA

Tei15*   RFFDGSDDEAFVMSVWLNVSHGLPLALADRKRAAERIAVSHPQWSDRRVA
Orf24    RFFDRTEEDAFVLAVESNIAHGLPLSAADRRAAGRIMATHPRWSDRMIA
          :.:.:  : *: :*   *  :****:  :*  ** :*  :*.  *:: :.

Bbr      SATGISAGTVADLRRRA-GEDG-TEARIGRDGRVRPSDGSERRRLAAELI
KasT     EVTGLDAKTIAALERDAKDV-PQLDARIGRDGRVRPVDSAQGRRLAGELM
NovG     RITGLAASTVASLRSSST-AG-TVGRRTGQDGRSRPNDGTDGRQRAAALL
SgcR1    AHVGLDAKTVAGVRTCSAAGGPLLNMETGADGRVHPLDETAEPLHAAALL
StrR     SATGISAGTVADLRRRA-GEDG-TEARIGRDGRVRPSDGSERRRLAAELI
Tei15*   AVTGISPSTVADIRRRVAGTSAPEAGRIGQDGRVRPLDCSAGRLLAGRLM
Orf24    SVVGTSARTVAEIRRDAGAAGAGEPTRIGRDGRVRPVDVSEGRRLAHDMI
          .*   . *:* :*              * * *** :* * :  *  *  ::

Bbr      RSDPGLSLAQVAKQVGISPETVRDVRGRLERGESPTPDGTRRLP-AKPH-
KasT     AEQPDAPLRKIAHRAGVSLGTASDVRRRIRNGQDPVPAGRQKAD-PQPP-
NovG     ARNPNASLREVTRAAGISVGTASDVRARLRRGEPALTARQQAVMKLRPA-
SgcR1    TQDPGLPLRSVVRQTGLSLGTAHDVRRRLLRGEDPVPQNRQSAM-LEPGL
StrR     RSDPGLSLAQVAKQVGISPETVRDVRGRLERGESPTPDGTRRLP-AKPH-
Tei15*   AENPALGLRQVAKAAAISPETAEDVRRRLLGGAELVPNRRPRDA-A-PV-
Orf24    VRDPGLSLRQVARAAGISPETVRDVRRRMLRGEDPVPAPRPRTL-VERG-
          :*    .**.:.. ..:*  *. *** *:  *        .
            Helix-Turn-Helix motif

Bbr      -PL--RLSEP-----DPGRA--------------------V--DQDRLALLERL
KasT     -AR-YAASED----R-SGTTA-----------PR--TG--EQNRRVLLQKL
NovG     -RA--QRSGP------------------------------DYGRVLENL
SgcR1    APQKKATAKP----PVGPAARPVPKVPPAVAGRPPVSPRSPAPLEALRKL
StrR     -PL--RLSEP-----DPGRA--------------------V--DQDRLALLERL
Tei15*   -GV--KGGRDRRPLNLIPSGD-----------RP--EP-VPDHAVVINRL
Orf24    -AD--RRAEP-----A-GKAAA-----------PC--GT--EPPPAVVMKRL
             .                                            :..*

Bbr      DHARVWAEPADHLESPATEL-------------AAG
KasT     GCSGVWQDFAAQLERRG--R-------------ASA
NovG     ECAAAWQRLAIQLADED----------------TA
SgcR1    HCSDAWHRFAEEMVRRRSAAADGGGLRTTQPTRR
StrR     DHARVWAEPADRLESRATEL-------------AAG
Tei15*   QFADLWADFASPVGPEE--R-------------MAS
Orf24    SCADKWSEIASKIESNAS-H-------------LAS
          :  *  :*. .:   .
```

Fig. 11

```
SCO1745/AbrA2   MT-----------------IPLLIVDDQELIRTGFRLFLQTQNDLEVVGE
SCO3226/AbsA2   M------------------IRVLLADDETIIRAGVRSILTTEPGIEVVAE
SCO3818         MRE-------------DGKIRVFLLDDHEVVERGVHDLLSGEADIEVVGE
Orf18           VSVLLSQFASLVAYRPRKPTAMVVV-ADPRVRSTVTRHLWA-LGVRDVIE
                :                    :.:   .  :*  .     *    .:.  * *

SCO1745/AbrA2   ADNGHGALAQAAALRPDVVLMDIRMPRMDGVEATSRLTASDSPRRVLILT
SCO3226/AbsA2   ASDGREAVELAERHRPDVALLDIRMPEMDGLTAAGEMRTTNPDTAVVVLT
SCO3818         ACTAAEAQARVTATRPDVAVLDVRLPDGSGVEVCRDIRSEDESVRCLMLT
Orf18           ASSVAEARPRIGNPR-DICVAEVHLPDGSGLTLLSETPAAGW-ENGLALS
                *     .        * *: : ::::*  .*:                : *:

SCO1745/AbrA2   TFDLDEYVFGALRAGASGFLLKDAPRDRLLEAIRVVHAGEALLSPSITRR
SCO3226/AbsA2   TFGEDRYIERALDQGVAGFLLKASDPRDLISGVRAVASGGSCLSFLVARR
SCO3818         SFADDEALFDAIMAGASSYVLKDIRGAELLSAVREVAAGKSLLDPAATAR
Orf18           AADDIGAVRRALAGGVRGYVVTGTRTNLGL-PTRPGAA---PI-GAAAAR
                :       :  *:  *. *:::.          :   *   :     :   : *

SCO1745/AbrA2   LIEDYATRAAPV-RPR--EAVLAGLTPREREILLLVARGLSNPEIAARLV
SCO3226/AbsA2   LMTELR--RAPGPRSEVSGERTTLLTRREQEVLSMLGAGLSNAEIAQRLH
SCO3818         VLERLR--GGGA---RP-DDRLAPLTEQERRILELIGEGLTNRAIGERLH
Orf18           LHRRPP---GAPS----HPG-G-YRELSGPEVEVLELVAEGQSNKAIGVSMG
                :         .                *. :* .:    :. * :*  *.   :

SCO1745/AbrA2   VTEATVKSHVGSMFAKLSLRDRAQAVVFAYENAIVLP-GGTG
SCO3226/AbsA2   LVEGTIKTYVSAIFTQLEVRNRVQAAIIAYEAGLVKDADLNR
SCO3818         LAEKTIKNYVSSLLGKLGMQRRSQAAAFVAR----LE-AENR
Orf18           LSALTVKSHLARIAFKLGTGDRAGMVAVALRTGII------R
                :   *:* ::. :  :*    *    . ..
```

Fig. 12

COMPOSITIONS AND METHODS FOR ENHANCED PRODUCTION OF ENDURACIDIN IN A GENETICALLY ENGINEERED STRAIN OF STREPTOMYCES FUNGICIDICUS

CROSS-REFERENCE TO RELATED APPLICATIONS

This application is a divisional of U.S. application Ser. No. 16/465,444, filed May 30, 2019, now U.S. Pat. No. 11,447,530, issued Sep. 20, 2022, which is a 371 of PCT/US17/64328, filed Dec. 1, 2017, which claims the benefit of priority of the early filing date of U.S. Provisional Patent Nos. 62/430,838, filed Dec. 6, 2016 and 62/479,087, filed Mar. 30, 2017, each of which is hereby incorporated herein by reference in its entirety.

REFERENCE TO A SEQUENCE LISTING

This application incorporates by reference the Sequence Listing submitted in Computer Readable Form as an xml named Seq Listing 05283800116 Dec-12-2022.xml, created on Dec. 12, 2022 and containing 184,154 bytes.

FIELD

This disclosure relates to antibiotic biosynthesis, in particular, to the compositions and methods for enhanced production of enduracidin.

BACKGROUND

The global emergence of multidrug-resistant bacterial infections has resulted in enormous healthcare costs and has become a major threat to public health. To stay ahead of the development of antibacterial drug resistances, there is a need to identify new antibiotics as well as methods of producing such antibiotics in a more cost-efficient manner.

SUMMARY

The present disclosure overcomes problems associated with limited production of enduracidin (enramycin) in wild type strains of *Streptomyces fungicidicus*, as well as production limits in industrial strains developed through conventional radiation and chemical-mediated mutagenesis of the chromosome and successive multiple rounds of selection of mutants for production of increased levels of the desired enduracidin peptide antibiotics. Disclosed herein is the genetic manipulation of regulatory genes orf24 and orf18 associated with the enduracidin (enramycin) biosynthesis gene cluster from *Streptomyces fungicidicus* to generate recombinant vectors and strains producing greater yields of this peptide antibiotic. Recombinant strains were constructed in both the wild-type producer, *Streptomyces fungicidicus* B-5477 (ATCC 21013), and *Streptomyces fungicidicus* BM38-2 (ATCC PTA-122342), which is derived from the wild-type strain and currently used for the industrial production of enduracidin. In the wild-type organism, site-specific integration of plasmid pXY152-endorf24, which drives the overexpression of a second copy of orf24, generated the strain SfpXY152endorf24. The integration of mutagenized fosmid pXYF24D3 into the wild-type chromosome replaced the native orf18 with a disrupted copy of the gene and created the mutant SfpXYF24D3. Working in the commercial producer *Streptomyces fungicidicus* BM38-2 (ATCC PTA-122342), integration of plasmid pXY152-endorf24 generated the recombinant strain *Streptomyces fungicidicus* BM38-2.24/16. To create a BM38-2 (ATCC PTA-122342)-derived strain lacking a functional orf18, plasmid pKS-T-orf18pfrd-AmR was constructed to delete orf18 and its flanking regions, replacing this region with an apramycin resistance marker and generating the recombinant strain *Streptomyces fungicidicus* BM38-2.18pfrd-AmR. The genetically manipulated strains were demonstrated to produce yields of enduracidin ranging from 1.2 to 4.6-fold higher than the respective parent strains. The elevated enduracidin yields from the recombinant strains provide a more cost-effective production of enduracidin.

The foregoing and other features and advantages of the disclosure will become more apparent from the following detailed description, which proceeds with reference to the accompanying figures.

BRIEF DESCRIPTION OF THE DRAWINGS

FIG. 9 provides an alignment of streptomycin activator StrR protein (SEQ ID NO: 25) with Orf24 (SEQ ID NO: 26).

FIG. 11 Alignment of Orf24 with six functionally characterized StrR-like pathway specific activator ortholog proteins from actinomycetes. Orf24 (GenBank accession no. DQ403252; SEQ ID NO: 26) from *S. fungicidicus* enduracidin biosynthetic gene cluster; StrR (GenBank accession no. Y00459; SEQ ID NO: 25) from *S. griseus* streptomycin biosynthetic gene cluster; Teil5* (GenBank accession no. AJ632270; SEQ ID NO: 32) from *Actinoplanes teichomyceticus* teicoplanin gene cluster; Bbr (GenBank accession no. Y16952; SEQ ID NO: 28) from *Amycolatopsis* strain DSM 5908 balhimycina biosynthetic gene cluster; KasT (GenBank accession no. BAF79690; SEQ ID NO: 29) from *S. kasugaensis* kasugamycin gene cluster; NovG (GenBank accession no. AF170880; SEQ ID NO: 30) from *S. niveus* strain NCIMB 9219 novobiocin biosynthetic gene cluster; SgcR1 (GenBank accession no. AY048670; SEQ ID NO: 31) from *S. globisporus* C-1027 biosynthetic gene cluster. Identical amino acids (*), conservative amino acids (.) and highly conservative amino acids substitutions (:). The conserved helix-turn-helix (HTH) motif characteristic of DNA-binding proteins like StrR is underlined.

FIG. 12 Alignment of Orf18 (SEQ ID NO: 36) with other functionally characterized response regulator orthologs. SCO1745/AbrA2: *S. coelicolor* A3(2) two-component response regulator (GenBank Accession No. CAB50960; SEQ ID NO: 33). SC03226/AbsA2: *S. coelicolor* A3(2) two-component response regulator (GenBank Accession No. AAB08053; SEQ ID NO: 34). SC03818: *S. coelicolor* A3(2) two-component system response transcriptional regulator (GenBank Accession No. CAB46941; SEQ ID NO: 35).

SEQUENCE LISTING

Figure 1:
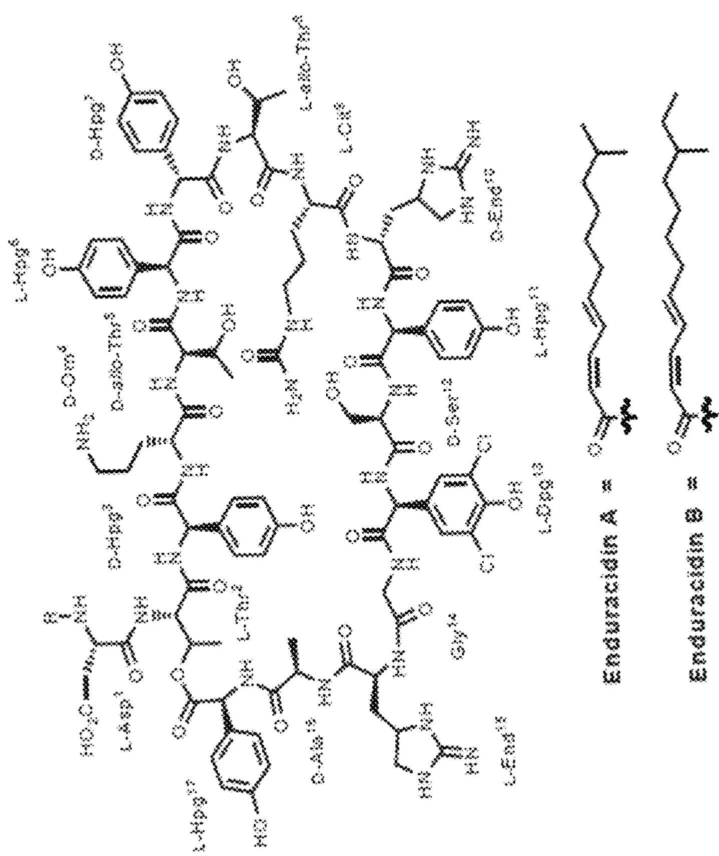
FIG. 1 provides the chemical structure of enduracidins A and B.

The nucleic and amino acid sequences listed herein and in the accompanying sequence listing are shown using standard letter abbreviations for nucleotide bases, and three letter code for amino acids, as defined in 37 C.F.R. 1.822. Only one strand of the nucleic acid sequence is shown, but the complementary strand is understood as included by any reference to the displayed strand. In the accompanying sequence listing:

SEQ ID NOs: 1 and 2 are oligonucleotide primers used to generate the insert of plasmid pXY152-endorf24.

SEQ ID NO: 3 is the nucleic acid sequence of plasmid pXY152-endorf24.

SEQ ID NOs: 4-7 are oligonucleotide primers used to generate the insert of plasmid pXY300-orf18ifd.

SEQ ID NO: 8 is the nucleic acid sequence of plasmid pXY300-orf18ifd.

SEQ ID NOs: 9 and 10 are oligonucleotide primers used to generate the oriT fragment of plasmid pKS-T-orf18pfrd.

SEQ ID NO: 11 is the nucleic acid sequence of plasmid pKS-T-orf18pfrd.

SEQ ID NOs: 12 and 13 are oligonucleotide primers used to generate the amR fragment of plasmid pKS-T-orf18pfrd-AmR.

SEQ ID NO: 14 is the nucleic acid sequence of plasmid pKS-T-orf18pfrd-AmR.

SEQ ID NOs: 15-18 are oligonucleotide primers used to generate the oriT and amR fragments of plasmid pKS-orf18ifd-T-AmR(NS).

SEQ ID NO: 19 is the nucleic acid sequence of plasmid pKS-orf18ifd-T-AmR(NS).

SEQ ID NO: 20 is the nucleic acid sequence of plasmid pXY152-endorf24-camtsr.

SEQ ID NOs: 21 and 22 are oligonucleotide primers used to generate the bla fragment of plasmid pXY152-endorf24-blatsr.

SEQ ID NO: 23 is the nucleic acid sequence of plasmid pXY152-endorf24-blatsr.

SEQ ID NO: 24 is an oligonucleotide primer which corresponds to a region of a apramycin resistance gene.

SEQ ID NO: 25 is the amino acid sequence of streptomycin activator StrR protein.

SEQ ID NO: 26 is the amino acid sequence encoded by ORF24.

SEQ ID NO: 27 is the nucleic acid sequence illustrating an in-frame deletion in orf18.

SEQ ID NO: 28 is the amino acid sequence of Bbr insert.

SEQ ID NO: 29 is the amino acid sequence of KasT insert.

SEQ ID NO: 30 is the amino acid sequence of NovG insert.

SEQ ID NO: 31 is the amino acid sequence of SgcR1 insert.

SEQ ID NO: 32 is the amino acid sequence of Teil5* insert.

SEQ ID NO: 33 is the amino acid sequence of response regulator ortholog SCO1745/AbrA2 from *S. coelicolor* A3(2) (GenBank Accession No. CAB50960).

SEQ ID NO: 34 is the amino acid sequence of response regulator ortholog SCO/3226/AbsA2 from *S. coelicolor* A3(2) (GenBank Accession No. AAB08053).

SEQ ID NO: 35 is the amino acid sequence of response regulator ortholog SC03818 from *S. coelicolor* A3(2) (GenBank Accession No. CAB46941).

SEQ ID NO: 36 is the amino acid sequence encoded by ORF18.

SEQ ID NO: 37 is the nucleic acid sequence of orf18.

SEQ ID NO: 38 is the nucleic acid sequence of orf24.

SEQ ID NO: 39 is the nucleic acid sequence of the fosmid pXYF148 with the orf24 located at nucleotide position 23109 through 24044).

SEQ ID NO: 40 is the nucleic acid sequence of fosmid pXYF24 with the orf18 located at nucleotide position 31091-31753).

DETAILED DESCRIPTION OF SEVERAL EMBODIMENTS

I. Introduction

Enduracidin (FIG. 1), also called enramycin, is a 17 amino acid lipodepsipeptide antibiotic produced by the soil bacterium *S. fungicidicus* B-5477 (ATCC 21013). The peptide is isolated from the fermentation broth and mycelia primarily as a mixture of enduracidins A and B, which differ by one carbon in the length of the attached lipid chain. Structurally, the enduracidins are distinguished by a $C_{12}$ or $C_{13}$ 2Z,4E branched fatty acid moiety attached by an amide linkage to an aspartic acid residue, and the presence of numerous nonproteinogenic amino acid residues such as enduracididine (End), 4-hydroxyphenylglycine (Hpg), 3,5-dichloro-4-hydroxyphenylglycine (Dpg), citrulline (Cit) and ornithine (Orn) (cf. FIG. 1). Seven of the 17 amino acids have the D configuration and six of the residues are Hpg or the chlorinated derivative Dpg.

Enduracidin (for simplicity, the peptides will be referred to singularly) exhibits potent in vitro and in vivo antibacterial activity against a wide spectrum of Gram-positive organisms, including methicillin-resistant *Staphylococcus aureus* (MRSA) and vancomycin-resistant *Enterococcus* (VRE). Minimum inhibitory concentrations (MICs) are as low as 0.05 μg/mL and the effect is bactericidal. A study with 100 strains of *S. aureus* collected from various pathological products, and including 40% MRSA, established MICs ranging from 0.09 to 0.56 μg/mL with no strain able to survive exposure to 1 μg/mL. For comparison, typical MICs for vancomycin toward sensitive strains of *S. aureus* range from 0.5 to 2 μg/mL. In addition, enduracidin has an excellent toxicological profile. In a study in mice, rabbits, dogs and monkeys the acute LD50s were: intravenous, 30-125 mg/kg; intraperitoneal, 750-910 mg/kg; subcutaneous, intramuscular (i.m.) or oral, >5-10 g/kg. In the same study, monkeys receiving enduracidin i.m. for 6 months and rats that were similarly dosed for 12 months were found to only have localized inflammation at the injection site. In humans, enduracidin was administered i.m. (100 mg every 12 hours) to 20 hospitalized adult patients infected with MRSA. The peptide was reported to be free of side effects and also highly effective for treating urinary tract and skin infections caused by MRSA, but not chronic bone infections (Peromet et al., *Chemotherapy* 19:53-61, 1973).

Enduracidin inhibits bacterial peptidoglycan cell wall biosynthesis by complexing with extracellular Lipid II, a precursor to the bacterial cell wall structure. The site of Lipid II complexation is distinct from that recognized by vancomycin and accounts for the action of enduracidin against vancomycin-resistant organisms. To date, there is no documented cross-resistance of enduracidin with any clinically-used antibiotic and no evidence of developed, acquired or transferrable resistance. The absence of any known form of transferrable resistance mechanism, the lack of oral bioavailability, its low toxicity, and excellent activity towards *Clostridium* spp. have made enduracidin a key commercial peptide antibiotic used as a poultry feed additive for controlling clostridial enteritis.

To derive a strain of the producing organism that could supply the quantities of the peptides required for commercial uses, Japan Takeda Animal Health (now part of Intervet/Merck Animal Health) subjected *S. fungicidicus* B-5477 to various traditional strain improvement methods and selected for mutants that produced higher yields of enduracidin. An increasing worldwide market for enduracidin has driven efforts to further improve the yield of this antibiotic in BM38-2 (ATCC PTA-122342). With the genetic sequence of the enduracidin biosynthesis gene cluster available (GenBank accession no. DQ403252 which is hereby incorporated by reference as available on the world wide web on Oct. 3, 2006, BM38-2 (ATCC PTA-122342) served as the starting strain for the targeted genetic manipulation of regulatory genes associated with the gene cluster and constituted the basis for this disclosure. Herein, it is disclosed that the product of orf18 has a negative effect on enduracidin production and the orf24 gene product has a positive effect on enduracidin production and that recombinant strains derived from both the *S. fungicidicus* wild-type and BM38-2 (ATCC PTA-122342) organisms that exploit these regulatory effects produce elevated yields of enduracidin. In addition, disclosed herein are new gene replacement and integrative expression vectors based on pBluescript II KS and pSET152, respectively.

II. Abbreviations and Terms a. Abbreviations

AA: amino acid
Am: apramycin
AmR: apramycin resistance marker
amRp: native apramycin resistance promoter
ATCC: American Type Culture Collection
bla: ampicillin resistance gene
BLAST: Basic Local Alignment Search Tool
cam: chloramphenicol resistance gene
CFU colony forming units
CTAB: Cetyl Trimethyl Ammonium Bromide
Cit: L-citrulline
Dpg: 3,5-dichloro-L-4-hydroxyphenylglycine
EDTA: disodium EthyleneDiamineTetra-Acetate
End: enduracididine
Enradin: Enduracidin, Enramycin
EPM: Enduracidin Production Medium
Hpg: D- and L-4-hydroxyphenylglycine
HPLC: High Performance Liquid Chromatography
HTH: Helix-Turn-Helix
IM: Intramuscular
ISP2: International *Streptomyces* Project Medium 2
ISP4: International *Streptomyces* Project Medium 4
LB: Luria-Bertani Broth
LD50: Lethal Dosage, an LD50 represents the individual dose required to kill 50 percent of a population of test animals
MAH: Intervet/Merck Animal Health
MeOH: Methanol
MICs: Minimum Inhibitory Concentrations,
MRSA: methicillin-resistant *Staphylococcus aureus*
nm: Nanometer
NRPS: non-ribosomal peptide synthetase
ORF: open reading frame
Orn: D-ornithine
PCP: peptidyl carrier protein
PCR: Polymerase Chain Reaction
Pfrd: Plus Flanking Region Deletion
SDS: Sodium Dodecyl Sulfate
SNP: single nucleotide polymorphism
SPD: Spectrophotodiode
TFA: TriFluoroacetic Acid
TSB: Tryptic Soy Broth
tsr Thiostrepton resistance gene
UV: ultraviolet
VRE: vancomycin-resistant enterococci b. Terms Unless otherwise noted, technical terms are used according to conventional usage. Definitions of common terms in molecular biology may be found in Benjamin Lewin Genes V published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administering: Administration by any route to the animal. As used herein, administration typically refers to oral administration.

Allelic variant: An alternate form of a polypeptide that is characterized as having a substitution, deletion, or addition of one or more amino acids. In one example, the variant does not alter the biological function of the polypeptide.

Amplification: When used in reference to nucleic acids, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No.

6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology,* 19th Edition (1995), chapter 28). When the changes to the original compound are substantial, or many incremental changes are combined, the compound is no longer an analog. For example, ramoplanin is not considered herein to be an analog of enduracidin: ramoplanin does not have either enduracididine amino acid, includes different amino acids, and though it has a lipid side chain, the chain length is substantially shorter. Analogs of enduracidin may be prepared by addition or deletion of functional groups on the amino acids that constitute the lipodepsipeptides, by substitution of one amino acid for another (excepting the enduracididine amino acids) or a combination of functional group modification and amino acid substitution. Exemplary enduracidin analogs include tetrahydroenduracidin A, tetrahydroenduracidin B, deschloroenduracidin A, and deschloroenduracidin B.

A derivative is a biologically active molecule derived from the base structure. A mimetic is a molecule that mimics the activity of another molecule by mimicking the structure of such a molecule, such as a biologically active molecule. Thus, the term "mimetic" indicates a definite structure related to activity.

Antibiotic: A substance, for example, enduracidin, penicillin or streptomycin, often produced by or derived from certain fungi, bacteria, and other organisms, that can destroy or inhibit the growth of other microorganisms.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Binding or stable binding: A molecule, such as an oligonucleotide or protein, binds or stably binds to a target molecule, such as a target nucleic acid or protein, if binding is detectable. In one example, an oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target: oligonucleotide complex. Binding between a target and an oligonucleotide can be detected by any procedure known to one of ordinary skill in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

The binding between a protein and its target protein, such as an antibody for an antigen, is frequently characterized by determining the binding affinity. In one embodiment, affinity is calculated by a modification of the Scatchard method described by Frankel et al., *Mol. Immunol.,* 16:101-106, 1979. In another embodiment, binding affinity is measured by a specific binding agent receptor dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

Biological function: The function(s) of a polypeptide in the cells in which it naturally occurs. A polypeptide can have more than one biological function.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity). The following table shows exemplar conservative amino acid substitutions:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |

-continued

| Original Residue | Conservative Substitutions |
|---|---|
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Control *Streptomyces fungicidicus* strain: The naturally-occurring wild-type strain, *Streptomyces fungicidicus* ATCC21013.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine, bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Domain: A portion of a molecule such as proteins or nucleic acids that is structurally and/or functionally distinct from another portion of the molecule.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Enduracidin: Enduracidins A and B are 17 amino acid lipodepsipeptides discovered in the late 1960s from fermentations of the soil bacterium *Streptomyces fungicidicus* B-5477 (ATCC 21013). The A and B peptides are homologs that differ by one carbon in the length of the attached lipid chain. Structurally, the enduracidins are distinguished by $C_{12}$ or $C_{13}$ 2Z,4E branched fatty acid moiety and the presence of numerous nonproteinogenic amino acid residues such as enduracididine (End), 4-hydroxyphenylglycine (Hpg), 3,5-dichloro-4-hydroxyphenylglycine (Dpg), citrulline (Cit) and ornithine (Orn). Seven of the 17 amino acids have the D configuration and six of the residues are Hpg or the chlorinated analog Dpg.

Functional fragments and variants of a polypeptide: Included are those fragments and variants that maintain one or more functions of the parent polypeptide. It is recognized that the gene or cDNA encoding a polypeptide can be considerably mutated without materially altering one or more of the polypeptide's functions. First, the genetic code degenerates, and thus different codons encode the same amino acids. Second, even where an amino acid substitution is introduced, the mutation can be conservative and have no material impact on the essential function(s) of a protein. See Stryer *Biochemistry* 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides, and labels useful for such purposes, include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Effective amount: A quantity or concentration of a specified compound or composition sufficient to achieve a desired effect in a subject. The effective amount may depend at least in part on the species of animal being treated, the size of the animal, and/or the nature of the desired effect.

Gene Cluster: A set of genetic elements grouped together on the chromosome, the protein products of which have a related function, such as forming a natural product biosynthetic pathway.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequences disclosed herein. Homology can be measured using sequence analysis software such as Sequence Analysis Software Package of the Genetics Computer Group, University of Wisconsin Biotechnology Center, 1710 University Avenue, Madison, WI 53705. Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Hybridization: Oligonucleotides and other nucleic acids hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between two distinct nucleic acid sequences or two distinct regions of the same nucleic acid sequence.

Specifically hybridizable and specifically complementary are terms that indicate a sufficient degree of complementarity such that stable and specific binding occurs between a first nucleic acid (such as, an oligonucleotide) and a DNA or RNA target. The first nucleic acid (such as, an oligonucleotide) need not be 100% complementary to its target sequence to be specifically hybridizable. A first nucleic acid (such as, an oligonucleotide) is specifically hybridizable when there is a sufficient degree of complementarity to avoid non-specific binding of the first nucleic acid (such as, an oligonucleotide) to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times also influence stringency. Calculations regarding hybridization conditions required for attaining particular degrees of stringency are discussed by Sambrook et al. (ed.) *Molecular Cloning: A Laboratory Manual,* 2nd ed., vol. 1-3, Cold Spring Harbor Laboratory Press, Cold Spring Harbor, NY, 1989, chapters 9 and 11.

The following are exemplary sets of hybridization conditions and are not meant to be limiting.

Very High Stringency (detects sequences that share 90% sequence identity)

Hybridization: 5×SSC at 65EC for 16 hours

Wash twice: 2×SSC at room temperature (RT) for 15 minutes each

Wash twice: 0.5×SSC at 65EC for 20 minutes each

High Stringency (detects sequences that share 80% sequence identity or qreater)

Hybridization: 5×-6×SSC at 65EC-70EC for 16-20 hours

Wash twice: 2×SSC at RT for 5-20 minutes each

Wash twice: 1×SSC at 55EC-70EC for 30 minutes each

Low Stringency (detects sequences that share greater than 50% sequence identity)

Hybridization: 6×SSC at RT to 55EC for 16-20 hours

Wash at least twice: 2×-3×SSC at RT to 55EC for 20-30 minutes each.

Isolated: An isolated biological component (such as a nucleic acid molecule or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Mutate: The process of causing a change in the sequence of a genetic material (usually DNA or RNA) of a cell or organism. Mutations can be intentionally introduced into genetic material using molecular techniques well known in the art (e.g., site-directed mutagenesis, PCR mutagenesis and others).

Nonribosomal peptide (NRP): A class of secondary metabolites, usually produced by microorganisms, such as bacteria and fungi. Unlike polypeptides synthesized on the ribosome, these peptides are synthesized by nonribosomal peptide synthetases (NRPS) from amino acids.

Nonribosomal peptide backbone assembly: The second step in nonribosomal peptide biosynthesis, which includes amide bond formation (condensation) of the peptide sequence.

Nonribosomal peptide synthetase (NRPS): A large multifunctional protein that synthesizes polypeptides by a nonribosomal mechanism, often known as thiotemplate synthesis (Kleinkauf and von Doehren Ann. Rev. *Microbiol.* 41: 259-289, 1987). Such nonribosomal polypeptides can have a linear, cyclic, or branched cyclic structure and often contain amino acids not present in proteins or amino acids modified through methylation or epimerization. In particular examples, NRPS produce dipeptides.

Nonribosomal peptide tailoring: The third step in nonribosomal peptide biosynthesis. There are numerous novel precursor amino acids found in nonribosomal peptides and many of these building blocks are formed or modified while attached to PCP domains of specialized proteins or the NRPS. This post-synthetic modification can occur after amide bond formation of the peptide backbone. Exemplary modifications include a-carbon epimerization, N-methylation, heterocyclization of Cys or Ser/Thr residues to thiazolines and oxazolines, and side chain halogenation or hydroxylation. Other modifications such as oxidation, alkylation, acylation and glycosylation can occur after release of the nascent peptide from the NRPS complex and are often needed for full biological activity.

Nonribosomal precursor amino acid biosynthesis: The first step in nonribosomal peptide biosynthesis. Nonribosomal peptides often possess amino acids not found in peptides and proteins that are assembled on ribosomes. These nonproteinogenic amino acids contribute to the diversity of these peptides and often have roles in their biological activity. Biosynthesis of these amino acids can occur via protein-bound intermediates or as free, soluble species.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Nucleotide: This term includes, but is not limited to, a monomer that includes a base linked to a sugar, such as a pyrimidine, purine or synthetic analogs thereof, or a base linked to an amino acid, as in a peptide nucleic acid. A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Open reading frame (ORF): A series of nucleotide triplets (codons) coding for amino acids without any internal termination codons. These sequences are usually translatable into a peptide. For example, ORF, open reading frame, and enduracidin ORF refer to an open reading frame in the enduracidin biosynthetic gene cluster as isolated from *Streptomyces fungicidicus*. The term also embraces the same ORFs as present in other enduracidin-synthesizing organisms. The term encompasses allelic variants and single nucleotide polymorphisms (SNPs). In certain instances the term enduracidin ORF is used synonymously with the polypeptide encoded by the enduracidin ORF and may include conservative substitutions in that polypeptide. The particular usage will be clear from context.

An open Reading Frame that has been nulled is an open reading frame that has been rendered non-functional through the deletion, insertion or mutation of one of more nucleotides in the coding sequence.

A *Streptomyces fungicidicus* comprising a diminished open reading frame-18 (orf 18) is an organism that has a decrease in, such as a 2-fold decrease, or even complete loss of the biological function of the gene product of orf18, relative to a wild type *Streptomyces fungicidicus* e.g., through genetic modification of orf18, including the orf18 being nulled as exemplified below, and/or through regulatory manipulation, e.g., modifying, inserting into, removing, and/or replacing non-coding regions of the gene encoding ORF18 that result in a decrease in the expression of the orf18 gene product. For example, the wild type promoter of orf18 could be modified so as to substantially decrease the transcription of orf18.

A *Streptomyces fungicidicus* comprising an augmented open reading frame-24 (orf24) is an organism that has an increase, such as a 2-fold increase or more, in the biological function of the gene product of orf24, relative to a wild type *Streptomyces fungicidicus*, e.g., through genetic modification of or/24 to enhance biological function of the gene product of orf24 and/or by regulatory manipulation, e.g., modifying, inserting into, removing, and/or replacing non-coding regions of the gene encoding ORF24 that result in an increase in the expression of the orf24 gene product. For example, the wild type promoter for orf24 was replaced with a strong constitutive promoter which enhanced the transcription of orf24, as exemplified below.

Modified gene: A gene sequence which contains a modification as compared to that found in the naturally occurring (wild-type) gene.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ortholog: Two nucleic acid or amino acid sequences are orthologs of each other if they share a common ancestral sequence and diverged when a species carrying that ancestral sequence split into two species. Orthologous sequences are also homologous sequences.

Polypeptide: A polymer in which the monomers are amino acid residues which are joined together through amide bonds. When the amino acids are alpha-amino acids, either the L-optical isomer or the D-optical isomer can be used, the L-isomers being preferred in some instances. The term polypeptide or protein as used herein encompasses any amino acid sequence and includes modified sequences such as glycoproteins. The term polypeptide is specifically intended to cover naturally occurring proteins (whether produced by ribosomal or nonribosomal mechanisms), as well as those that are recombinantly or synthetically produced.

The term polypeptide fragment refers to a portion of a polypeptide that exhibits at least one useful epitope. The phrase functional fragment of a polypeptide refers to all fragments of a polypeptide that retain an activity (such as a biological activity), or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

The term substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, CA, 1990). PCR primer pairs can be derived from a known sequence, for example, by using computer programs intended for that purpose such as Primer (Version 0.5, © 1991, Whitehead Institute for Biomedical Research, Cambridge, MA). The specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Regulating antibiotic production: To cause an alteration, such as an increase or decrease, in the amount, type or quality of antibiotic production. Disclosed herein are recombinant strains of *Streptomyces fungicidicus* with enhanced enduracidin production.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CAB/OS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, MD) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other under stringent conditions (see "Hybridization" above).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Transfected: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Transformed: A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Transposon: A mobile genetic element having nearly identical repeating sequences at either end, and containing at least a gene encoding a transposase (the enzyme needed to insert the transposon in the DNA sequence). Transposons can be integrated into different positions in the genome of a cell, or over an isolated plasmid, cosmid, or fosmid DNA template in vitro. Transposons may also contain genes other than those needed for insertion.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. A plasmid is a vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; Harlow and Lane, *Using Antibodies: A Laboratory Manual*, Cold Spring Harbor Laboratory Press, 1999; and Kieser, T., Bibb, M. J., Buttner, M. J., Chater, K. F., and Hopwood, D. A.: Practical *Streptomyces* genetics, John Innes Centre, Norwich Research Park, Colney, Norwich NR4 &UH, England, 2000.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Engineered Recombinant Expression Vectors of *Streptomyces fungicidicus*

Disclosed herein are engineered recombinant *Streptomyces fungicidicus* expression plasmid vectors. In some embodiments, an engineered recombinant *Streptomyces fungicidicus* vector comprises at least one selected open reading frame of *Streptomyces fungicidicus*. In some embodiments, an engineered recombinant *Streptomyces fungicidicus* vector comprises at least one selected open reading frame of *Streptomyces fungicidicus* expressed under the control of a promoter. In some examples, the promoter is a strong constitutive *Streptomyces* promoter that results in the enhanced production of enduracidin when the vector is expressed in a strain of *Streptomyces fungicidicus*. In some embodiments, the open reading frame is operatively linked to a heterologous promoter instead of its own native promoter. For example, it may be operatively linked to a constitutive promoter, such as a strong constitutive expression promoter or an inducible promoter. In some examples, the strong constitutive promoter is ermE*p from the erythromycin producer. In some examples, the inducible promoter is tipA. In some examples, the P(nitA)-NitR system (Herai S, Hashimoto Y, Higashibata H, Maseda H, Ikeda H, Omura S, Kobayashi M, Proc Natl Acad Sci USA. 2004. 101(39):14031-5) or the streptomycete promoter SF14 is employed. In some examples, a native promoter of the apramycin resistant gene (amRp) is employed. In some examples, $P_{hrdB}$, $P_{tcp830}$, $P_{SF14}$, $P_{ermE*}$ and/or Pneos are employed.

In some embodiments, the engineered recombinant vector comprises an open reading frame orf 24 (SEQ ID NO: 38) and/or open reading frame orf18 (SEQ ID NO: 37) which has been nulled. In some examples, the open reading frame orf18 (SEQ ID NO: 37) is nulled by an in-frame-deletion, frame-shifting and/or point mutation.

In some embodiments, the engineered recombinant vector comprises an open reading frame orf24 from the enduracidin gene cluster of *Streptomyces fungicidicus. In some examples, the open reading frame orf*24 (SEQ ID NO: 38) is operatively linked to a heterologous promoter. For example, it is linked to a strong constitutive promoter such as ermE*p. In other examples, the open reading frame orf24 is operatively linked to promoter tipA, SF14, amRp, $P_{hrdB}$, $P_{tcp830}$, $P_{SF14}$, $P_{ermE*}$ and/or Pneos.

In another embodiment, an engineered recombinant vector comprises an open reading frame orf18 that resides in the upstream region of the enduracidin gene cluster. The open reading frame orf18 (SEQ ID NO: 37) is nulled by insertional disruption, in-frame deletion, frame-shifting and/or point mutation. In some examples, the open reading frame orf18 is nulled by an in-frame deletion, such as an in-frame deletion as illustrated in FIG. 9B. In one example, the open reading frame orf18 (SEQ ID NO: 37) is nulled by an in-frame deletion. For example, the open reading frame orf18 (SEQ ID NO: 37) is nulled by an in-frame deletion of nucleic acids 5 through 660 of orf18 (SEQ ID NO: 37). In general, any internal in-frame deletion over orf18 results in a nulled function of Orf18 due to its incompleteness. In some examples, the in-frame deletion includes deletion of at least 3 nucleic acids in orf18 (SEQ ID NO: 37), such as at least 3 nucleic acids, including 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 221, 224, 227, 230, 233, 236, 239, 242, 245, 248, 251, 254, 257, 260, 263, 266, 269, 272, 275, 278, 281, 284, 287, 290, 293, 296, 299, 302, 305, 308, 311, 314, 317, 320, 323, 326, 329, 332, 335, 338, 341, 344, 347, 350, 353, 356, 359, 362, 365, 368, 371, 374, 377, 380, 383, 386, 389, 392, 395, 398, 401, 404, 407, 410, 413, 416, 419, 421, 424, 427, 430, 433, 436, 439, 442, 445, 448, 451, 454, 457, 460, 463, 466, 469, 472, 475, 478, 481, 484, 487, 490, 493, 496, 499, 502, 505, 508, 511, 514, 517, 520, 523, 526, 529, 532, 535, 538, 541, 544, 547, 550, 553, 556, 559, 562, 565, 568, 571, 574, 577, 580, 583, 586, 589, 592, 595, 598, 601, 604, 607, 610, 613, 616, 619, 621, 624, 627, 630, 633, 636, 639, 642, 645, 648, 651, or 654 nucleic acids between nucleic acids 5 through 660 of orf18 (SEQ ID NO: 37).

In related embodiments, an engineered recombinant plasmid vector involves two or more open reading frames from the enduracidin gene cluster and/or the regions flanking the gene cluster or from other actinomycete strains. The two or more open reading frames may be linked to a single promoter. Alternatively, they may be operatively linked to two different promoters. The two promoters may be the same type of promoter. Alternatively, they may be two different types of promoters.

In further embodiments, additional or alternative open reading frames that may enhance enduracidin production may be introduced, or inactivated, in the engineered strain of *Streptomyces fungicidicus*.

In some examples, the recombinant plasmid is pXY152-endorf24 (SEQ ID NO:3). In some examples, the recombinant plasmid is pXY300-orf18ifd (SEQ ID NO: 8). In some examples, the recombinant plasmid is pKS-T-orf18ifd (SEQ ID NO: 11). In some examples, the recombinant plasmid is pKS-T-orf18pfrd-AmR (SEQ ID NO: 14). In some examples, the recombinant plasmid is pKS-orf18ifd-T-AmR (NS)(SEQ ID NO: 19). In some examples, the recombinant plasmid is pXY152-endorf24-camtsr (SEQ ID NO: 20). In some examples, the recombinant plasmid is pXY152-endorf24-blatsr (SEQ ID NO: 23).

IV. Engineered Recombinant Strains of *Streptomyces fungicidicus*

Disclosed herein are engineered recombinant *Streptomyces fungicidicus* strains capable of producing enhanced enduracidin as compared to a control strain (such as a wild-type *Streptomyces fungicidicus* strain or industrial parent strain). In some embodiments, an engineered recombinant *Streptomyces fungicidicus* strain comprises at least one selected open reading frame from *Streptomyces fungicidicus* introduced onto the chromosome and expressed under the control of a promoter, such as a strong constitutive *Streptomyces* promoter, that results in the enhanced production of enduracidin in the engineered strain. In some embodiments, the expression of the introduced open reading frame in the *Streptomyces fungicidicus* is driven by a heterologous promoter instead of its own native promoter. For example, it may be operatively linked to a constitutive promoter, such as a strong constitutive expression promoter or an inducible promoter. In some examples, the strong constitutive promoter is ermE*p from the erythromycin producer. In some examples, the inducible promoter is tipA. In some examples, the P(nitA)-NitR system (see Herai S, Hashimoto Y, Higashibata H, Maseda H, Ikeda H, Omura S, Kobayashi M, Proc Natl Acad Sci USA., 2004. 101(39):14031-5) or the streptomycete promoter SF14 is employed. In some examples, the constitutive expression promoter is amRp. In some examples, $P_{hrdB}$, $P_{tcp830}$, $P_{SF14}$, $P_{ermE*}$ and/or Pneos promoters are employed.

In some embodiments, the engineered strain comprises an open reading frame orf24 from the enduracidin gene cluster of *Streptomyces fungicidicus*. In some examples, the open reading frame orf24 is operatively linked to a heterologous promoter. For example, it is linked to a strong constitutive promoter such as ermE*p. In other examples, the open reading frame orf24 is operatively linked to promoter tipA, SF14, amRp, $P_{hrdB}$, $P_{tcp830}$, $P_{SF14}$, $P_{ermE*}$ and/or Pneos.

In another embodiment, the engineered strain is related to an open reading frame orf18 that resides in the upstream region of the enduracidin gene cluster. The open reading frame orf18 is nulled by insertional disruption, in-frame deletion, frame-shifting and/or point mutation. In some examples, the open reading frame orf18 is nulled by an in-frame deletion, such as an in-frame deletion as illustrated in FIG. 9B. In one example, the open reading frame orf18 (SEQ ID NO: 37) is nulled by an in-frame deletion. For example, the open reading frame orf18 (SEQ ID NO: 37) is nulled by an in-frame deletion of nucleic acids 5 through 660 of (SEQ ID NO: 37). In general, any internal in-frame deletion over orf18 should result in a nulled function of Orf18 due to its incompleteness.

In related embodiments, the engineered strain involves two or more open reading frames from the enduracidin gene cluster and/or the regions flanking the gene cluster or from other actinomycete strains. The two or more open reading frames may be linked to a single promoter. Alternatively, they may be operatively linked to two different promoters. The two promoters may be the same type of promoter. Alternatively, they may be two different types of promoters.

In further embodiments, additional or alternative open reading frames that may enhance enduracidin production may be introduced, or inactivated, in the engineered strain of *Streptomyces fungicidicus*.

In some embodiments, the engineered strain of *Streptomyces fungicidicus* is derived from a wild type parent strain, such as, but not limited to, *Streptomyces fungicidicus* American Tissue Culture Company (ATCC) 21013. In other embodiments, the engineered strain of *Streptomyces fungicidicus* is derived from an industrial parent strain, such as, but not limited to BM38-2 (ATCC PTA-122342). In other embodiments, the engineered strain of *Streptomyces fungicidicus* is derived from the conventional mutant strains, such as, but not limited to *Streptomyces fungicidicus* ATCC 31729, *Streptomyces fungicidicus* ATCC 31730 and *Streptomyces fungicidicus* ATCC 31731.

In some embodiments, enhanced production of enduracidin is an at least 1.2 fold increase, such as at least 1.5 fold, at least 2 fold, at least 2.5 fold, at least a 3 fold, at least a 3.5 fold, at least a 4 fold, at least a 4.5 fold increase, including, but not limited to a 1.2 to 10 fold increase, a 1.2 to 4.6 fold increase, a 2 to 5 fold increase, such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5 and 10 fold increase in enduracidin production as compared to the control *Streptomyces fungicidicus* strain. In some embodiments, the control *Streptomyces fungicidicus* strain is a wild-type *Streptomyces fungicidicus* strain, including, but not limited to, *Streptomyces fungicidicus* American Tissue Culture Company (ATCC) 21013 or an industrial parent strain, such as, but not limited to, BM38-2 (ATCC PTA-122342), or the conventional mutant strain, such as, but not limited to *Streptomyces fungicidicus* ATCC 31729, *Streptomyces fungicidicus* ATCC 31730 and *Streptomyces fungicidicus* ATCC 31731. In one example, the control is *Streptomyces fungicidicus* ATCC 21013 and the increase in enhanced enduracidin production is at least a 1.2 fold increase, such as a 1.2 to 4.6 fold increase. In one example, the control is *Streptomyces fungicidicus* BM38-2 (ATCC PTA-122342) and the increase in enhanced enduracidin productions is at least a 1.2 fold increase, such as a 1.2 to 4.6 fold increase.

V. Construction of Engineered Recombinant Strains of *Streptomyces fungicidicus*

In embodiments, recombinant strains of *Streptomyces fungicidicus* may be constructed by integration of a recombinant plasmid comprising at least one enduracidin production enhancing open reading frame into the chromosome of a parent strain of *Streptomyces fungicidicus*. The integrative conjugal vector may have, or may be engineered to have, a strong constitutive *Streptomyces* promoter. In some embodiments, the plasmid may lack a streptomycete replicon and may be integrated into the chromosome by site-specific single crossover homologous recombination. In other embodiments, the plasmid may be present as a free plasmid. In some embodiments, an conjugal vector may be engineered in which the plasmid insert carries a partially or completely deleted gene of interest, and its flanking regions, that may be integrated into the chromosome after double crossover homologous recombination to generate an in-frame deletion mutant.

VI. Production of Enduracidin from Engineered Recombinant Strains of *Streptomyces fungicidicus*

The engineered recombinant strains of *Streptomyces fungicidicus* provided by the present disclosure provide for methods of producing enhanced levels of enduracidin. This technical advance in the art allows for significant cost savings associated with the production of enduracidin. In some examples, methods of producing enduracidin comprises culturing a disclosed recombinant strain of *Streptomyces fungicidicus* under conditions sufficient for producing enduracidin. In some examples, the method further comprises isolating the enduracidin from the culture medium following culturing. In some examples, the method further comprising determining the antibacterial activity of the produced enduracidin, such as by HPLC analysis or bioassay using the *S. aureus* ATCC 29213 or *Bacillis subtilis* ATCC 6633 as indicating microorganisms.

In some examples, enduracidin is produced by a disclosed *Streptomyces fungicidicus* strain by utilizing fermentation conditions as previously described for the production of enduracidin (Higashide et al. *J. Antibiot.* 21: 126-137, 1968). After production, the compounds can be purified and/or analyzed including HPLC analysis as described in Example 1. Methods of producing enduracidin and harvesting this compound from growth medium can be found in U.S. Pat. No. 4,465,771, which is hereby incorporated by reference in its entirety.

In some examples, a disclosed *Streptomyces fungicidicus* strain is cultured in tryptic soy broth (TSB) on a shaker (such as at 225 rpm and 30° C. for 48 hours) and then transferred to a enduracidin production medium (EPM, Table 1 below) for a period of time for continuous fermentation, such as for at least five days and up to eleven days, including 5, 6, 7, 8, 9, 10 or 11 days of continuous fermentation. In some examples, production of enduracidin by the wild-type and derivative strains is conducted in automatic fermenters.

TABLE 1

Enduracidin Production Medium (EPM) Composition (pH 6.7)

| Ingredient | Concentration (%) |
|---|---|
| Soluble starch | 1.5 |
| Glucose | 1.0 |
| Corn flour | 2.5 |
| Corn gluten meal | 2.0 |
| Corn steep liquor | 0.25 |
| Sodium chloride | 0.25 |
| NaH2PO4 | 1.3 |
| KH2PO4 | 0.05 |
| (NH4)2SO4 | 0.15 |
| CaCO3 | 0.5 |
| Lactose | 0.5 |
| ZnCl2 | 0.005 |
| Chicken oil | 0.7 |

In some examples, *Streptomyces fungicidicus* biomass is produced by a fermentation process in deep tank sanitary design industrial fermenters with systems to monitor and control pH, temperature, oxygen, aeration, agitation. For example, each fermented batch of *S. fungicidicus* is initiated from a characterized and controlled working seed stock of the production seed stored in a secure location and held in low temperature environment.

In some examples, the fermentation process occurs in one or more stages, such as following three stages and can optionally be followed by further processing downstream:

Stage I:

Characterized established working seed cultures are used to start a fermentation batch. One-to-five vials of frozen seed vials are retrieved from low temperature storage and thawed either naturally or placed in a water bath at 28° C.-32° C. until the contents are thawed. The thawed culture(s) are aseptically transferred into sterile water held at room temperature and gently mixed to re-suspend the culture.

Stage II:

The re-suspended culture is aseptically transferred into 0.005 m3-0.05 m3 seed medium. The seed medium is composed of glucose (0.1-1.0 g/L), Dextrin (0.1-3 g/L), corn steep liquor (0-5.0 mL/L), soybean powder (1-5.0 g/L), ammonium sulfate (0.1-0-0.5 g/L), mono-potassium phosphate (0.13-0.54 g/L), ferrous sulfate (0.00-0.5 g/L), potassium hydroxide (0.13 mL/L), calcium carbonate (1-2 g/L), silicone-based de-foaming agent (0.1 mL/L), water, q. s. The medium is sterilized at 125° C.-128° C. for 30-45 minutes and then cooled to 28° C.-32° C. The volume of medium is adjusted using sterile water to the desired working volume. The pH is adjusted to 6.5-7.0.

The operating parameters of the seed scale up cycle include: Incubation temperature of 28° C.±2° C., an internal pressure of 1.0±0.5 kg/cm2, an aeration rate of 3±2 Nm3/min, and agitation rate of approximately 80 rpm, depending upon size and configuration of the vessel. The pH, oxygen consumption and viscosity is monitored but not controlled. The culture is grown for 40-80 hours before transfer into the main production fermenter. The viscosity at the time of transfer should range from 200-600 cps, and the pH should be <6.0, and there should be an increase in oxygen consumption. The seed culture is aseptically transferred into the main fermentation medium to complete the fermentation cycle.

Stage III:

Production Fermenter medium (10 m3-250 m3) composition includes natural and chemical components such as corn flour (13.0-15.0 w/v %), corn gluten meal (3.0-6.0 w/v %), cotton seed flour (0.1-0.3 w/v %), corn steep liquor (0.1-0.6 v/v %), sodium chloride (0.3 w/v %), ammonium sulfate (0.25-0.6 w/v %), lactic acid (0-0.5 v/v %), zinc chloride (0.01 w/v %), ferrous sulfate (0.0-0.02 w/v %), potassium hydroxide (0.20-0.5 v/v %), calcium sulfate (0.0-0.5 w/v %), calcium carbonate (0.5 w/v %), amylase (0.02-0.06 w/v %), potassium hydroxide (0.05 v/v %), vegetable oil (0.5-2.0 v/v %), de-foaming agent, and water, q. s. The ingredients ae added according to the order listed. Add water to the ingredients then heat to 70-90° C. to allow the enzyme to break down the complex carbohydrates for 15 minutes at temperature. Add remaining ingredients, adjust pH to 6.6-6.8, and add water q. s., sterilize at 125° C.-128° C. for 25-50 minutes to sterilize the media. Cool the media to 25° C.-32° C., and add water to q. s., working volume.

Transfer the contents from the seed fermenter into the main fermentation medium and set the fermenter to the following conditions: Temperature 28° C.±3° C., aeration rate 20-60 Nm3/min, internal pressure 0.1-1.0 kg/cm2, agitation rate equivalent to about 1.85 kW/m3. The aeration rate, internal pressure and agitation rates are adjusted a needed to ensure that the dissolved oxygen is not a rate limiting determinate. Carefully control foaming throughout the cycle to prevent contamination or outflow. Start controlling pH after oxygen demand increases. The following parameters are controlled and/or monitored throughout the fermentation cycle: pH, aeration, dissolved oxygen, CO2, viscosity, purity, agitation speed, internal pressure, and residual sugar. Maintain pH at 6.8 until the bacteria growth ceases, then allow pH to change naturally until harvest. The typical fermentation cycle is 210-300 hours. The culture is ready to be harvested when potency is greater than 5,000 µl/L, pH rises to 7.5 or higher, viscosity decreases, and oxygen demand ceases.

The fermentation is harvested by heating the culture to 70° C. for 30 minutes to inactivate the bacteria, and then cool the harvest fluids to 25° C.–32° C.

In some examples, downstream processing includes removing water from the biomass, drying the biomass and formulating the dried biomass into a premix.

Deposits of Biological Material

The following biological materials have been deposited under the terms of the Budapest Treaty with The American Type Culture Collection, and given the following accession numbers:

| Deposit | Accession Number | Date of Deposit |
|---|---|---|
| BM38-2-18pfrd | PTA-124007 | Mar. 2, 2017 |
| BM38-2-24/16 | PTA-124006 | Mar. 2, 2017 |

The above strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposits represent substantially pure culture of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The following non-liming examples are provided to illustrate certain particular features and/or embodiments. These examples should not be construed to limit the disclosure to the particular features or embodiments described.

EXAMPLES

Example 1

Materials and Methods for Enhanced Enduracidin Production

This example provides representative methods for enhanced enduracidin production.

Bacterial Strains, Plasmids, Fosmids and Culture Conditions.

*Streptomyces fungicidicus* B-5477 (ATCC 21013) and *Escherichia coli* S17-1 (ATCC 47055) were purchased from ATCC. The *S. fungicidicus* strain BM38-2 (ATCC PTA-122342) and standards of enduracidins A and B were provided by Intervet/Merck Animal Health (MAH). *E. coli* strains DH5a (Life Technologies, Inc.), EP1300 (Epicentre) and XL10-Gold (Stratagene) were used as hosts for *E. coli* plasmids, fosmids and *E. coli-Streptomyces* shuttle vectors. Plasmids pSET152 (Bierman et al., *Gene* 116: 43-49, 1992, which is hereby incorporated by reference in its entirety) and plJ773 were provided by Professor Keith Chater (JIC, Norwich, UK). Plasmid pWHM860 harboring ermE*p promoter was provided by Professor Bradley Moore (UCSD, San Diego). ISP2 (Difco™ ISP Medium 2), ISP4 and TSB (Bacto™ Tryptic Soy Broth) were purchased from VWR. Primers used for PCR and DNA sequencing were synthesized from Fisher and Sigma-Aldrich. Media and culture conditions for growing *S. fungicidicus* were described by Higashide et al. (*Journal of Antibiotics,* 21:126-137, 1968). All *E. coli* procedures were performed according to standard protocols.

DNA Isolation and Manipulations.

To prepare genomic DNA from *S. fungicidicus* B-5477, BM38-2 (ATCC PTA-122342) and derivative recombinant and mutant strains for sequencing, fosmid library construction, subcloning and PCR, freshly harvested spores from the individual strains were inoculated and grown in 100 mL TSB liquid medium supplemented with 5 mM $MgCl_2$ and 0.5% glycine. The representative culture was conducted in 500 mL Erlenmeyer flasks on a rotary shaking incubator at 225 rpm and 30° C. for 48 to 72 hours. Mycelial cells were harvested by centrifugation at 4000 rpm and 4° C. for 15 minutes. The supernatant was discarded and the pellet was successively washed once with 10.3% sucrose and twice with 10 mM Tris-HCl and 1 mM disodium ethylenediaminetetra-acetate (EDTA), pH 8.0 (TE buffer). The wet cells, equivalent to the volume of 80 μL water were distributed into 1.5 mL sterile micro-centrifuge tubes. After adding 300 μL of the lysis solution containing 200 μL of 10 mM Tris-HCl and 1 mM EDTA, pH 8.0 and 0.3 M sucrose (TES buffer), 50 μL of 0.5 M EDTA, 50 μL of lysozyme (50 mg/mL), the tubes were incubated at 37° C. for 30 to 60 minutes until the solution became viscous. Next, 5 μL of proteinase K (20 mg/mL) and 180 μL of 10% sodium dodecyl sulfate (SDS) were added to each tube. After gentle but thorough mixing, the solutions were incubated at 37° C. for 90 minutes. Then, 80 μL of 10% Cetyl Trimethyl Ammonium Bromide (CTAB) was added. After thorough mixing, the tubes were incubated at 65° C. for 10 minutes. The solutions were extracted twice with 600 μL of phenol/chloroform/isoamyl alcohol (25/24/1). The genomic DNA in the upper aqueous phases were recovered and precipitated with 0.6 volume of isopropanol. The harvested genomic DNA was washed twice with 70% ethanol. After drying at room temperature for 10 minutes, the genomic DNA was dissolved in 50 to 100 μL of sterile water. The high quality of the genomic DNA preparation was confirmed by digestion with HindIII and Sau3AI which showed complete digestion and no degradation of undigested genomic DNA by 0.8% agarose gel electrophoresis. Pooled genomic DNA was further digested with RNase to remove RNA contamination. The purity and quantity of the genomic DNA were determined with a Nanodrop spectrophotometer. General streptomycete DNA manipulations including agarose gel electrophoresis were performed and QIAprep Spin Miniprep kits (Qiagen) were used to prepare plasmids and fosmids from *E. coli* strains. Restriction endonucleases, DNA ligase, DNA polymerase, transposase, Klenow enzyme, alkaline phosphatase and ligase were purchased from Biolabs, Invitrogen, Epicentre and Roche, and used according to the manufacturers' recommendations. DNA fragments were purified using QIAquick Gel Extraction kits.

PCR.

The colony PCR was conducted as follows: spores from independent mutant candidate colonies were inoculated in TSB liquid culture. After growing for 48 to 72 hours, mycelia were harvested by centrifugation and washed twice with TE buffer (10 mM Tris, 1 mM EDTA), pH 8.0. Mycelia were re-suspended in sterile $H_2O$ and used as template in PCR reaction mixture in a final volume of 100 μL containing 60 μL of mycelia, 150 μmol of each primer, 20 μL of 5× AccuPrime GC-rich buffer A (Invitrogen), and 1 μL of Polymix (added at 80° C.) from the Expand long template PCR system (Roche). PCR was performed as follows: 1 cycle at 95° C. for 3 minutes, 30 cycles at 95° C. for 1 minute, at 55° C. for 1 minute, and at 72° C. for 2 minutes. The reaction was terminated with one extension cycle at 72° C. for 10 minutes. PCR products were gel-purified and sequenced. General PCR was similarly conducted as described above except that the isolated genomic DNA, plasmid/fosmid DNA was used as template instead of the direct use of DNA released from mycelial colonies without prior purification.

Construction of the Integrative Expression Plasmid pXY152-Endorf24

Figure 2:
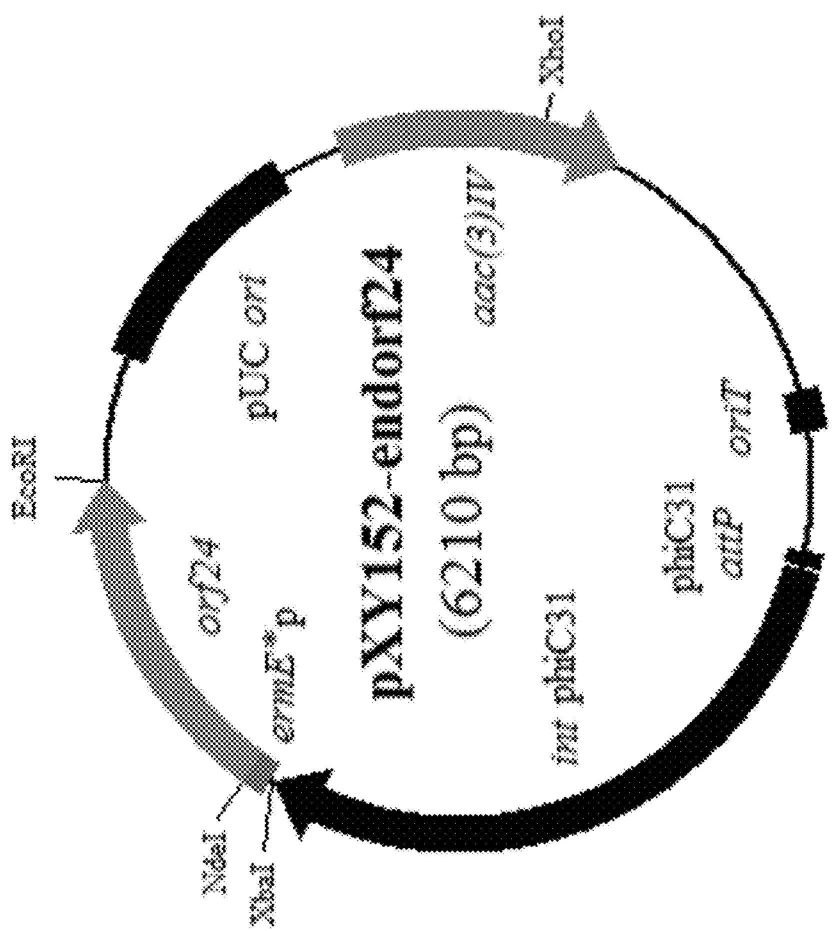
FIG. 2 is a map of the integrative expression plasmid pXY152-endorf24.

In order to ectopically express the putative regulatory gene orf24 from the enduracidin gene cluster in *S. fungicidicus* wild-type and BM38-2 (ATCC PTA-122342) strains, orf24 was cloned into the integrative plasmid pXY152 derived from pXY152aR20 (Yin et al., *J. Natural Products,* 73: 583-589, 2010 which is hereby incorporated by reference in its entirety) orf24 was PCR-amplified from *S. fungicidicus* genomic DNA using the forward primer (End24Ndpf: 5'-CCACCACATATG-GAAATAAGTTCGCTCTCCA-3' (SEQ ID NO:1, NdeI site is in bold) and the reverse primer (End24ERpr:5'-GTGTGT-GAATTCCTCGTTCACCCGGCCAGATG-3' (SEQ ID NO: 2, EcoRI site is in bold). The PCR product was digested with NdeI and EcoRI. The gel-purified orf24 fragment was then ligated with the similarly restricted vector pXY152. The resulting plasmid was designated pXY152-endorf24 (FIG. 2; SEQ ID NO: 3). The orf24 insert was confirmed to be error free by sequencing.

Figure 3:
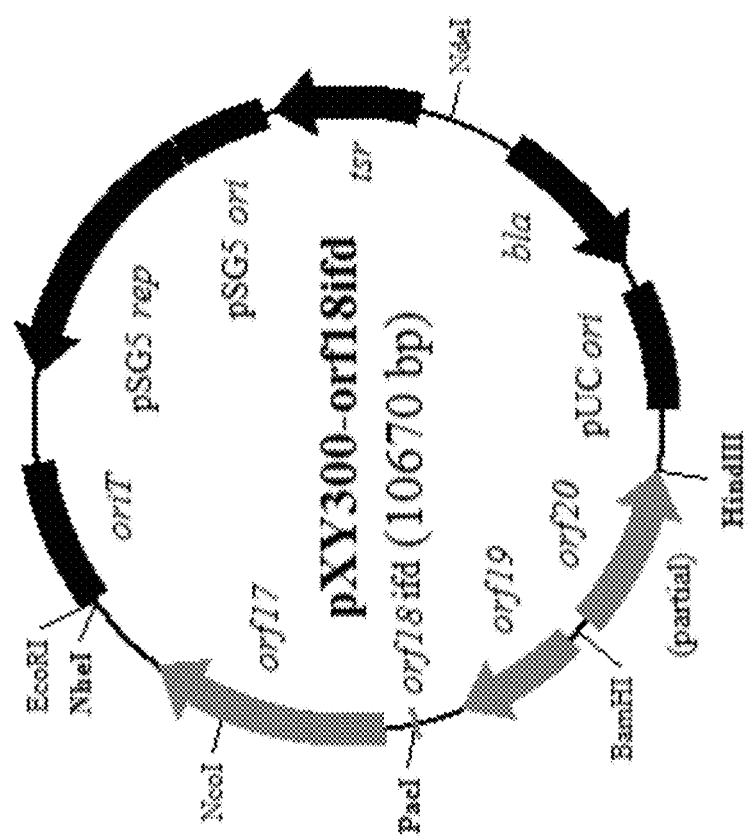
FIG. 3 is a map of the gene deletion plasmid pXY300-orf18ifd.

Construction of Plasmid pXY300-orf18ifd for In-Frame Deletion of Orf18 pXY300-orf18ifd was constructed by cloning two fragments that flank orf18 and are destined for deletion into pXY300, an *E. coli-Streptomyces* shuttle conjugal temperature-sensitive vector containing the thiostrepton resistance gene (tsr) for selection in *S. fungicidicus*. An "upstream" 2 kb and a "downstream" 2 kb flanking sequence, designated orf18ifdNP and orf18ifdPH, respectively, that flank orf18 were generated by PCR using *S. fungicidicus* genomic DNA as the template and two sets of primers. Fragment orf18ifdPH was amplified by using the forward and reverse primers (Ifdenorf18pf1, 5'-TTATT-GAAGCTTGCCGGGGCCGACGCGGCGGGCGGCCT-3' (SEQ ID NO: 4), Ifdendorf18pr1, 5'-GTTGTTTTAAT-TAAACACCAGGCCTCCTGGGGTG-3' (SEQ ID NO: 5), HindIII and PacI sites are in bold). Fragment orf18ifdNP was amplified by using the forward and reverse primers (Ifdendorf18pf2, 5'-TTTATATTAAT-TAATGACCCTTCCGTCCCGCCCCCGAT-3' (SEQ ID NO: 6), Ifdendorf18pr2, 5' TTTGGTGCTAGCTGGTCGTGGCGCTGTTCC-3' (SEQ ID NO: 7), PacI and NheI sites are in bold). These two PCR fragments were appropriately restricted and simultaneously ligated with the pXY300 vector prepared by digestion with NheI and HindIII, to yield plasmid pXY300-orf18ifd (FIG. 3; SEQ ID NO: 8). The error-free in-frame deletion insert of pXY300-orf18ifd was confirmed by sequencing.

Construction of Plasmid pKS-T-orf18pfrd-AmR for Deletion of Orf18 and its Flanking Regions.

Figure 4:
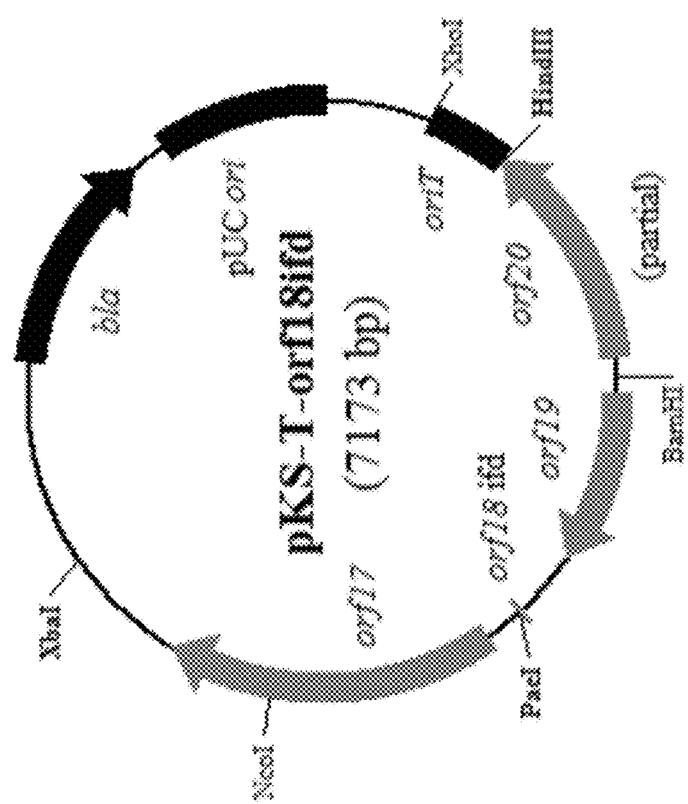
FIG. 4 is a map of the gene deletion plasmid pKS-T-orf18ifd.

The oriTfragment was amplified by PCR from plasmid pIJ773 using the forward primer (Oritnhexbahd3f, 5'-AGCACAGCTAGCTTCTAGAAGCTTCATT-CAAAGGCCGGCA-3' (SEQ ID NO: 9) HindIII site is in bold) and the reverse primer (Oriter1 pstxhor, 5'-GCCAGT-GAATTCTGCAGCTCGAGCAGAGCAGGAT-TCCCGTTGA-3' (SEQ ID NO: 10), XhoI site is in bold). The oriTfragment was digested with HindIII and XhoI, gel-purified and then ligated into the similarly restricted vector pBluescript II KS derivative to yield plasmid pKS-T (Alting-Mees and Short, Nucleic acids Research, 17: 9494, 1989). The insert of plasmid pXY300-orf18ifd was excised by digestion with NheI and HindIII, gel-purified and then ligated with NheI and HindIII linearized plasmid pKS-T to afford the plasmid pKS-T-orf18ifd (FIG. 4; SEQ ID NO: 11). A 1 kb fragment carrying aac(3)IV, the apramycin resistance gene (amR), was amplified from pIJ773 using forward primer (ApraNcolpf, 5'-GAATGGCCATGGTT-CATGTGCAGCTCCAT-3' (SEQ ID NO: 12), NcoI site is in bold) and reverse primer (ApraBamHlpr, 5'-TCTCGAG-GATCCGAATAGGAACTTCGGAAT-3' (SEQ ID NO: 13), BamHI site is in bold). Digestion of the fragment AmR and plasmid pKS-T-orf18ifd with NcoI and BamHI prepared both the insert and vector for ligation. The resulting plasmid was designated pKS-T-orf18pfrd-AmR (FIG. 5; SEQ ID NO: 14).

Construction of Plasmid pKS-T-orf18ifd-AmR(NS) for In-Frame-Deletion of orf18.

Figure 6:
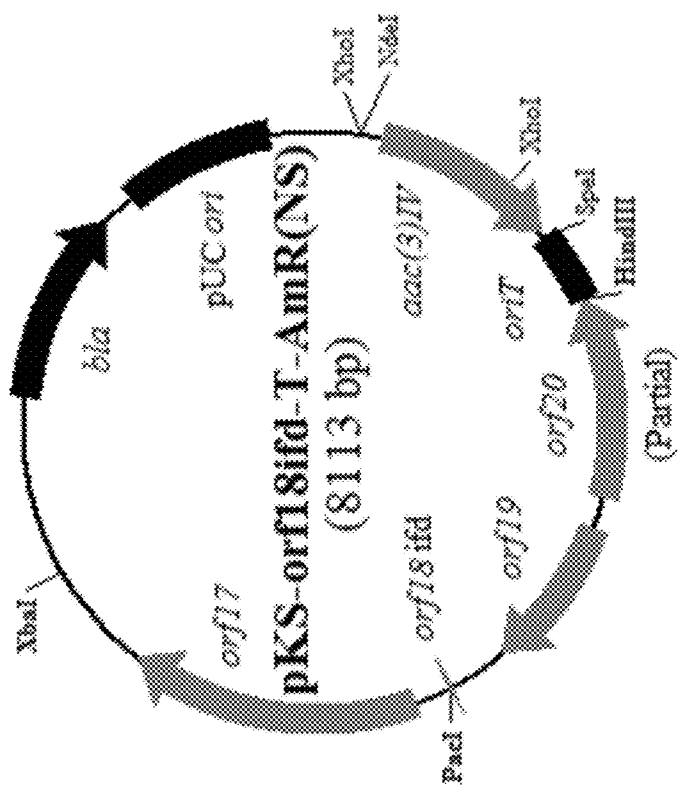
FIG. 6 is a map of the gene deletion plasmid pKS-orf18ifd-T-AmR(NS).

The insert of pXY300-orf18ifd was excised by digestion with NheI and HindIII, gel-purified and then ligated with SpeI and HindIII linearized vector pBluescript II KS to produce a plasmid pKS-orf18ifd. The oriTfragment was amplified by PCR using the forward primer (Oritnhexbahd3f, 5'-AGCACAGCTAGCTTCTAGAAGCTTCATT-CAAAGGCCGGCA-3' (SEQ ID NO: 15), HindIII site is in bold) and the reverse primer (oriTXhNdSpr, 5'-AGGCAGCTCGAGCATATGACTAGTCAGAGCAG-GATTCCCGTTGA-3'(SEQ ID NO: 16), XhoI, NdeI and SpeI sites are in bold). The oriTfragment was digested with XhoI and HindIII, gel-purified and then ligated with the similarly restricted plasmid pKS-orf18ifd to obtain a plasmid pKS-orf18ifd-T. A 1 kb fragment carrying aac(3)IV gene conferring apramycin resistance (AmR) was amplified from pIJ773 by PCR using the forward primer (ApraNdepf, 5'-GAATGGCATATGGTTCATGTGCAGCTCCAT-3' (SEQ ID NO: 17), NdeI site is in bold) and the reverse primer (ApraSpeIpr, 5'-TCTAGAACTAGTGAATAG-GAACTTCGGAAT-3' (SEQ ID NO: 18), SpeI site is in bold). Plasmid pKS-orf18ifd-T was linearized by digestion with NdeI and SpeI and then ligated with the similarly restricted fragment AmR to generate the plasmid pKS-orf18ifd-T-AmR(NS) (FIG. 6; SEQ ID NO: 19).

Intergeneric Conjugation, pXY300-Based and pKS-Based Gene Disruption Procedures.

The gene disruption plasmids were individually introduced into *E. coli* S17-1 by transformation and then transferred to *S. fungicidicus* or its derivatives via conjugation. Briefly, freshly harvested *S. fungicidicus* spores were pre-germinated and *E. coli* S17-1 cells were grown overnight at 37° C. in Terrific broth. Serial dilutions of the germinated spore suspension were made and 100 mL of each dilution was mixed with an equal volume of *E. coli* S17-1 harboring the pXY300-based disruption plasmids. The solutions were plated onto ISP4 agar plates with addition of 10 mM $MgCl_2$ and incubated for 22 hours at either 30 or 37° C. Each plate was overlaid with 3 mL soft nutrient agar containing sodium nalidixate and apramycin (0.5 mg/mL) and further incubated at 30° C. for about one week. Isolated exconjugants that survived antibiotic selection were purified by streaking onto ISP4 agar plates supplemented with sodium nalidixate and apramycin (50 μg/mL each).

To conduct the gene disruption studies with the pXY300-based plasmids, exconjugants were first cultured in TSB liquid medium containing apramycin (5 μg/mL) at 30° C. for 24 hours at which time the mycelia were harvested, homogenized and used to inoculate TSB liquid media supplemented with apramycin (5 μg/mL). After 3-6 days incubation at 40° C., the mycelia were homogenized and plated onto ISP4 agar plates containing apramycin (50 μg mL) and incubated at 30° C. for one week. Genomic DNA was isolated from randomly selected individual surviving colonies and analyzed by either PCR or Southern blot to confirm that single- or double crossover disruption had occurred. For pKS-based gene disruption and in-frame-deletion plasmids, exconjugants were passed through three successive rounds of incubations on ISP4 agar plates for sporulation without addition of any antibiotic selection in order to stimulate the conversion to double crossover recombinants. The pKS-based exconjugants were not passed through the 40° C. temperature selection. The correct construction of all mutants was confirmed by PCR and/or Southern blot analysis.

Construction of the Integrative Expression Plasmids pXY152-endorf24-camtsr and pXY152-endorf24-Blatsr.

Figure 7:
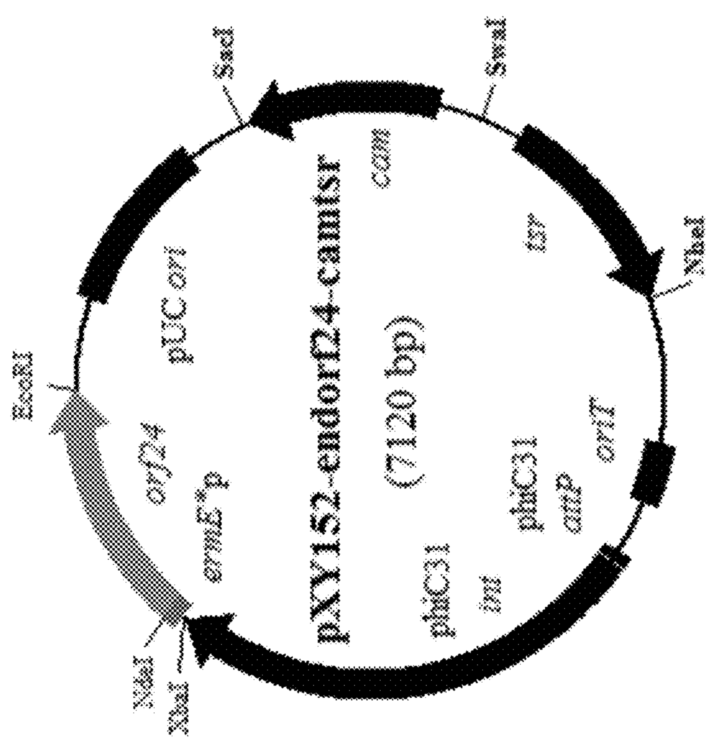
FIG. 7 is a map of the integrative expression plasmid pXY152-endorf24-camtsr.
Figure 8:
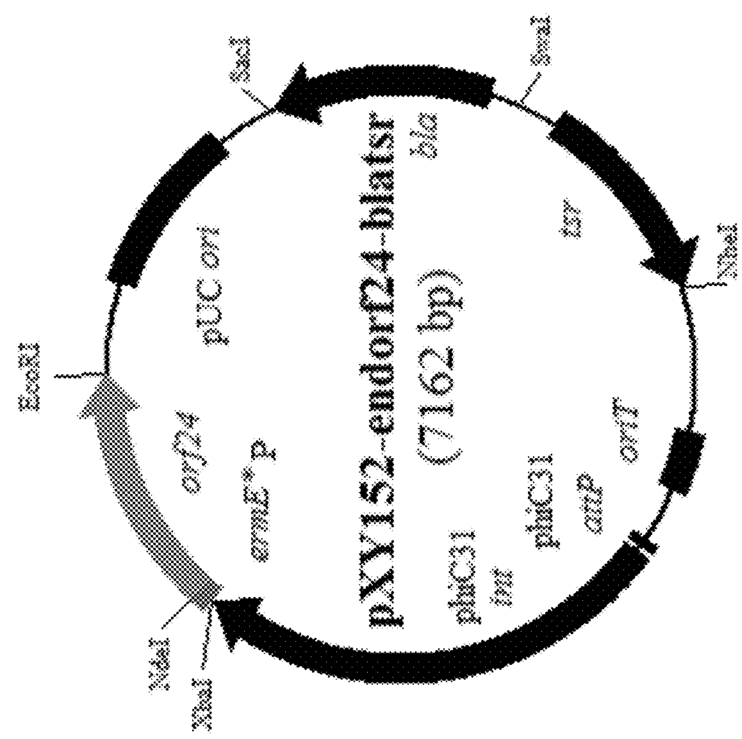
FIG. 8 is a map of the integrative expression plasmid pXY152-endorf24-blatsr.

To ectopically express orf24 in the apramycin resistant mutant carrying the deletion of orf18 and its flanking regions, the integrative expression plasmid pXY152-endorf24-blatsr was designed. To construct this plasmid, a cassette (camtsr) harboring the chloramphenicol resistance gene and thiostrepton resistance gene (tsr) was excised from a plasmid pUC57 derivative by digestion with SacI and NheI. The camtsr cassette was then ligated with SacI and NheI linearized plasmid pXY152-endorf24 to yield a new construct pXY152-endorf24-camtsr (FIG. 7; SEQ ID NO: 20). An ampicillin resistance gene (bla) was PCR-amplified from pBluescript KS using the forward primer (amp2956SwaIpf, 5'-GTGGCAATTTAAATG-GAAATGTGCGCGGAA-3' (SEQ ID NO: 21), SwaI site is in bold) and reverse primer (amp1973SacIpr, 5'-TATATAGAGCTCAACTTGGTCTGACAGTTAC-3' (SEQ ID NO: 22), SacI site is in bold). bla was then cloned into the SacI and SwaI sites of pXY152-endorf24-camtsr to replace the cassette camtsr with blatsr. The resulting conjugal expression plasmid was designated pXY152-endorf24-blatsr (FIG. 8; SEQ ID NO: 23).

Construction of the Tn5AT Cassette for In Vitro Transposon Mutation

The Tn5AT cassette was designed to combine three genetic elements: the transposon Tn5, oriT and aac3 (IV). Tn5 is specifically and uniquely recognized by Tn5 transposase (Epicentre) and readily inserts into high G+C *Streptomyces* DNA cloned into *E. coli* plasmids and fosmids (also referred to in U.S. Pat. No. 8,188,245 which his hereby incorporated by reference). oriT is required for the conjugal transfer of DNA from *E. coli* S17-1 to *Streptomyces* and aac(3)IV is an *E. coli*-*Streptomyces* bifunctional selection marker conferring apramycin resistance. Both oriT and aac3 (IV) were excised from plasmid pIJ773 as a XbaI fragment and then cloned into the transposon donor plasmid pMOD™-2(MCS) (Epicentre), previously linearized with XbaI. The resulting plasmids pXYTn5ATa and pXYTn5ATb only differ by the orientation of XbaI fragment and were used to prepare the Tn5AT cassette by digestion with PvuII according to the manufacturer's specification.

In Vitro Transposon Mutation and Selection of Mutagenized Fosmid pXYF24D3 and pXYF148D12

To generate a library of random mutagenized fosmids carrying segments of the enduracidin biosynthesis cluster for gene replacement studies, in vitro transposon insertional mutation studies of fosmids pXYF24 and pXYF148 were performed. Two putative enduracidin biosynthesis regulatory genes, orf18 and orf24, reside on the inserts of fosmids pXYF24 and pXYF148, respectively (GenBank accession no. DQ403252). The in vitro transposon reaction was performed at 37° C. for 2 hours after mixing 10 μL (0.5 μg) fosmid template DNA, 2 μL (20 ng) Tn5AT cassette DNA, 2 μL 10× reaction buffer, 1 μL Tn5 transposase and 5 μL sterile water. Transformation of *E. coli* competent cells EP1300™-$T1^R$(Epicentre) with the transposon reaction mixture was performed by electroporation. Mutagenized fosmids were selected on LB agar plates supplemented with 100 μg/mL apramycin. Plates were incubated overnight at 37° C. and surviving colonies were randomly picked and grown in LB liquid culture with addition of 100 μg/mL apramycin. The mutagenized fosmid DNA from these colonies and control fosmid pXYF24 or pXYF148 were digested with HindIII and analyzed by electrophoresis on 1% agarose gels. The Tn5AT cassette contains a single HindIII site that is useful when screening for single versus multiple disruption events over the fosmid insert. No HindIII sites are present in the fosmid inserts of pXYF24 or pXYF148, and only one HindIII site is present in the fosmid vector. Hence, digestion with HindIII readily identifies fosmids with a single insertion of Tn5AT by the presence of two bands in the gel. Colonies carrying mutagenized fosmids with a single transposon insertion were randomly selected and grown in LB liquid culture to permit fosmid isolation and identification of the disrupted gene. Screening was conducted by sequence analysis using the primer 5'-AAGGAGAAGAGCCTTCAGAAGGAA-3' (SEQ ID NO: 24), which corresponds to a region of the apramycin resistance gene. In this manner, fosmid pXYF24D3 and pXYF148D12 were found to have Tn5AT inserted into orf18 at the nucleotide position 26386 and orf24 at the nucleotide position 34333 (GenBank accession no. DQ403252), respectively.

Insertional Disruption of Orf18 and Orf24 in the Wild-Type *S. fungicidicus* ATCC 21013.

The gene replacement fosmids pXYF24D3 and pXYF148D12 were separately transformed into *E. coli* S17-1 by electroporation and then introduced into *S. fungicidicus* by intergeneric conjugation (Mazodier et al., *J. Bacteriology* 171: 3583-3585, 1989 which is hereby incorporated by reference in its entirety). Exconjugant colonies surviving apramycin selection were passed through three successive rounds of sporulation without antibiotic selection on ISP2 agar plates to create the stable mutant strain via double crossover homologous recombination. The resulting spores were pooled, diluted and plated on ISP2 agar plates supplemented with 50 μg/mL apramycin for confirmation of the apramycin resistance and for use in seed culture and enduracidin production fermentation. The mutant strain with the insertional disruption of orf18 in *S. fungicidicus* wild-type was designated SfpXYF24D3 and the mutant strain with the insertional disruption of orf24 in *S. fungicidicus* wild-type was designated SfpXYF148D12.

Production of Enduracidin in Laboratory Scale and in 10-Liter Fermenter.

Laboratory shake flask fermentation conditions for the production of enduracidin in *S. fungicidicus* wild-type, BM38-2 (ATCC PTA-122342) and derivative strains were as described by Higashide et al. (*J. Antibiotics,* 21: 126-137, 1968) except for the enduracidin production media which was disclosed in a patent (U.S. Pat. No. 4,465,771). For laboratory scale fermentation, 5 mL TSB was used for inoculation of the seed culture with freshly harvested streptomycete spores. Typically 5 to 10 mL of the seed culture incubated on a rotary shaker at 225 rpm and 30° C. for 48 hours and was then transferred to a 50 mL enduracidin production medium for 10 days continuous fermentation. Production of enduracidin by the wild-type and derivative strains under closely controlled conditions was also conducted in 10-liter automatic fermenters.

TABLE 2

Comparison of enduracidin (enramycin) yields in wild-type, mutant and genetically engineered strains of *Streptomyces fungicidicus*

| *S. fungicidicus* Strain | Fermentation Conditions | Yield (HPLC) |
|---|---|---|
| Wild-type (ATCC21013) | Shake flask | 5-30 mg/L |
| BM38-2 | Shake flask | 60-90 mg/L |
| SfpXY52endorf24 | Shake flask | 60 mg/L |
| SfpXYF24D3 | Shake flask | 40 mg/L |
| BM38-2.orf18pfrd-AmR | Shake flask | 67 mg/L |
| BM38-2.24/16 | Shake flask | 30-130 mg/L |
| BM38-2 | 10 L fermentor | 80-145 mg/L |
| BM38-2.24/16 | 10 L fermentor | 375 mg/L |

Extraction of Enduracidin from Fermentation Products for HPLC Analysis.

To extract the metabolites for HPLC analysis of enduracidin production, the fresh mycelia was harvested by centrifugation and washed with deionized water and re-suspended in 5× volume (ratio of the aqueous methanol (mL) to the wet mycelial weight (g)) 70% aqueous methanol (pH was adjusted to 3.5 with 1 N HCl). The suspension was shaken at 200 rpm at room temperature overnight and then centrifuged at 4000 rpm and 4° C. for 20 minutes. Then 1.4 mL of supernatant from each sample was transferred to individual 1.5 mL microcentrifuge tubes and centrifuged at 13,000 rpm at room temperature for 10 minutes. The filtrate was passed through a 0.22 μm syringe filter and then analyzed by HPLC. Metabolite extraction from mycelia produced in 10 L fermenters was conducted on a small scale equivalent to laboratory fermentations.

HPLC Analysis and Enduracidin Yield Determination.

A 50 μL HPLC sample prepared as describe above was injected onto a Gemini $C_{18}$ column (5 μm, 4.6×150 mm, Phenomenex, Torrance, CA) attached to a Shimadzu HPLC. Separation was achieved using an 18 min stepwise linear gradients with solvent A: water+0.1% TFA and solvent B: acetonitrile. The flow rate was 1 mL/minute starting with 10% B, increasing to 40% B over 10 min, and then further increasing to 95% B over 8 minutes. The UV region from 200 to 300 nm was scanned with a SPD M20A photodiode array detector. Yields of enduracidins were calculated by comparison with a standard curve constructed from a stock solution of enduracidin standards in 70% methanol. A series of injections including 2, 4, 6, 8, 10 and 12 μg of enduracidin was used to construct the standard curve using the sum of the absorbance areas for enduracidins A and B at 230 nm. A regression equation was generated from the standard curve and used to calculate enduracidin yields.

Evaluation of Antibacterial Activity.

*Staphylococcus aureus* (ATCC 29213) was used as an indicating microorganism in the bioassay. Cells were used to inoculate LB broth, grown at 37° C. overnight, and then 100 μL of the culture was mixed with 5 mL of the top agar (mixture of equal volumes of nutrient agar and nutrient broth). The top agar was overlaid onto a nutrient agar plate in which appropriately spaced wells were made by cutting out the agar plugs. Enduracidin standards and aliquots of culture extractions were dissolved or diluted in 50% MeOH at a concentration of 20 μg/mL, and 100 μL of each solution was loaded into the wells. After incubating the plates at 37° C. for 16 hours, the zones of inhibition were observed and compared, and the plates photographed or stored at 4° C.

Example 2

Disruption of Orf18 and Orf24 in Wild-Type *S. fungicidicus* and Effect on Enduracidin Production This example describes the disruption of orf18 and orf24 in wild-type *S. fungicidicus* and the effect on enduracidin production.

A 116,000 bp DNA sequence from the wild-type *S. fungicidicus* ATCC 21013 that harbors the enduracidin biosynthetic gene cluster and its flanking regions (U.S. Pat. No. 8,188,245 which is hereby incorporated by reference in its entirety) was previously identified and is available in GenBank (accession No. DQ403252). Among the 48 annotated orfs are eight putative regulatory genes: orf5, orf12, orf18, orf22, orf24, orf41, orf42 and orf43. To decipher the role of each of the gene products in enduracidin production, fosmid inserts carrying segments of the enduracidin cluster harboring these putative regulatory genes were randomly mutated using a transposon-mediated insertion of an apramycin resistance marker as described in Example 1.

The subsequent screening for apramycin resistance and insert location among *E. coli* colonies carrying mutagenized fosmids identified pXYF24D3 to carry the disrupted orf18 and pXYF148D12 to harbor the disrupted orf24. A single insertional mutation in each of these fosmids and the site of the insertion was confirmed by sequencing. These two mutagenized fosmids were then individually introduced by conjugation into the *S. fungicidicus* wild-type strain. Exconjugants showing apramycin resistance were then passed through three rounds of sporulation on ISP2 agar without addition of any antibiotic selection to promote conversion of the single crossover homologous recombination to double crossover mutation. The resulting stable mutant strains SfpXYF24D3 and SfpXYF148D12 were fermented in enduracidin production medium (EPM) on laboratory scale in shake flasks. HPLC analysis of the 70% methanol extraction of the mycelia from 10 days fermentation revealed an increase of 1.3-fold in enduracidin yield by the orf18-disrupted strain SfpXYF24D3 and the complete loss of enduracidin production by strain SfpXYF148D12 having a disrupted orf24. The mycelia extracts were also evaluated for activity towards *S. aureus*. The orf18 disruptant SfpXYF24D3 retained activity whereas the orf24 disruptant SfpXYF148D12 lost activity towards *S. aureus*.

Example 3

Construction of the Recombinant Strain SfpXY152-Endorf24 and Effect on Enduracidin Production This example describes the construction of the recombinant strain SfpXY152-endorf24 and the ability of this strain to produce enduracidin.

The loss of enduracidin production in the mutant strain SfpXYF148D12 indicated a possible regulatory role for orf24. A BLAST search of the GenBank database using the Orf24 protein sequence revealed high sequence similarity with a pathway-specific regulatory protein, StrR, involved in streptomycin biosynthesis. A sequence alignment between Orf24 and StrR showed the proteins share a significant similarity (54% aa identity, FIG. 9). The loss of enduracidin production upon orf24 disruption and the similarity with StrR indicate that Orf24 may act as a pathway-specific activator in enduracidin production.

To explore the role of orf24 as a positive regulatory target for strain improvement, the integrative expression plasmid pXY152-endorf24 (FIG. 2) was constructed (Example 1). Plasmid pXY152-endorf24 was introduced into wild-type *S. fungicidicus* by conjugation and exconjugants were screened for the apramycin resistance phenotype, leading to the identification of the new recombinant strain SfpXY152-endorf24. At least ten independent exconjugant colonies from this strain were randomly selected and purified. These colony strains carry the pXY152-endorf24 plasmid integrated into an attB site on the *S. fungicidicus* chromosome by single crossover homologous recombination with the attP site on the plasmid.

To investigate the metabolites produced by the recombinant strains, spores from two colony strains were inoculated into TSB seed culture and then transferred to enduracidin production medium for laboratory scale fermentation. HPLC analysis of the 70% methanol extracts of the harvested mycelia revealed a 2-fold increase (60 mg/L) in the enduracidin production by both recombinant strains compared to the wild-type strain (30 mg/L). The elevated yields of enduracidin observed in these colony strains that are capable of overexpressing orf24 is further evidence of the positive regulatory role this gene has in enduracidin production and the results are consistent with those obtained from the disruption of orf24 that led to the loss of enduracidin production.

Example 4

Construction of the Strain BM38-2.24/16 Overexpressing Orf24 in *S. fungicidicus* BM38-2 (ATCC PTA-122342) and Effect on Enduracidin Production This example describes construction of the strain BM38-2.24/16 (ATCC Deposit No. PTA-124006), overexpressing orf24 in *S. fungicidicus* BM38-2 (ATCC PTA-122342) and effect on enduracidin production.

To further explore the positive regulatory role of Orf24, plasmid pXY152-endorf24 was incorporated into the chromosome of the commercial production strain *S. fungicidicus* BM38-2 (ATCC PTA-122342), as described above for the wild-type organism. Selection of exconjugants exhibiting the apramycin resistance phenotype yielded a number of recombinant colony strains, including *S. fungicidicus* BM38-2.24/16, capable of producing elevated enduracidin levels up to 200 mg/L (for a 3.3-fold increase over BM38-2 (ATCC PTA-122342)) in laboratory shake flask cultures. *S. fungicidicus* BM38-2-24/16 was selected for further evaluation of enduracidin production capacity based on yields during the preliminary screening.

Enduracidin production by recombinant strain *S. fungicidicus* BM38-2.24/16 in laboratory shake flask cultures showed clear potential for significant improvement over BM38-2 (ATCC PTA-122342) and yields were also observed to vary greatly. To more closely control culture conditions over the 10 day growth period, including pH and dissolved oxygen that are not easily managed in shake flasks, production was evaluated through multiple runs in 10 L fermenters. Under these more closely controlled conditions, the yields were more consistent and triplicate 10 L fermentations averaged 375 mg/mL (4.6-fold of BM38-2 (ATCC PTA-122342)). The increased enduracidin yields in the recombinant strain S. *fungicidicus* BM38-2.24/16

(ATCC Deposit No. PTA-124006) further support a positive upregulation role of Orf24 in enduracidin production.

Example 5

Figure 5:
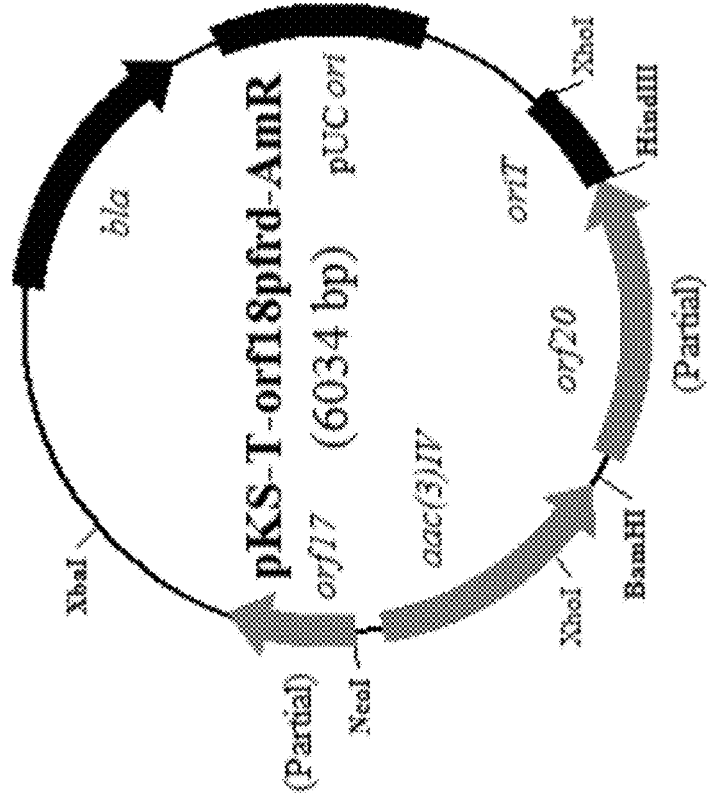
FIG. 5 is a map of the gene deletion plasmid pKS-T-orf18pfrd-AmR.
Figures 10A, 10B:
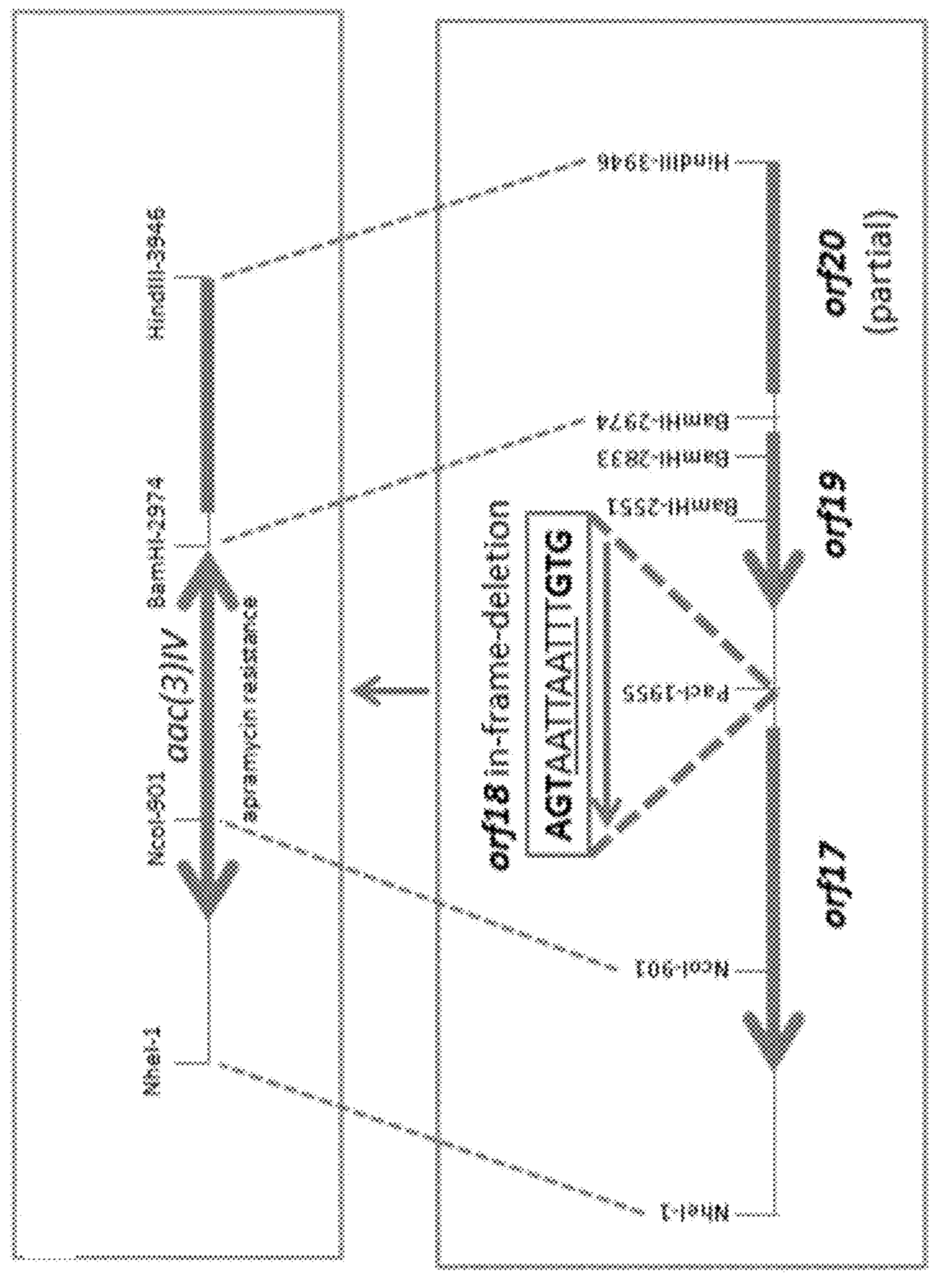
FIGS. 10A and 10B are maps of the inserts of plasmids pKS-T-orf18pfrd-AmR (a) and pXY300-orf18ifd (b). In the construct pXY30-orf18ifd, the internal sequence of orf18 from nucleotide position 25795 through 26450 (GenBank accession no. DQ403252) was deleted and replaced with a Pac restriction site (TTAATTAA, FIG. 10B). The resulting in-frame deleted orf18 (GTGTTTAATTAATGA (SEQ ID NO: 27)) could be translated into a three amino acid peptide (VFN). In general, any internal in-frame deletion over the length of orf18 should result in a nulled function of Orf18 due to its incompleteness.

Construction of the Deletion Mutant Strain BM38-1.18Pfrd-AmR and the Effect on Enduracidin Production This example describes construction of the deletion mutant strain BM38-2.18pfrd-AmR (ATCC Deposit No. PTA-124007) and the effect on enduracidin production.

orf18 is located in the upstream region of the enduracidin biosynthetic gene cluster (GenBank accession no. DQ403252). Orf18 appears to have a negative role in enduracidin production inasmuch as insertional disruption of the gene in the mutant strain SfpXYF24D3 elevated the yield of enduracidin. Based on this observation, constructs were designed for the deletion of orf18 alone and orf18 and portions of its flanking regions. For this purpose, plasmid pKS-T-orf18pfrd-AmR was constructed (FIG. 5). This pKS vector-derived plasmid possesses neither a streptomycete replicon nor an element for integration into the streptomycete chromosome. It can only exchange its insert with a defined segment of DNA in the host chromosome via double crossover homologous recombination. The insert map of this plasmid is shown in FIG. 10. orf18 and its flanking regions containing the entire orf19 and the region coding for the N-terminal portion of orf17 is deleted in plasmid pKS-T-orf18pfrd-AmR. The 1-kb left arm contains the region coding for the C-terminal portion of orf17 and its downstream region and the 1-kb right arm contains a partial segment of orf20 coding for the N-terminal region. Therefore the deletion after double crossover homologous recombination resulted in a recombinant strain where the entire orf18 plus orf19 and the region coding for the N-terminal portion of orf17 are deleted and replaced with the apramycin resistant gene.

Plasmid pKS-T-orf18pfrd-AmR was conjugally introduced into *S. fungicidicus* BM38-2 (ATCC PTA-122342) and single and double crossover homologous recombination was promoted on ISP4 agar plates without apramycin supplementation. Exconjugants that were able to survive subsequent apramycin selection were purified and this new recombinant strain was designated BM38-2.18pfrd-AmR (ATCC Deposit No. PTA-124007). Spores from this strain were inoculated into TSB medium for seed culture and then transferred into enduracidin production medium. After 10 days fermentation the mycelia were harvested, processed and analyzed by HPLC. Relative to the parent strain BM38-2 (ATCC PTA-122342), an increase of 1.2-fold in enduracidin production was observed from these laboratory scale fermentations. The relative increase in yield is similar to that observed with the wild-type derived strain SfpXYF24D3 and the results imply that orf19 and orf17, which flank orf18 and were affected in the construction of BM38-2.18pfrd-AmR, have little or no effect on enduracidin production. Therefore, the increased enduracidin production in the recombinant strain BM38-2.18pfrd-AmR is due to elimination of the negative regulatory role of Orf18.

Regarding the deletion of orf18 alone with the plasmid pXY300-orf18ifd in BM38-2 (ATCC PTA-122342), difficulties were encountered with positively selecting the exconjugants and single/double mutants with thiostrepton resistance marker. Therefore, alternative vector pBluescript KS II was used to construct the markerless gene replacement delivery plasmids such as pKS-T-orf18ifd (FIG. 4) or pKS-orf18ifd-T, pKS-orf18ifd-T-AmR(NS) (apramycin resistance gene is carried on the vector instead of insertion into orf18, see FIG. 6).

Example 6

Development of the pKS-Derived Gene Inactivation Vector pKS-T-orf18pfrd-AmR Series This example describes development of pKS-derived gene inactivation vector pKS-T-orf18pfrd-AmR series.

A series of pKS-derived gene inactivation vectors were developed (FIGS. 4, 5 and 6) that possess the conjugative function and do not require passing transformants through a high temperature selection to eliminate the plasmid as some other gene disruption vectors require. These pKS-derived vectors carry a non-streptomycete replicon allowing replication in *E. coli* and can maintain and be selected with the apramcyin resistance marker in *Streptomyces* and *E. coli* or ampicillin in *E. coli*. They produced copious stable copies of recombinant plasmids in *E. coli* for conjugation and they have been designed with several rare and unique restriction sites found in streptomycete DNA, such as PacI, HindIII, NheI, and XbaI, that can be conveniently used to assembly the target DNA into the plasmid for insertional gene disruption and in-frame-deletion studies.

Example 7

Development of pSET152-Derived Integrative Gene Expression Vectors pXY152-endorf24-camtsr and pXY152-endorf24-blatsr This example describes development of pSET152-derived integrative gene expression vectors pXY152-endorf24-camtsr (SEQ ID NO: 20) and pXY152-endorf24-blatsr (SEQ ID NO: 23).

Two new vectors, pXY152-endorf24-camtsr (FIG. 7) and pXY152-endorf24-blatsr (FIG. 8) were developed. They possess conjugative and integrative functions like vector pSET152, the most widely used integrative vector for streptomycete gene expression and complementation. Both these vectors carry several restriction sites that are rare in *Streptomyces* DNA for convenient cloning and assembly of the expression construct. Vector pXY152-endorf24-camtsr can be maintained and selected in *E. coli* with chloramphenicol at 12.5 μg/mL and in *Streptomyces* with thiostrepton at 50 μg/mL. Vector pXY152-endorf24-blatsr can be maintained and selected in *E. coli* with ampicillin and in *Streptomyces* with thiostrepton.

Summary of Examples 1-7

Genetic Manipulation of *Streptomyces* Regulatory and Biosynthesis Genes for Strain Improvement Among the numerous microbial producers of natural products, approximately 75% of the known microbial antibiotics are produced by actinomycetes. *Streptomyces*, Gram-positive filamentous soil bacteria, are members of the actinomycete family and are known for their unrivaled ability to produce a versatile array of structurally diverse, pharmacologically and biologically active secondary metabolites. Polyketides produced by polyketide synthases (PKS) and peptide natural products made by nonribosomal peptide synthetases (NRPS) are representatives.

Research on natural product antibiotic biosynthesis has some common challenges: first, how to overcome the typical low production of the parent or structurally modified compounds produced by the wild-type or genetically engineered strains; second, how to activate the many cryptic or orphan secondary metabolite biosynthetic pathways identified from genome sequences so the biological function of the products can be studied. Advances in the study of natural product antibiotic biosynthesis over the past decades have indicated that production of secondary metabolites is regulated by many pathways. For example, the precursor and structural assembly biosynthetic genes (such as PKS and NRPS), regulatory genes and self-resistance genes can be clustered on the bacterial chromosome. Antibiotic production may be regulated by pathway specific regulatory genes, including activators and/or repressors, pleiotropic ectopic regulatory genes, and two-component regulatory systems. Mutations occurring in any of these regulatory genes or systems may increase, decrease or completely abolish antibiotic production. Cryptic biosynthetic pathway can be activated by an unpredicted mutation leading to the production of a previously unknown product.

Strain improvement may play an important role in the cost effective industrial scale production of antibiotics or other microbial secondary metabolites. Mutant strains able to produce increased yields of particular metabolites can be generated through random mutations or by targeted disruption of specific genes or by the introduction of gene(s) that eliminate bottlenecks in a biosynthesis pathway. Genetic manipulation of positive and negative regulatory genes, as well as biosynthetic genes, to generate hyper-production of a targeted secondary metabolites has been proven to be a powerful and highly successful strategy of actinomycete strain improvement.

In the current disclosure, the positive regulatory role of orf24 and the negative regulatory role of orf18 on enduracidin production was demonstrated. Targeted insertional inactivation of orf24 resulted in a complete loss of enduracidin production in the recombinant strain SfpXYF148D12. Subsequent overexpression of orf24 under the control of the strong constitutive promoter ermE*p in the recombinant strains SfpXY152-endorf24 and BM38-2.24/16 led to increases in enduracidin yields of approximately 2 to 4.6-fold. The deletion of orf18 and its flanking regions, including the entire orf19 and a portion of orf17, increased enduracidin yields by 1.2-fold. These results provided strong genetic evidence in support of the roles of orf24 and orf18 as positive activator and negative repressor, respectively, in enduracidin biosynthesis.

Orf24 Orthologs have been Functionally Confirmed from Other Antibiotic Biosynthesis Pathways A BLAST query with Orf24 protein sequence against GenBank database revealed hundreds of hits (GenBank accession no. DQ403252). Many show very high amino acid similarity (from 60% to 99% identities) and are annotated as transcriptional regulators in the biosynthesis of the aminoglycoside antibiotic streptomycin. However, none of this group of genes has had the function verified experimentally. Analysis of the BLAST results identified several related proteins that share a lower similarity (over 40% but below 60% aa identity) to Orf24 that were functionally characterized. These include the well-characterized protein StrR which shares a lower but significant similarity (54% aa identities in 311 aa overlap) with Orf24. StrR has been genetically and biochemically demonstrated to function as a pathway specific positive activator of the expression of the streptomycin biosynthesis genes in *Streptomyces griseus*. StrR represents a family of pathway-specific activators, a handful of which have been characterized by either genetic manipulation or biochemical studies. FIG. 11 shows the alignment of Orf24 with six functionally confirmed actinomycete StrR-like proteins. A typical and highly conserved helix-turn-helix (HTH) DNA-binding domain is present in all seven proteins as underlined in FIG. 11. Orf24 also shares a significant sequence similarity (54% aa identities) to Teil15*, a pathway specific activator governing biosynthesis of the nonribosomally generated glycopeptide antibiotic teicoplanin. Teil5* positively regulates the transcription of at least 17 genes in the teicoplanin cluster. The wild-type *Actinoplanes teichomyceticus* produces about 100 mg/L of teicoplanin whereas the genetic recombinant strains, derived from the parent *A. teichomyceticus* and carrying tei15*expressed under the control of different promoters, increased teicoplanin yield to 1 g/L in the case of ermE*p promoter and to 4 g/L in the case of the native apramycin resistance gene promoter.

As illustrated in FIG. 11, Orf24 also shares a significant sequence similarity (54% aa identities) to Bbr, from the balhimycin glycopeptide antibiotic biosynthesis cluster; to KasT (50% aa identities) governing the expression of aminoglycoside antibiotic kasugamycin biosynthesis genes; and NovG (45% aa identities) the pathway specific activator involved in novobiocin biosynthesis. The ΔnovG mutant produced only 2% as much novobiocin as wild-type and overexpression of novG from a multi-copy plasmid in the recombinant strain led to a three-fold increase in the novobiocin production. Orf24 also shares 42% aa identities with SgcR1, one of four regulator genes (sgcR1, sgcR2, sgcR3 and sgcR) experimentally confirmed to be involved in production of the antitumor antibiotic C-1027 in *S. globisporus. Overexpression of sgc*R1 in *S. globisporus* SB1022 increased the C-1027 yield approximately seven-fold compared to the wild-type strain. Overexpression of the positive regulator sgcR3 in a recombinant strain resulted in a 30-40% increase in C-1027 production. In contrast, inactivation of the negative regulator sgcR led to increases both C-1027 and heptaene production. Moreover, overexpression of sgcR1 in the ΔsgcR mutant strain led to about a seven-fold increase of C-1027 production. sgcR3 occupies a higher level regulation by control of sgcR1 and sgcR2 in the hierarchy regulation of C-1027 production. In conclusion, the disruption and expression effects of orf24 and the comparison of Orf24 with other functionally characterized orthologs indicate Orf24 acts as a pathway specific positive regulator/activator in enduracidin production.

Orf18 is a Putative Atypical Orphan Response Regulator and Aligns with Functionally Confirmed Orthologs Production of antibiotics in *Streptomyces* species is tightly regulated by complex genetic networks that limit the ability of many wild-type antibiotic producers from generating yields necessary for large-scale, cost-effective industrial production. One important regulatory mechanism is the two-component signal transduction systems. Two-component systems include a sensor kinase and a cognate response regulator. The sensor kinase responds to specific external environmental stimuli/signals such as stress, nutrition and chemicals, etc., and then relays the signal to a cytoplasmic response regulator that triggers and activates the transcription of target genes. A response regulator that is unpaired with a sensor kinase is designated an orphan response regulator.

Two-component systems and orphan response regulators are present in streptomycete genomes and can function to repress secondary metabolite production. In the enduracidin gene cluster from *S. fungicidicus*, orf18 encodes a putative orphan response regulator that shares a low to moderate sequence similarity to three other characterized *Streptomyces* response regulators including one orphan response regulator, SC03818, from *S. coelicolor* (FIG. 12). Orf18 has a longer N-terminal sequence compared to the other aligned proteins and appears to be an atypical orphan response regulator because a highly conserved lysine at position 118 (relative to the common position 105) is absent in Orf18 and replaced with a threonine. The lysine is proposed to be required for forming the phosphorylation pocket.

Only a few streptomycete response regulators have been functionally characterized. The *S. coelicolor* genome contains a total of five atypical and seven typical orphan response regulators. Orf18 shares 26% aa identities in 191 aa overlap with AbsA2. The deletion of AbsA2 in *S. coelicolor* resulted in increased production of two antibiotics, actinorhodin and undecylprodigiosin. Orf18 shows 32% aa identities in 176 aa overlap with SC03818. Deletion of sco3818 led to enhanced production of actinorhodin. Orf18 shares 29% aa identities in 166 overlap aa with SCO1745 (AbrA2). Deletion of the AbrA2-containing-response regulator operon resulted in 100% increase of the antitumor antibiotic oviedomycin in the recombinant strain *S. coelicolor* M145 compared to the wild-type producer. The observed negative regulatory role of Orf18 in enduracidin production is consistent with the demonstrated activities of the related negative regulators (FIG. 12). In addition, it is noticed that Orf18 shares the highest protein sequence similarity with the members of the LuxR family of transcriptional regulators in the BLAST search.

Absence of Polar Effects in the Mutant BM38-1.orf18pfrd-AmR

The deleted region in the mutant BM38-1.18pfrd-AmR strain involves three genes, orf18, the region coding for the N-terminal portion of or17 located downstream of orf18, and the entire orf19 located upstream of orf18 (FIGS. 5 and 10). orf17 is predicted to encode a ribonuclease apparently having no function related to the biosynthesis or regulation of enduracidin. Also, the apramycin resistance gene replacing orf18 and its flanking region is transcribed divergently with orf17 and should not create any read-through events from the apramycin resistance gene promoter. Therefore, there should be no polar effects resulting from the partial deletion of orf17.

orf19 is transcribed and translated in the same direction as orf18. This gene is annotated to encode a protein of unknown function. The mutant strain SfpXYF24D3 carrying the disruption of orf18 alone and the mutant BM38-1.18pfrd-AmR carrying the deletion of orf18 and orf19 together have similarly enhanced effects on enduracidin production which implies orf19 has no role or a negligible role in enduracidin production. The gene orf20 is located upstream of orf19 and transcribed and translated in the same direction as the inserted apramycin resistance marker (FIG. 10) orf20 is still intact in BM38-1.18pfrd-AmR and the product apparently does not have a role in enduracidin production. Therefore any polar effects on the expression of orf20 are not believed to be responsible for the enhanced enduracidin production in BM38-1.18pfrd-AmR.

Example 8

Further Applications and Manipulations of Orf24 and/or Orf18 for Enhanced Enduracidin Producing Strains In addition to the examples provided above, there are other possible ways to utilize the regulatory roles of orf24 and orf18 to improve the enduracidin production.

i. Expression of Orf24 Under an Alternative, Constitutive or Inducible Overexpression Promoter pXY152-endorf24 (shown in FIG. 2) was constructed for the integrative ectopic expression of orf24 under the control of ermE*p, a widely used streptomycete strong constitutive expression promoter. The overexpression of orf24 may also be driven by other constitutive or inducible promoters. The tipA promoter is a thiostrepton inducible overexpression streptomycete promoter. A multicopy tipA promoter-containing *E. coli-Streptomyces* shuttle plasmid, pXY200, was developed that has been successfully used for overexpression of streptomycete genes. For applications relevant to this disclosure, the tipA promoter can be excised from pXY200 and cloned into pXY152 to replace ermE*p and drive the expression of orf24. Likewise, orf24 can be easily transferred from pXY152-endorf24 to pXY200 for plasmid-based expression. Other promoter options include, but are not limited to, the P(nitA)-NitR system and the streptomycete promoter SF14. Recently, the integrative plasmid pKC1139 and the native promoter of the apramycin resistant gene were successfully used to express regulatory genes for hyperproduction of the peptide antibiotic teicoplanin. The regulatory gene sanG encodes a pathway specific activator for nikkomycin production. The expression of an extra copy of sanG under the control of five different promoters ($P_{hrdB}$, $P_{tcp830}$, $P_{SF14}$, $P_{ermE*}$ and Pneos) led to increases in nikkomycin yields by 69%, 51%, 26%, 22%, and 13%, respectively (see Du et al., Applied Microbiology and Biotechnology 97: 6383-6396, 2013).

ii. Double Mutant Strains of *S. fungicidicus* with Deletion of Orf18 and Overexpression of Orf24

With both the orf18 deletion mutant and the orf24 overexpression strains exhibiting increased enduracidin production, a double mutant containing both can be generated and whether an additive effect on the yield of this peptide antibiotic is observed. The double mutant can be created by introducing the overexpression plasmid pXY152-endorf24-blatsr (FIG. 8) into the mutant BM38-2.18pfrd-AmR. pXY152-endorf24-blatsr is a conjugal integrative plasmid carrying a thiostrepton resistance gene (tsr) for selection in streptomycetes and ampicillin resistance gene (bla) for selection in *E. coli*. Because the *E. coli* strain S17-1 used for conjugation is naturally resistant to chloramphenicol (cam), the chloramphenicol resistance marker in pXY152-endorf24-camtsr (see above) has been replaced with ampicillin resistance (bla) in order to select S17-1 transformants. Alternatively, pXY152-endorf24-camtsr and derivatives can be introduced into streptomycetes by using a different conjugal *E. coli* strain, ET12567/pUZ8002.

Using either plasmid pXY152-endorf24-blatsr or pXY152-endorf24-camtsr to introduce the second copy of orf24 into the orf18 deficient mutant, it is possible to select for the double mutant by thiostrepton resistance. To generate a null orf18 in-frame-deletion mutant in BM38-2 (ATCC PTA-122342), plasmids pXY300-orf18ifd (FIG. 3) and pKS-orf18ifd-T-AmR(NS) (FIG. 6) were constructed for this purpose. pXY300-orf18ifd allows for selection of the orf18 in-frame deletion mutant with thiostrepton while pKS-orf18ifd-T-AmR(NS) uses apramycin to select in-frame deletion mutants. Although mutant strains of wild-type *S. fungicidicus* are readily selected using the thiostrepton resistance marker, difficulties have been encountered using this resistance marker in the BM38-2 (ATCC PTA-122342) strain. Thus, two plasmids, pXY300-orf18ifd and pKS-orf18ifd-T-AmR(NS), were constructed for the same purpose.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A recombinant strain of *Streptomyces fungicidicus*, comprising an augmented open reading frame-24 (orf24) that encodes the amino acid sequence of SEQ ID NO: 26 or a diminished open reading frame-18 (orf18), wherein an enhanced production of enduracidin is obtained with the recombinant strain of *Streptomyces fungicidicus* in comparison to that obtained with a control strain of *Streptomyces fungicidicus*.

2. The recombinant strain of claim 1, wherein the diminished orf18 is diminished because it has been nulled.

3. The recombinant strain of claim 2, wherein the diminished orf18 has been nulled by a process comprising an in-frame-deletion, a frame-shift mutation, a point mutation, or a combination thereof.

4. The recombinant strain of claim 2, wherein the diminished orf18 has been nulled by an in-frame deletion.

5. The recombinant strain of claim 1, wherein the augmented orf24 is operatively linked to a heterologous promoter.

6. The recombinant strain of claim 5, wherein the heterologous promoter is a strong constitutive promoter.

7. The recombinant strain of claim 5, wherein the heterologous promoter comprises an ermE*p promoter, a tipA promoter, or a SF14 promoter.

8. The recombinant strain of claim 1, wherein the augmented ORF24 is augmented because it has been overexpressed.

9. The recombinant strain of claim 1, wherein the control strain is *Streptomyces fungicidicus* ATCC 21013.

10. The recombinant strain of claim 1, wherein the control strain is *Streptomyces fungicidicus* ATCC PTA-122342.

11. The recombinant strain of claim 1, wherein the production of enduracidin by the recombinant strain is at least 1.2-fold greater than the production of enduracidin by the control strain.

12. The recombinant strain of claim 11, wherein the production of enduracidin by the recombinant strain is 1.2- to 4.6-fold greater than the production of enduracidin by the control strain.

13. The recombinant strain of claim 1 that is BM38-2.18pfrd-AmR (ATCC Deposit No. PTA-124007).

14. An expression vector comprising an augmented open reading frame orf24 (SEQ ID NO: 38).

15. The expression vector of claim 14, wherein the augmented orf24 is operatively linked to a heterologous promoter.

16. The expression vector of claim 15, wherein the heterologous promoter is a strong constitutive promoter.

17. The expression vector of claim 15, wherein t the heterologous promoter comprises an ermE*p promoter, a tipA promoter, or a SF14 promoter.

18. A disruption vector comprising an open reading frame orf18 (SEQ ID NO: 37) which has been nulled.

19. The disruption vector of claim 18, wherein the orf18 has been nulled by an in-frame deletion, a frame-shift mutation, a point mutation, or a combination thereof.

20. The disruption vector of claim 19, wherein the orf18 has been nulled by an in-frame deletion.

21. The disruption vector of claim 18, wherein the disruption vector is selected from pXY300-orf18ifd (SEQ ID NO: 8), pKS-T-orf18ifd (SEQ ID NO: 11), pKS-T-orf18pfrd-AmR (SEQ ID NO: 14), and pKS-orf18ifd-T-AmR(NS)(SEQ ID NO: 19).

* * * * *

SEQUENCE LISTING

```
Sequence total quantity: 40
SEQ ID NO: 1             moltype = DNA  length = 31
FEATURE                  Location/Qualifiers
misc_feature             1..31
                         note = Synthetic oligonucleotide primer
source                   1..31
                         mol_type = other DNA
                         organism = synthetic construct
SEQUENCE: 1
ccaccacata tggaaataag ttcgctctcc a                                 31

SEQ ID NO: 2             moltype = DNA  length = 32
FEATURE                  Location/Qualifiers
misc_feature             1..32
                         note = Synthetic oligonucleotide primer
source                   1..32
                         mol_type = other DNA
                         organism = synthetic construct
SEQUENCE: 2
gtgtgtgaat tcctcgttca cccggccaga tg                                32

SEQ ID NO: 3             moltype = DNA  length = 6210
FEATURE                  Location/Qualifiers
misc_feature             1..6210
                         note = Synthetic plasmid pXY152-endorf24
source                   1..6210
                         mol_type = other DNA
                         organism = synthetic construct
SEQUENCE: 3
gaattcgtaa tcatgtcata gctgtttcct gtgtgaaatt gttatccgct cacaattcca  60
cacaacatac gagccggaag cataaagtgt aaagcctggg gtgcctaatg agtgagctaa  120
ctcacattaa ttgcgttgcg ctcactgccc gctttccagt cgggaaacct gtcgtgccag  180
ctgcattaat gaatcggcca acgcgcgggg agaggcggtt tgcgtattgg gcgctcttcc  240
gcttcctcgc tcactgactc gctgcgctcg gtcgttcggc tgcggcgagc ggtatcagct  300
cactcaaagg cggtaatacg gttatccaca gaatcagggg ataacgcagg aaagaacatg  360
tgagcaaaag gccagcaaaa ggccaggaac cgtaaaaagg ccgcgttgct ggcgtttttc  420
cataggctcc gcccccctga cgagcatcac aaaaatcgac gctcaagtca gaggtggcga  480
aacccgacag gactataaag ataccaggcg tttccccctg gaagctccct cgtgcgctct  540
cctgttccga ccctgccgct taccggatac ctgtccgcct ttctcccttc gggaagcgtg  600
gcgctttctc atagctcacg ctgtaggtat ctcagttcgg tgtaggtcgt tcgctccaag  660
ctgggctgtg tgcacgaacc ccccgttcag cccgaccgct gcgccttatc cggtaactat  720
cgtcttgagt ccaacccggt aagacacgac ttatcgccac tggcagcagc cactggtaac  780
aggattagca gagcgaggta tgtaggcggt gctacagagt tcttgaagtg gtggcctaac  840
tacggctaca ctagaagaac agtatttggt atctgcgctc tgctgaagcc agttaccttc  900
ggaaaaagag ttggtagctc ttgatccggc aaacaaacca ccgctggtag cggtggtttt  960
tttgtttgca agcagcagat tacgcgcaga aaaaaaggat ctcaagaaga tcctttgatc  1020
ttttctacgg ggtctgacgc tcagtggaac gaaaactcac gttaagggat tttggtcatg  1080
agattatcaa aaaggatctt cacctagatc cttttggttc atgtgcagct ccatcagcaa  1140
aaggggatga taagtttatc accaccgact atttgcaaca gtgccgttga tcgtgctatg  1200
atcgactgat gtcatcagcg gtggagtgca atgtcgtgca atacgaatgg cgaaaagccg  1260
agctcatcgg tcagcttctc aaccttgggg ttaccccccgg cggtgtgctg ctggtccaca  1320
gctccttccg tagcgtccgg cccctcgaag atgggccact tggactgatc gaggccctgc  1380
gtgctgcgct gggtccggga gggacgctcg tcatgccctc gtggtcaggt ctggacgacg  1440
agccgttcga tcctgccacg tcgcccgtta caccggacct tggagttgtc tctgacacat  1500
tctggcgcct gccaaatgta aagcgcagcg cccatccatt tgcctttgcg gcagcggggc  1560
cacaggcaga gcagatcatc tctgatccat tgcccctgcc acctcactcg cctgcaagcc  1620
cggtcgcccg tgtccatgaa ctcgatgggc aggtacttct cctcggcgtg ggacacgatg  1680
ccaacacgac gctgcatctt gccgagttga tggcaaaggt tccctatggg gtgccgagac  1740
actgcaccat tcttcaggat ggcaagttgg tacgcgtcga ttatctcgag aatgaccact  1800
gctgtgagcg ctttgccttg gcggacaggt ggctcaagga gaagagcctt cagaaggaag  1860
gtccagtcgg tcatgccttt gctcggttga tccgctcccg cgacattgtg gcgacagccc  1920
tgggtcaact gggccgagat ccgttgatct tcctgcatcc gccagaggcg ggatgcgaag  1980
aatgcgatgc cgctcgccag tcgattggct gagctcatga gcggagaacg agatgacgtt  2040
ggaggggcaa ggtcgcgctg attgctgggg caacacgtgg agcggatcgg ggattgtctt  2100
tcttcagctc gctgatgata tgctgacgct caatgccgtt tggcctccga ctaacgaaaa  2160
tcccgcattt ggacggctga tccgattggc acggcggacg gcgaatggcg gagcagacgc  2220
tcgtccgggg gcaatgagat atgaaaaagc ctgaactcac cgcgacgtat cgggccctgg  2280
ccagctagct agagtcgacc tgcaggtccc cggggatcgg tcttgccttg ctcgtcggtg  2340
atgtacttca ccagctccgc gaagtcgctc ttcttgatgg agcgcatggg gacgtgcttg  2400
gcaatcacgc gcaccccccg gccgttttag cggctaaaaa agtcatggct ctgccctcgg  2460
gcggaccacg cccatcatga ccttgccaag ctcgtcctgc ttctcttcga tcttcgccag  2520
cagggcgagg atcgtggcat caccgaaccg cgccgtgcgc gggtcgtcgg tgagccagag  2580
```

-continued tttcagcagg ccgcccaggc ggcccaggtc gccattgatg cgggccagct cgcggacgtg 2640
ctcatagtcc acgacgcccg tgattttgta gccctggccg acggccagca ggtaggccga 2700
caggctcatg ccggccgccg ccgcctttc ctcaatcgct cttcgttcgt ctggaaggca 2760
gtacaccttg ataggtgggc tgcccttcct ggttggcttg gtttcatcag ccatccgctt 2820
gccctcatct gttacgccgg cggtagccgg ccagcctcgc agagcaggat tcccgttgag 2880
caccgccagg tgcgaataag ggacagtgaa gaaggaacac ccgctcgcgg gtgggcctac 2940
ttcacctatc ctgcccggct gacgccgttg gatacaccaa ggaaagtcta cacgaaccct 3000
ttggcaaaat cctgtatatc gtgcgaaaaa ggatggatat accgaaaaaa tcgctataat 3060
gaccccgaag cagggttatg cagcggaaaa gatccgtcga cctgcaggca tgcaagctct 3120
agcgattcca gacgtcccga aggcgtggcg cggcttcccc gtgccggagc aatcgccctg 3180
ggtgggttac acgacgcccc tctatggccc gtactgacgg acacaccgaa gccccggcgg 3240
caaccctcag cggatgcccc ggggcttcac gttttcccag gtcagaagcg gttttcggga 3300
gtagtgcccc aactggggta acctttgagt tctctcagtt gggggcgtag ggtcgccgac 3360
atgacacaag ggttgtgac cggggtggac acgtacgcgg gtgcttacga ccgtcagtcg 3420
cgcgagcgcg agaactcgag cgcagcaagc ccagcgacac agcgtagcgc caacgaagac 3480
aaggcggccg accttcagcg cgaagtcgag cgcgacgggg gccggttcag gttcgtcggg 3540
catttcagcg aagcgccggg cacgtcggcg ttcgggacgg cggagcgccc ggagttcgaa 3600
cgcatcctga acgaatgccg cgccgggcgg ctcaacatga tcattgtcta tgacgtgtcg 3660
cgcttctcgc gcctgaaggt catggacgcg attccgattg tctcggaatt gctcgccctg 3720
ggcgtgacga ttgtttccac tcaggaaggc gtcttccggc agggaaacgt catggacctg 3780
attcacctga ttatgcggct cgacgcgtcg cacaaagaat cttcgctgaa gtcggcgaag 3840
attctcgaca cgaagaacct tcagcgcgaa ttgggcgggt acgtcggcgg gaaggcgcct 3900
tacggcttcg agcttgtttc ggagacgaag gagatcacgc gcaacggccg aatggtcaat 3960
gtcgtcatca acaagcttgc gcactcgacc actcccctta ccggaccctt cgagttcgag 4020
cccgacgtaa tccggtggtg gtggcgtgag atcaagacgc acaaacacct tcccttcaag 4080
ccgggcagtc aagccgccat tcacccgggc agcatcacgg ggctttgtaa gcgcatggac 4140
gctgacgccg tgccgacccg gggcgagacg attgggaaga agaccgcttc aagcgcctgg 4200
gacccggcaa ccgttatgcg aatccttcgg gacccgcgta ttgcgggctt cgccgctgag 4260
gtgatctaca agaagaagcc ggacggcacg ccgaccacga agattgaggg ttaccgcatt 4320
cagcgcgacc cgatcacgct ccggccggtc gagcttgatt gcggaccgat catcgagccc 4380
gctgagtggt atgagcttca ggcgtggttg gacggcaggg ggcgcggcaa ggggctttcc 4440
cgggggcaag ccattctgtc cgccatggac aagctgtact gcgagtgtgg cgccgtcatg 4500
acttcgaagc gcggggaaga atcgatcaag gactcttacc gctgccgtcg ccggaaggtg 4560
gtcgacccgt ccgcacctgg gcagcacgaa ggcacgtgca acgtcagcat ggcggcactc 4620
gacaagttcg ttgcggaacg catcttcaac aagatcaggc acgccgaagg cgacgaagag 4680
acgttggcgc ttctgtggga agccgcccga cgcttcggca agctcactga ggcgcctgag 4740
aagagcggcg aacgggcgaa ccttgttgcg gagcgcgccg acgccctgaa cgcccttgaa 4800
gagctgtacg aagaccgcgc ggcaggcgcg tacgacggac ccgttggcag gaagcacttc 4860
cggaagcaac aggcagcgct gacgctccgg cagcaagggg cggaagagcg gcttgccgaa 4920
cttgaagccg ccgaagcccc gaagcttccc cttgaccaat ggttccccga agacgccgac 4980
gctgacccga ccggccctaa gtcgtggtgg gggcgcgcgt cagtagacga caagcgcgtg 5040
ttcgtcgggc tcttcgtaga caagatcgtt gtcacgaagt cgactacggg caggggggcag 5100
ggaacgccca tcgagaagcg cgcttcgatc acgtgggcga agccgccgac cgacgacgac 5160
gaagacgacg cccaggacgg cacggaagac gtagcggcgt aggtgagtga agatctagac 5220
gtggcaccgc gatgctgttg tgggcacaat cgtgccggtt ggtaggatcc acatatggaa 5280
ataagttcgc tctccaccga cggctccccg cggatcgacg gggagagtcc cgagcacgtg 5340
gaaatgctgg ccgccgccga caccgcgctt ccaccgatca tggtgcaccg ccgcaccggg 5400
cgggtcatcg acggcatgca ccggctgcgc gccgcgatgc tgacgggccg tacgacgatc 5460
gcggtgaggt tcttcgacgg caccgaggag gacgccttcg tcctcgccgt gaagtcgaac 5520
atcgcgcacg gactgccgct gtccgccgcc gaccgccggc gggccgccgg gcgcatcatg 5580
gccacccatc cccggtggtc ggaccggatg atcgcctcgg tggtcggcac ctccgccagg 5640
acggtcgccg agatccgccg cgacgccggc gccgccgggg cgggggagcc cacccgcatc 5700
ggccgggacg gcagggtacg gcccgtcgac gtgagcgagg gccgcagact ggcccacgac 5760
atgatcgtcc gcgacccggg cctgtcgctg cgccaggtcg cccgcgccgc cgggatctcg 5820
ccggagaccg tcagggacgt cagacaccgg atgctccgcg gtgaggaccc ggtgcccgcg 5880
ccgcggccgc ggaccctggt ggagcgcggc gcggaccgcc gggcggagcc ggccgggaag 5940
gccgccgcgc cgtgcgggac ggagccgccg cccgccgtcg tgatgaagcg gctgagggcc 6000
gatccggcgc tgcgtctcaa cgagaacgga cgcgacctgc tgcggcttct ggatatccac 6060
acggtccggc tggaggactg gaaccgcatt atcgaaagcg tgccgccgca ccgtctggag 6120
acggtggcgc agctggcacg ctcctgcgcc gacaaatggt ccgagatcgc gtcacgcatc 6180
gaaagcaacg catcacatct ggccgggtga 6210

SEQ ID NO: 4 moltype = DNA length = 38
FEATURE Location/Qualifiers
misc_feature 1..38
note = Synthetic oligonucleotide primer
source 1..38
mol_type = other DNA
organism = synthetic construct
SEQUENCE: 4
ttattgaagc ttgccggggc cgacgcggcg ggcggcct 38

SEQ ID NO: 5 moltype = DNA length = 34
FEATURE Location/Qualifiers
misc_feature 1..34
note = Synthetic oligonucleotide primer
source 1..34
mol_type = other DNA
organism = synthetic construct

```
SEQUENCE: 5
gttgttttaa ttaaacacca ggcctcctgg ggtg                           34

SEQ ID NO: 6            moltype = DNA  length = 38
FEATURE                 Location/Qualifiers
misc_feature            1..38
                        note = Synthetic oligonucleotide primer
source                  1..38
                        mol_type = other DNA
                        organism = synthetic construct
SEQUENCE: 6
tttatattaa ttaatgaccc ttccgtcccg cccccgat                       38

SEQ ID NO: 7            moltype = DNA  length = 30
FEATURE                 Location/Qualifiers
misc_feature            1..30
                        note = Synthetic oligonucleotide primer
source                  1..30
                        mol_type = other DNA
                        organism = synthetic construct
SEQUENCE: 7
tttggtgcta gctggtcgtg gcgctgttcc                                30

SEQ ID NO: 8            moltype = DNA  length = 10670
FEATURE                 Location/Qualifiers
misc_feature            1..10670
                        note = Synthetic plasmid pXY300-orf18ifd
source                  1..10670
                        mol_type = other DNA
                        organism = synthetic construct
SEQUENCE: 8
ccgcggctcc tgcccgccga acgcgtcgtc gtcgacggcc tggtgctcat cgacgagcac  60
ccggagccag gtgaaaagcg ccggcggacg ctcggactgg gcgcgggatt ccagcagtaa  120
cccaggtccg ccggccacct cacggcaggc agaccctcgg ctttcgcgcc gggaccgcca  180
tgagaccgcc acccggatgt ccggggtggc ggtctcatgg cggtccctca gcggccctac  240
gcgaccgctg tgtcgacgcg gaggcagtct ccggggagcc ggccccaggg ctggagtacc  300
ggggcgagct tgcccttgca gcggcggcac acgggcgacg cggcgccggg cgggggagtc  360
ttgacgtcga cggtgaccgg cttcggcttc aggcgcttcc gaaggctgat cgtcgggcgg  420
atcgcctcct tcttcggctg acgcactcgg tcgagcgaag cggccagctc ctccgtgcgg  480
gcctcgttgg ccttccggcg cgcctcgcgg aaagcagctt cctcctcgga catgacctcg  540
aacctcatct ggtcagcgtc aaggtcgccc ggcgcggccg gcgcttccgg ggcgggcggg  600
tccaggacgt ccttgcccca caccaggccc caggactcga cgagccgccg gacgcccggt  660
aggccgtacg tctcggcgac cttgatgagg tcgaggtcga ggcgacgtcc ggcgacgcgg  720
gcgatgtatc ggtaccagat gtaggccggg atgaccgcga tggcgaccag gccctcggtg  780
tcgtcggtga tctcctcctc ggtgcggacg tcctgctgga tgccgagttc cttgatcagc  840
cggttcaggt tctgcgaccg gtagtgcttg cggacctgga agacgccgaa ctcgcgctcg  900
cggtacttct cgacgaacgg gccgggccga cgaagccgct gcagctcggc ggccgccgcg  960
tcgcccaggt cgagcggtcc catgcggtcg tcgccgcgac cggccttgaa gttctgtccg  1020
gccagctcca ggccgatctt ggcgacgccg cccttggtct tgtcgccgtc cttgtagagg  1080
tagcgggcct gcttgcccgc atcgccgtca gcggcgtccg cgccgttgag tgggcgcacg  1140
tcggtgccgt ggcccttgcc ctcacaggag caaccgggcc ggtcgcacgt ctcgctgacg  1200
gtgtagccgc ccgcggattc gaccccggcg gcccaggctc cggcgagtgc gtcgcggaac  1260
gcctgggcgt ccgggccgag cacctcgcgg gtgacccaga gcgtgtgcca gtgcaggtgc  1320
cagccggagc cccagccgaa ggtgtcctcg aaggcccgct cgtagccgat gatcccgaag  1380
tcgtcgcgca tcgtgcgcac gcggcggccg gacgagccgt acgcgccctt ccagccgtcg  1440
tgcaagaccg cgaccaggcc gtgccgcatt cccttgcgga cggtgccgaa cgccatgcgc  1500
tcgaagtggc gcaacgtgtt cgtgccaagg tgcagcccgt acccggcgtc cgcgagaccg  1560
tcggcggcga gctgcacgtt cgagccccgt acggccagga tgcggctcat gcaccacggg  1620
caggtgtgga cgttgttgca gcggcacgtg ttgccccacg tcgcctcgcc cggcttccac  1680
atcagctcgc ggtccggcag tgagccgggt cccgcagccc ttgaacgcct cgttcagcga  1740
caccgtctgg tgccggtccc gccgggcgaa ccgctcgtcg cggcgggtcc tcccgcccgc  1800
tgtcgcggca ccctcgtttg ggtagaaccc cgttccagtt acagcgctct gacctgcagt  1860
ggacggagat tttcccttac tactaaagcc cgcgtccgga ttacccgctg tagtcgtgct  1920
tgctacgctg cgtgactggt ccgcaatgag acgctttgcg cgctttcggc aggcgtccga  1980
gcagtagatt ttggggcgct tcccggggat gtggacgatc ggggtgccgc agtggcactt  2040
cggtccggcg gggcgcggtg gtgtcgacgc gctgttctct cgtacgcctc gtcacagagc  2100
aaacgtcctc actcggcatg ctgcgccggt tcgggggcgg cgagccggga ggccaatccc  2160
gggctcgtgc catttctggg tcctgttgat catcactgac gaatcgaggt cgaggaaccg  2220
agcgtccgag gaacagaggc gcttatcggt tggccgcgag attcctgtcg atcctctcgt  2280
gcagcgcgat tccgagggaa acggaaacgt tgagagactc ggtctggctc atcatgggga  2340
tggaaaccga ggcggaagac gcctcctcga acaggtcgga aggcccaccc ttttcgctgc  2400
cgaacagcaa ggccagccga tccggattgt ccccgagttc cttcacggaa atgtcgccat  2460
ccgccttgag cgtcatcagc tgcataccgc tgtcccgaat gaaggcgatg gcctcctcgc  2520
gaccggagag aacgacggga agggagaaga cgtaacctcg gctggccctt tggagacgcc  2580
ggtccgcgat gctggtgatg tcactgtcga ccaggatgat ccccgacgct ccgagcgcga  2640
gcgacgtgcg tactatcgcg ccgatgttcc cgacgatctt caccccgtcg agaacgacga  2700
cgtccccacg ccggctcgcg atatcgccga acctggccgg gcgagggacg cgggcgatgc  2760
cgaatgtctt ggccttccgc tccccttga acaactggtt gacgatcgag gagtcgatga  2820
ggcggaccgg tatgttctgc cgcccgcaca gatccagcaa ctcagatgga aaaggactgc  2880
```

-continued

```
tgtcgctgcc gtagacctcg atgaactcca ccccggccgc gatgctgtgc atgaggggct  2940
cgacgtcctc gatcaacgtt gtctttatgt tggatcgcga cggcttggtg acatcgatga  3000
tccgctgcac cgcgggatcg gacggatttg cgatggtgtc caactcagtc atggtcgtcc  3060
taccggctgc tgtgttcagt gacgcgattc ctggggtgtg acaccctacg cgacgatggc  3120
ggatggctgc cctgaccggc aatcaccaac gcaaggggaa gtcgtcgctc tctggcaaag  3180
ctccccgctc ttccccgtcc gggacccgcg cggtcgatcc ccgcatatgg tgcactctca  3240
gtacaatctg ctctgatgcc gcatagttaa gccagccccg acacccgcca acacccgctg  3300
acgcgccctg acgggcttgt ctgctcccgg catccgctta cagacaagct gtgaccgtct  3360
ccgggagctg catgtgtcag aggttttcac cgtcatcacc gaaacgcgcg agacgaaagg  3420
gcctcgtgat acgcctattt ttataggtta atgtcatgat aataatggtt tcttagacgt  3480
caggtggcac ttttcgggga aatgtgcgcg gaacccctat ttgtttattt ttctaaatac  3540
attcaaatat gtatccgctc atgagacaat aaccctgata aatgcttcaa taatattgaa  3600
aaaggaagag tatgagtatt caacatttcc gtgtcgccct tattcccttt tttgcggcat  3660
tttgccttcc tgtttttgct cacccagaaa cgctggtgaa agtaaaagat gctgaagatc  3720
agttgggtgc acgagtgggt tacatcgaac tggatctcaa cagcggtaag atccttgaga  3780
gttttcgccc cgaagaacgt tttccaatga tgagcacttt taaagttctg ctatgtggcg  3840
cggtattatc ccgtattgac gccgggcaag agcaactcgg tcgccgcata cactattctc  3900
agaatgactt ggttgagtac tcaccagtca cagaaaagca tcttacggat ggcatgacag  3960
taagagaatt atgcagtgct gccataacca tgagtgataa cactgcggcc aacttacttc  4020
tgacaacgat cggaggaccg aaggagctaa ccgctttttt gcacaacatg ggggatcatg  4080
taactcgcct tgatcgttgg gaaccggagc tgaatgaagc cataccaaac gacgagcgtg  4140
acaccacgat gcctgtagca atggcaacaa cgttgcgcaa actattaact ggcgaactac  4200
ttactctagc ttcccggcaa caattaatag actggatgga ggcggataaa gttgcaggac  4260
cacttctgcg ctcggccctt ccggctggct ggtttattgc tgataaatct ggagccggtg  4320
agcgtgggtc tcgcggtatc attgcagcac tggggccaga tggtaagccc tcccgtatcg  4380
tagttatcta cacgacgggg agtcaggcaa ctatggatga acgaaataga cagatcgctg  4440
agataggtgc ctcactgatt aagcattggt aactgtcaga ccaagtttac tcatatatac  4500
tttagattga tttaaaactt catttttaat ttaaaaggat ctaggtgaag atcctttttg  4560
ataatctcat gaccaaaatc ccttaacgtg agttttcgtt ccactgagcg tcagaccccg  4620
tagaaaagat caaaggatct tcttgagatc cttttttttct gcgcgtaatc tgctgcttgc  4680
aaacaaaaaa accaccgcta ccagcggtgg tttgtttgcc ggatcaagag ctaccaactc  4740
tttttccgaa ggtaactggc ttcagcagag cgcagatacc aaatactgtc cttctagtgt  4800
agccgtagtt aggccaccac ttcaagaact ctgtagcacc gcctacatac ctcgctctgc  4860
taatcctgtt accagtggct gctgccagtg gcgataagtc gtgtcttacc gggttggact  4920
caagacgata gttaccggat aaggcgcagc ggtcgggctg aacggggggt tcgtgcacac  4980
agcccagctt ggagcgaacg acctacaccg aactgagata cctacagcgt gagctatgag  5040
aaagcgccac gcttcccgaa gggagaaagg cggacaggta tccggtaagc ggcagggtcg  5100
gaacaggaga gcgcacgagg gagcttccag ggggaaacgc ctggtatctt tatagtcctg  5160
tcgggtttcg ccacctctga cttgagcgtc gatttttgtg atgctcgtca ggggggcgga  5220
gcctatggaa aaacgccagc aacgcggcct ttttacggtt cctggccttt tgctggcctt  5280
ttgctcacat gttctttcct gcgttatccc ctgattctgt ggataaccgt attaccgcct  5340
ttgagtgagc tgataccgct cgccgcagcc gaacgaccga gcgcagcgag tcagtgagcg  5400
aggaagcgga agagcgccca atacgcaaac cgcctctccc cgcgcgttgg ccgattcatt  5460
aatgcagctg gcacgacagg tttcccgact ggaaagcggg cagtgagcgc aacgcaatta  5520
atgtgagtta gctcactcat taggcacccc aggctttaca ctttatgctt ccggctcgta  5580
tgttgtgtgg aattgtgagc ggataacaat ttcacacagg aaacagctat gaccatgatt  5640
acgccaagct tgccggggcc gacgcggcgg gcggcctcgt ccatcgggac gcgccagtcg  5700
acgccgacga tgtccgcgcc ggcctcgccc atgagcccca gcagctcgcc ggtgccgacg  5760
ccgaagtgga tgcgcgggac gccgtggccg gccaccgcgc ggaacacctt cgccgaggcg  5820
ggcagcaccg aacgccggta gtcggagggg gcgagcgcgc cggcccagga gtcgaagagc  5880
tgcacggccg aggcgccggc ccggatctgg acgtcgagga aggccgccgt gatgtcggcg  5940
aggcggtcga gcaggtcggc ccagagctcg gggtcgccgt acatcatcgc cttggcgttc  6000
tcgtacgtac gggacgggcc gccctcgacg aggtaactcg caagggtgaa cggggcgccc  6060
gcgaaaccga tcagcggggt ggacccgagc tcacgggtca gcatgccgat ggcctcggtg  6120
acgtaggaga cgtcctccgg ggtcaggtcg cgcagccggg cgaggtcggc gcgggtgcgc  6180
accggctgct cgacgaccgg gccgatgccg ggcttgatgt cgaggtcgat gccgatggcc  6240
ttgagcggga cgacgatgtc gctgaagtag atcgccgcgt cgacgtggtg gcggcgcacc  6300
ggctggaggg tgatctcggt gaccagctcg ggccgcatgc aggagtcgag catcccgatg  6360
ccctcgcgca ccttgcggta ctccggcagt gagcgcccgg cctgccgcat gaaccacacc  6420
ggcgtgtgcg gcaccggctc gcgccggcac gccttgagga aggctgattc ccggacggcg  6480
tcgttcttga cggggtcggg ggtcgcggta ggcgtctggc ccttcgggct cgtgttggca  6540
ctcacaccgg ccagtctcgc acgacccgtc cgccgccccg gaccccaggg gcgtccggcg  6600
ggcggggccg cggtgcagga tccggacagc gccgggcggc gcgggtgtcc ctccctgcgc  6660
cgggggcccg ttccgcttaa tcttcccggc atggctgcgg ctcagggacg actgtcggac  6720
ggcgctggcg gaatggacga accgaaggag ggcggggggg atcccgggca cggaggtgcg  6780
cctccgccgc ccttccgggc cgctgtcgag gcgctgcaga gcgcccggct gcggccgcag  6840
atcgaggtgg agacggtgcc cgcgccgaaa cggctcgccc cgtacgcgca cgcgctggag  6900
gcggcggtcg tcgacggcga ggaggatctg gccgacggcc ggctggtgct gctgtgcgac  6960
ccggccggac acgacgcctg gcgggggacc ttccgtctgg tgacgctggt gcgcgccgag  7020
ctggagccgg agatggcggc ggatccgctg ctgccggacg tgtgctggtc ctggctgacc  7080
ggcgcgctgg cggcgcgcgg cctgtcgtac ggcgagccga gcggcacggt gacgcgggcg  7140
agttcgcact acttcggcgg gctgtccgcg cggcccgccg cctcccagat cgagatccgt  7200
gcctcgtgga cgccgcgtga gggtctgggc ggggttccgg acacggccgc ccatctggtc  7260
gcgtggtccg atctgctggc gcaggtcgcg gggctgccgc cggccgctcc gggggacgcg  7320
tccgtggtga cgctgccgca gcggaggggg ccgcagtcgc gctgagcctc ccgctgcggg  7380
gtcccgacga ccggcctcct gcatctctct ttgtcgatac ggccactttc ggaagcgttg  7440
cgacgcagac cgaaaccgtt cgatcttcga atgatcgatc gtgcgtccga attgcccgga  7500
ttgttactca tcacttcgtg atcattcgtt aaaggacacc aggtttgctg ccgaagacga  7560
ctgtgacctt gaaagcacgg ttcgtcccgc cttcaccccc acgagccggc ccgtcccgca  7620
```

```
ccccaggagg cctggtgttt aattaatgac ccttccgtcc cgccccccgat ccgcccgtcc  7680
ccgatccgcc cgcccacggc caagcgaaca cgttctttca ctcttctgac cggaatacga  7740
cccaccggcg cccgtcacgg agcacaaccg tcgacgggcg ccttcgcggc acggataccc  7800
ttgacaggtg accgacgccc acgacaccgc agcagacagt tcactgcgca ccaccggagg  7860
cgctcctccg gacgacggcg gatcttctgt tacggaggcg ccgacccccct tgctggaacc  7920
ccgcgagggc attccgcccg tgatagcgga cgaggccgcc ctcgccgagg cggtcgccgc  7980
cttcgcggcc ggcagcggac ccgtcgccgt ggacgccgag cgcgcctccg ggtaccgcta  8040
cggccagcgc gcctacctcg tccagctgcg ccgcgagggt gcgggtaccg cgctgatcga  8100
ccccgtggcc tgccccgacc tgtccgccct cggcgaggcg ctgtccggcg tcgagtgggt  8160
gctgcacgcc gccacccagg acctgccctg tctgcgcgag ataggcatgg tgccctcccg  8220
cctcttcgac accgagctgg ccggccgcct tgccgggttc cccgcgtcg ggctcggcgc  8280
gatggtcgag aacgtgctcg gcttcgtcct ggagaagggc cactccgccg tcgactggtc  8340
cacccgtccg ctgcccgagc cctggctgcg gtacgccgcc ctcgacgtcg aactgctggt  8400
cgatctgcgg gacgccctgg agaaggagct ggaccgccag ggcaagctgg actgggcccg  8460
gcaggagttc gacgcgatcg cctcggcccc gccgccggag ccccgcaagg acccctggcg  8520
ccgcacctcc ggcatgcaca aggtgcgccg gcgccgccag atggcggtgg tgcgggagct  8580
gtgggagacc cgcgaccgga tcgcccggcg ccgtgacgtc tcccccggca aggtgctttc  8640
cgacgcggcg atcgtggagg ccgcgctcgc gctgcccgcc aacctgcacg ccatggccgc  8700
gctcaacggg ttcgggcagc gggtggggcg gcgccagctg gagcagtggc aggcggccgt  8760
cgaccgcgcg aaggcgctga gcgaggccca gctgccgcag cccggccagc cggtgaccgg  8820
ccctccgccg ccgcgcgcct gggcggacaa ggaccccgtt gccgcggccc ggctgtcggc  8880
ggcccgcgcg ggggtcgccg aactcgccga gcggctgaac atgccgccgg agaacctgat  8940
caccccggac acggtgcgca gggtctgctg ggagccgccg gggcccgacg agcggtccgt  9000
cgccgcggcg ctgacggcgc acggggcacg cgcgtggcag gtcgaccagg tcactcccgt  9060
gctggtggcc gcgctggcta cttcgtcgcc ccccgcatga acccgttgta gatgaagcgc  9120
tggaggaaca ggaagacgat caaggtgggc aggatgacca ggaccgcgcc cgccgagatc  9180
gtctcccagt gcgcgccgaa ggggcccttg aagcggaaca gggacgtcga gatgaccccc  9240
aggtcctcgg agggcatgta gaggaagggg atgtagaagt cgttgtagac gttgatcccc  9300
tttacgatca ccaccgtcgc gatcgccggc ttgagcagcg ggaagatcac cttgcggtag  9360
acggtgaacg cgttggcgcc gtccaggcgc gccgcctcgt ccagggagac ggggatggag  9420
cggatgaact gcaggaagac gtagatcgag acgatgtccg tgcccatgta gagggcgatc  9480
ggcgcccaca ggctgtcgaa catgccgaag ctgttgacga tctggaaggt cgccacctgg  9540
gtggtcaccc cggggaccag cgcggccagc aggaacagcg ccacgaccag ctagcgaatt  9600
cctgcaggtc ccggggatc ggtcttgcct tgctcgtcgg tgatgtactt caccagctcc  9660
gcgaagtcgc tcttcttgat ggagcgcatg gggacgtgct tggcaatcac gcgcaccccc  9720
cggccgtttt agcggctaaa aaagtcatgg ctctgccctc gggcggacca cgcccatcat  9780
gaccttgcca agctcgtcct gcttctcttc gatcttcgcc agcagggcga ggatcgtggc  9840
atcaccgaac cgcgccgtgc gcgggtcgtc ggtgagccag agtttcagca ggccgcccag  9900
gcggcccagg tcgccattga tgcgggccag ctcgcggacg tgctcatagt ccacgacgcc  9960
cgtgattttg tagccctggc cgacggccag caggtaggcc gacaggctca tgccggccgc  10020
cgccgccttt tcctcaatcg ctcttcgttc gtctggaagg cagtacacct tgataggtgg  10080
gctgcccttc ctggttggct tggtttcatc agccatccgc ttgccctcat ctgttacgcc  10140
ggcggtagcc ggccagcctc gcagagcagg attcccgttg agcaccgcca ggtgcgaata  10200
agggacagtg aagaaggaac acccgctcgc gggtgggcct acttcaccta tcctgcccgg  10260
ctgacgccgt tggatacacc aaggaaagtc tacacgaacc ctttggcaaa atcctgtata  10320
tcgtgcgaaa aaggatggat ataccgaaaa aatcgctata atgaccccga agcagggtta  10380
tgcagcggaa aagatccgtc gacctgcagc ccgggggatc cccgggtacc gagctcgggc  10440
tggggctcgg ggccgccggt gagctggtag acgaaggcgc ccgagtctcc ttcgttcact  10500
gcgtgccact cgtggtgcgg gtacttccgg cgcaacgtgc tgtcgtccat gggcggcatc  10560
atggcagagg cggagacgcc gttccgcgcc tttcgtcggg gcccgtaggg tttcggacat  10620
tcttgtgcgg ggtggggggg cgccggcgga cccggtgcgc ccggcgtcgc             10670
```

```
SEQ ID NO: 9            moltype = DNA  length = 40
FEATURE                 Location/Qualifiers
misc_feature            1..40
                        note = Synthetic oligonucleotide primer
source                  1..40
                        mol_type = other DNA
                        organism = synthetic construct
SEQUENCE: 9
agcacagcta gcttctagaa gcttcattca aaggccggca                        40

SEQ ID NO: 10           moltype = DNA  length = 43
FEATURE                 Location/Qualifiers
misc_feature            1..43
                        note = Synthetic oligonucleotide primer
source                  1..43
                        mol_type = other DNA
                        organism = synthetic construct
SEQUENCE: 10
gccagtgaat tctgcagctc gagcagagca ggattcccgt tga                    43

SEQ ID NO: 11           moltype = DNA  length = 7173
FEATURE                 Location/Qualifiers
misc_feature            1..7173
                        note = Synthetic plasmid pKS-T-orf18pfrd
source                  1..7173
                        mol_type = other DNA
                        organism = synthetic construct
```

```
SEQUENCE: 11
gtggcacttt tcggggaaat gtgcgcggaa cccctatttg tttatttttc taaatacatt  60
caaatatgta tccgctcatg agacaataac cctgataaat gcttcaataa tattgaaaaa  120
ggaagagtat gagtattcaa catttccgtg tcgcccttat tccctttttt gcggcatttt  180
gccttcctgt ttttgctcac ccagaaacgc tggtgaaagt aaaagatgct gaagatcagt  240
tgggtgcacg agtgggttac atcgaactgg atctcaacag cggtaagatc cttgagagtt  300
ttcgccccga agaacgtttt ccaatgatga gcacttttaa agttctgcta tgtggcgcgg  360
tattatcccg tattgacgcc gggcaagagc aactcggtcg ccgcatacac tattctcaga  420
atgacttggt tgagtactca ccagtcacag aaaagcatct tacggatggc atgacagtaa  480
gagaattatg cagtgctgcc ataaccatga gtgataacac tgcggccaac ttacttctga  540
caacgatcgg aggaccgaag gagctaaccg cttttttgca caacatgggg gatcatgtaa  600
ctcgccttga tcgttgggaa ccggagctga atgaagccat accaaacgac gagcgtgaca  660
ccacgatgcc tgtagcaatg gcaacaacgt tgcgcaaact attaactggc gaactactta  720
ctctagcttc ccggcaacaa ttaatagact ggatggaggc ggataaagtt gcaggaccac  780
ttctgcgctc ggcccttccg gctggctggt ttattgctga taaatctgga gccggtgagc  840
gtgggtctcg cggtatcatt gcagcactgg ggccagatgg taagccctcc cgtatcgtag  900
ttatctacac gacggggagt caggcaacta tggatgaacg aaatagacag atcgctgaga  960
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt tttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatggaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaatttc acacaggaaa cagctatgac catgattacg  2160
ccaagcgcgc aattaaccct cactaaaggg aacaaaagct gggtaccggg ccccccctcg  2220
agcagagcag gattcccgtt gagcaccgcc aggtgcgaat aagggacagt gaagaaggaa  2280
cacccgctcg cgggtgggcc tacttcacct atcctgcccg gctgacgccg ttggatacac  2340
caaggaaagt ctacacgaac cctttggcaa aatcctgtat atcgtgcgaa aaaggatgga  2400
tataccgaaa aaatcgctat aatgaccccg aagcagggtt atgcagcgga aaatgcagct  2460
cacggtaact gatgccgtat ttgcagtacc agcgtacggc ccacagaatg atgtcacgct  2520
gaaaatgccg gcctttgaat gaagcttgcc ggggccgacg cggcgggcgg cctcgtccat  2580
cgggacgcgc cagtcgacgc cgacgatgtc cgcgccggcc tcgcccatga gccccagcag  2640
ctcgccggtg ccgacgccga agtggatgcg cgggacgccg tggccggcca ccgcgcggaa  2700
caccttcgcc gaggcgggca gcaccgaacg ccggtagtcg gagggggcga gcgcgccggc  2760
ccaggagtcg aagagctgca cggccgaggc gccggcccgg atctggacgt cgaggaaggc  2820
cgccgtgatg tcggcgaggc ggtcgagcag gtcggcccag agctcggggt cgccgtacat  2880
catcgccttg gcgttctcgt acgtacggga cgggccgccc tcgacgaggt aactcgcaag  2940
ggtgaacggg gcgcccgcga aaccgatcag cggggtggac ccgagctcac gggtcagcat  3000
gccgatggcc tcggtgacgt aggagacgtc ctccggggtc aggtcgcgca gccgggcgag  3060
gtcggcgcgg gtgcgcaccg gctgctcgac gaccgggccg atgccgggct tgatgtcgag  3120
gtcgatgccg atggccttga gcgggacgac gatgtcgctg aagtagatcg ccgcgtcgac  3180
gtggtggcgg cgcaccggct ggagggtgat ctcggtgacc agctcgggcc gcatgcagga  3240
gtcgagcatc ccgatgccct cgcgcacctt gcggtactcc ggcagtgagc gcccggcctg  3300
ccgcatgaac cacaccggcg tgtgcggcac cggctcgcgc cggcacgcct tgaggaaggc  3360
tgattcccgg acggcgtcgt tcttgacggg gtcgggggtc gcggtaggcg tctggccctt  3420
cgggctcgtg ttggcactca caccggccag tctcgcacga cccgtccgcc gccccggacc  3480
ccaggggcgt ccggcgggcg gggccgcggt gcaggatccg gacagcgccg ggcggcgcgg  3540
gtgtccctcc ctgcgccggg ggcccgttcc gcttaatctt cccggcatgg ctgcggctca  3600
gggacgactg tcggacggcg ctggcggaat ggacgaaccg aaggagggcg ggggggatcc  3660
cgggcacgga ggtgcgcctc cgccgccctt ccgggccgct gtcgaggcgc tgcagagcgc  3720
ccggctgcgg ccgcagatcg aggtggagac ggtgcccgcg ccgaaacggc tcgccccgta  3780
cgcgcacgcg ctggaggcgg cggtcgtcga cggcgaggag gatctggccg acggccggct  3840
ggtgctgctg tgcgacccgg ccggacacga cgcctggcgg gggaccttcc gtctggtgac  3900
gctggtgcgc gccgagctgg agccggagat ggcggcggat ccgctgctgc cggacgtgtg  3960
ctggtcctgg ctgaccggcg cgctggcggc gcgcggcctg tcgtacggcg agccgagcgg  4020
cacggtgacg cgggcgagtt cgcactactt cggcgggctg tccgcgcggc ccgccgcctc  4080
ccagatcgag atccgtgcct cgtggacgcc gcgtgagggt ctgggcgggg ttccggacac  4140
ggccgcccat ctggtcgcgt ggtccgatct gctggcgcag gtcgcggggc tgccgccggc  4200
cgctccgggg gacgcgtccg tggtgacgct gccgcagcgg agggggccgc agtcgcgctg  4260
agcctcccgc tgcggggtcc cgacgaccgg cctcctgcat ctctctttgt cgatacggcc  4320
actttcggaa gcgttgcgac gcagaccgaa accgttcgat cttcgaatga tcgatcgtgc  4380
gtccgaattg cccggattgt tactcatcac ttcgtgatca ttcgttaaag gacaccaggt  4440
ttgctgccga agacgactgt gaccttgaaa gcacggttcg tcccgccttc acccccacga  4500
gccggcccgt cccgcacccc aggaggcctg gtgtttaatt aatgaccctt ccgtcccgcc  4560
cccgatccgc ccgtccccga tccgcccgcc cacggccaag cgaacacgtt ctttcactct  4620
tctgaccgga atacgaccca ccggcgcccg tcacggagca caaccgtcga cgggcgcctt  4680
```

```
cgcggcacgg atacccttga caggtgaccg acgcccacga caccgcagca gacagttcac  4740
tgcgcaccac cggaggcgct cctccggacg acggcggatc ttctgttacg gaggcgccga  4800
cccccttgct ggaaccccgc gagggcattc cgcccgtgat agcggacgag gccgccctcg  4860
ccgaggcggt cgccgccttc gcggccggca gcggacccgt cgccgtggac gccgagcgcg  4920
cctccgggta ccgctacggc cagcgcgcct acctcgtcca gctgcgccgc gagggtgcgg  4980
gtaccgcgct gatcgacccc gtggcctgcc ccgacctgtc cgccctcggc gaggcgctgt  5040
ccggcgtcga gtgggtgctg cacgccgcca cccaggacct gccctgtctg cgcgagatag  5100
gcatggtgcc ctcccgcctc ttcgacaccg agctggccgg ccgccttgcc gggttccccc  5160
gcgtcgggct cggcgcgatg gtcgagaacg tgctcggctt cgtcctggag aagggccact  5220
ccgccgtcga ctggtccacc cgtccgctgc ccgagccctg gctgcggtac gccgccctcg  5280
acgtcgaact gctggtcgat ctgcgggacg ccctggagaa ggagctggac cgccagggca  5340
agctggactg ggcccggcag gagttcgacg cgatcgcctc ggccccgccg ccggagcccc  5400
gcaaggaccc ctggcgccgc acctccggca tgcacaaggt gcgccggcgc cgccagatgg  5460
cggtggtgcg ggagctgtgg gagacccgcg accggatcgc ccggcgccgt gacgtctccc  5520
ccggcaaggt gctttccgac gcggcgatcg tggaggccgc gctcgcgctg cccgccaacc  5580
tgcacgccat ggccgcgctc aacgggttcg ggcagcgggt ggggcggcgc cagctggagc  5640
agtggcaggc ggccgtcgac cgcgcgaagg cgctgagcga ggcccagctg ccgcagcccg  5700
gccagccggt gaccggccct ccgccgccgc gcgcctgggc ggacaaggac cccgttgccg  5760
cggcccggct gtcggcggcc cgcgcggggg tcgccgaact cgccgagcgg ctgaacatgc  5820
cgccggagaa cctgatcacc ccggacacgg tgcgcagggt ctgctgggag ccgccggggc  5880
ccgacgagcg gtccgtcgcc gcggcgctga cggcgcacgg ggcacgcgcg tggcaggtcg  5940
accaggtcac tcccgtgctg gtggccgcgc tggctacttc gtcgcccccc gcatgaaccc  6000
gttgtagatg aagcgctgga ggaacaggaa gacgatcaag gtgggcagga tgaccaggac  6060
cgcgcccgcc gagatcgtct cccagtgcgc gccgaagggg cccttgaagc ggaacaggga  6120
cgtcgagatg acccccaggt cctcggaggg catgtagagg aaggggatgt agaagtcgtt  6180
gtagacgttg atccccttta cgatcaccac cgtcgcgatc gccggcttga gcagcgggaa  6240
gatcaccttg cggtagacgg tgaacgcgtt ggcgccgtcc aggcgcgccg cctcgtccag  6300
ggagacgggg atggagcgga tgaactgcag gaagacgtag atcgagacga tgtccgtgcc  6360
catgtagagg gcgatcggcg cccacaggct gtcgaacatg ccgaagctgt tgacgatctg  6420
gaaggtcgcc acctgggtgg tcaccccggg gaccagcgcg gccagcagga acagcgccac  6480
gaccagctag ttctagagcg gccgccaccg cggtggagct ccaattcgcc ctatagtgag  6540
tcgtattacg cgcgctcact ggccgtcgtt ttacaacgtc gtgactggga aaaccctggc  6600
gttacccaac ttaatcgcct tgcagcacat ccccctttcg ccagctggcg taatagcgaa  6660
gaggcccgca ccgatcgccc ttcccaacag ttgcgcagcc tgaatggcga atggaaattg  6720
taagcgttaa tattttgtta aaattcgcgt taaatttttg ttaaatcagc tcatttttta  6780
accaataggc cgaaatcggc aaaatccctt ataaatcaaa agaatagacc gagatagggt  6840
tgagtgttgt tccagtttgg aacaagagtc cactattaaa gaacgtggac tccaacgtca  6900
aagggcgaaa aaccgtctat cagggcgatg gcccactacg tgaaccatca ccctaatcaa  6960
gtttttttggg gtcgaggtgc cgtaaagcac taaatcggaa ccctaaaggg agcccccgat  7020
ttagagcttg acggggaaag ccggcgaacg tggcgagaaa ggaagggaag aaagcgaaag  7080
gagcgggcgc tagggcgctg gcaagtgtag cggtcacgct gcgcgtaacc accacacccg  7140
ccgcgcttaa tgcgccgcta cagggcgcgt cag                              7173
```

```
SEQ ID NO: 12          moltype = DNA  length = 29
FEATURE                Location/Qualifiers
misc_feature           1..29
                       note = Synthetic oligonucleotide primer
source                 1..29
                       mol_type = other DNA
                       organism = synthetic construct
SEQUENCE: 12
gaatggccat ggttcatgtg cagctccat                                   29

SEQ ID NO: 13          moltype = DNA  length = 30
FEATURE                Location/Qualifiers
misc_feature           1..30
                       note = Synthetic oligonucleotide primer
source                 1..30
                       mol_type = other DNA
                       organism = synthetic construct
SEQUENCE: 13
tctcgaggat ccgaatagga acttcggaat                                  30

SEQ ID NO: 14          moltype = DNA  length = 6034
FEATURE                Location/Qualifiers
misc_feature           1..6034
                       note = Synthetic plasmid pKS-T-orf18pfrd-AmR
source                 1..6034
                       mol_type = other DNA
                       organism = synthetic construct
SEQUENCE: 14
gtggcacttt tcggggaaat gtgcgcggaa cccctatttg tttatttttc taaatacatt  60
caaatatgta tccgctcatg agacaataac cctgataaat gcttcaataa tattgaaaaa  120
ggaagagtat gagtattcaa catttccgtg tcgcccttat tccctttttt gcggcatttt  180
gccttcctgt ttttgctcac ccagaaacgc tggtgaaagt aaaagatgct gaagatcagt  240
tgggtgcacg agtgggttac atcgaactgg atctcaacag cggtaagatc cttgagagtt  300
ttcgccccga agaacgtttt ccaatgatga gcacttttaa agttctgcta tgtggcgcgg  360
tattatcccg tattgacgcc gggcaagagc aactcggtcg ccgcatacac tattctcaga  420
atgacttggt tgagtactca ccagtcacag aaaagcatct tacggatggc atgacagtaa  480
```

-continued

```
gagaattatg cagtgctgcc ataaccatga gtgataacac tgcggccaac ttacttctga  540
caacgatcgg aggaccgaag gagctaaccg cttttttgca caacatgggg gatcatgtaa  600
ctcgccttga tcgttgggaa ccggagctga atgaagccat accaaacgac gagcgtgaca  660
ccacgatgcc tgtagcaatg gcaacaacgt tgcgcaaact attaactggc gaactactta  720
ctctagcttc ccggcaacaa ttaatagact ggatggaggc ggataaagtt gcaggaccac  780
ttctgcgctc ggcccttccg gctggctggt ttattgctga taaatctgga gccggtgagc  840
gtgggtctcg cggtatcatt gcagcactgg ggccagatgg taagccctcc cgtatcgtag  900
ttatctacac gacggggagt caggcaacta tggatgaacg aaatagacag atcgctgaga  960
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt tttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatggaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaatttc acacaggaaa cagctatgac catgattacg  2160
ccaagcgcgc aattaaccct cactaaaggg aacaaaagct gggtaccggg ccccccctcg  2220
agcagagcag gattcccgtt gagcaccgcc aggtgcgaat aagggacagt gaagaaggaa  2280
cacccgctcg cgggtgggcc tacttcacct atcctgcccg gctgacgccg ttggatacac  2340
caaggaaagt ctacacgaac cctttggcaa aatcctgtat atcgtgcgaa aaaggatgga  2400
tataccgaaa aaatcgctat aatgaccccg aagcagggtt atgcagcgga aaatgcagct  2460
cacggtaact gatgccgtat ttgcagtacc agcgtacggc ccacagaatg atgtcacgct  2520
gaaaatgccg gcctttgaat gaagcttgcc ggggccgacg cggcgggcgg cctcgtccat  2580
cgggacgcgc cagtcgacgc cgacgatgtc cgcgccggcc tcgcccatga gccccagcag  2640
ctcgccggtg ccgacgccga agtggatgcg cgggacgccg tggccggcca ccgcgcggaa  2700
caccttcgcc gaggcgggca gcaccgaacg ccggtagtcg gagggggcga gcgcgccggc  2760
ccaggagtcg aagagctgca cggccgaggc gccggcccgg atctggacgt cgaggaaggc  2820
cgccgtgatg tcggcgaggc ggtcgagcag gtcggcccag agctcggggt cgccgtacat  2880
catcgccttg gcgttctcgt acgtacggga cgggccgccc tcgacgaggt aactcgcaag  2940
ggtgaacggg gcgcccgcga aaccgatcag cggggtggac ccgagctcac gggtcagcat  3000
gccgatggcc tcggtgacgt aggagacgtc ctccggggtc aggtcgcgca gccgggcgag  3060
gtcggcgcgg gtgcgcaccg gctgctcgac gaccgggccg atgccgggct tgatgtcgag  3120
gtcgatgccg atggccttga gcgggacgac gatgtcgctg aagtagatcg ccgcgtcgac  3180
gtggtggcgg cgcaccggct ggagggtgat ctcggtgacc agctcgggcc gcatgcagga  3240
gtcgagcatc ccgatgccct cgcgcacctt gcggtactcc ggcagtgagc gcccggcctg  3300
ccgcatgaac cacaccggcg tgtgcggcac cggctcgcgc cggcacgcct tgaggaaggc  3360
tgattcccgg acggcgtcgt tcttgacggg gtcgggggtc gcggtaggcg tctggccctt  3420
cgggctcgtg ttggcactca caccggccag tctcgcacga cccgtccgcc gccccggacc  3480
ccaggggcgt ccggcgggcg gggccgcggt gcaggatccg aataggaact tcggaatagg  3540
aacttcatga gctcagccaa tcgactggcg agcggcatcg cattcttcgc atcccgcctc  3600
tggcggatgc aggaagatca acggatctcg gcccagttga cccagggctg tcgccacaat  3660
gtcgcgggag cggatcaacc gagcaaaggc atgaccgact ggaccttcct tctgaaggct  3720
cttctccttg agccacctgt ccgccaaggc aaagcgctca cagcagtggt cattctcgag  3780
ataatcgacg cgtaccaact tgccatcctg aagaatggtg cagtgtctcg gcaccccata  3840
gggaaccttt gccatcaact cggcaagatg cagcgtcgtg ttggcatcgt gtcccacgcc  3900
gaggagaagt acctgcccat cgagttcatg gacacgggcg accgggcttg caggcgagtg  3960
aggtggcagg ggcaatggat cagagatgat ctgctctgcc tgtggccccg ctgccgcaaa  4020
ggcaaatgga tgggcgctgc gctttacatt tggcaggcgc cagaatgtgt cagagacaac  4080
tccaaggtcc ggtgtaacgg gcgacgtggc aggatcgaac ggctcgtcgt ccagacctga  4140
ccacgagggc atgacgagcg tccctcccgg acccagcgca gcacgcaggg cctcgatcag  4200
tccaagtggc ccatcttcga ggggccggac gctacggaag gagctgtgga ccagcagcac  4260
accgccgggg gtaaccccaa ggttgagaag ctgaccgatg agctcggctt ttcgccattc  4320
gtattgcacg acattgcact ccaccgctga tgacatcagt cgatcatagc acgatcaacg  4380
gcactgttgc aaatagtcgg tggtgataaa cttatcatcc ccttttgctg atggagctgc  4440
acatgaacca tggccgcgct caacgggttc gggcagcggg tggggcggcg ccagctggag  4500
cagtggcagg cggccgtcga ccgcgcgaag gcgctgagcg aggcccagct gccgcagccc  4560
ggccagccgg tgaccggccc tccgccgccg cgcgcctggg cggacaagga ccccgttgcc  4620
gcggcccggc tgtcggcggc ccgcgcgggg gtcgccgaac tcgccgagcg gctgaacatg  4680
ccgccggaga acctgatcac cccggacacg gtgcgcaggg tctgctggga gccgccgggg  4740
cccgacgagc ggtccgtcgc cgcggcgctg acggcgcacg gggcacgcgc gtggcaggtc  4800
gaccaggtca ctcccgtgct ggtggccgcg ctggctactt cgtcgccccc cgcatgaacc  4860
cgttgtagat gaagcgctgg aggaacagga agacgatcaa ggtgggcagg atgaccagga  4920
ccgcgcccgc cgagatcgtc tcccagtgcg cgccgaaggg gcccttgaag cggaacaggg  4980
acgtcgagat gacccccagg tcctcggagg gcatgtagag gaaggggatg tagaagtcgt  5040
tgtagacgtt gatccccttt acgatcacca ccgtcgcgat cgccggcttg agcagcggga  5100
agatcacctt gcggtagacg gtgaacgcgt tggcgccgtc caggcgcgcc gcctcgtcca  5160
gggagacggg gatggagcgg atgaactgca ggaagacgta gatcgagacg atgtccgtgc  5220
```

```
ccatgtagag ggcgatcggc gcccacaggc tgtcgaacat gccgaagctg ttgacgatct  5280
ggaaggtcgc cacctgggtg gtcaccccgg ggaccagcgc ggccagcagg aacagcgcca  5340
cgaccagcta gttctagagc ggccgccacc gcggtggagc tccaattcgc cctatagtga  5400
gtcgtattac gcgcgctcac tggccgtcgt tttacaacgt cgtgactggg aaaaccctgg  5460
cgttacccaa cttaatcgcc ttgcagcaca tccccctttc gccagctggc gtaatagcga  5520
agaggcccgc accgatcgcc cttcccaaca gttgcgcagc ctgaatggcg aatggaaatt  5580
gtaagcgtta atattttgtt aaaattcgcg ttaaattttt gttaaatcag ctcatttttt  5640
aaccaatagg ccgaaatcgg caaaatccct tataaatcaa aagaatagac cgagataggg  5700
ttgagtgttg ttccagtttg gaacaagagt ccactattaa agaacgtgga ctccaacgtc  5760
aaagggcgaa aaaccgtcta tcagggcgat ggcccactac gtgaaccatc accctaatca  5820
agttttttgg ggtcgaggtg ccgtaaagca ctaaatcgga accctaaagg gagcccccga  5880
tttagagctt gacggggaaa gccggcgaac gtggcgagaa aggaagggaa gaaagcgaaa  5940
ggagcgggcg ctagggcgct ggcaagtgta gcggtcacgc tgcgcgtaac caccacaccc  6000
gccgcgctta atgcgccgct acagggcgcg tcag                                6034
```

```
SEQ ID NO: 15           moltype = DNA  length = 40
FEATURE                 Location/Qualifiers
misc_feature            1..40
                        note = Synthetic oligonucleotide primer
source                  1..40
                        mol_type = other DNA
                        organism = synthetic construct
SEQUENCE: 15
agcacagcta gcttctagaa gcttcattca aaggccggca                          40
```

```
SEQ ID NO: 16           moltype = DNA  length = 44
FEATURE                 Location/Qualifiers
misc_feature            1..44
                        note = Synthetic oligonucleotide primer
source                  1..44
                        mol_type = other DNA
                        organism = synthetic construct
SEQUENCE: 16
aggcagctcg agcatatgac tagtcagagc aggattcccg ttga                     44
```

```
SEQ ID NO: 17           moltype = DNA  length = 30
FEATURE                 Location/Qualifiers
misc_feature            1..30
                        note = Synthetic oligonucleotide primer
source                  1..30
                        mol_type = other DNA
                        organism = synthetic construct
SEQUENCE: 17
gaatggcata tggttcatgt gcagctccat                                     30
```

```
SEQ ID NO: 18           moltype = DNA  length = 30
FEATURE                 Location/Qualifiers
misc_feature            1..30
                        note = Synthetic oligonucleotide primer
source                  1..30
                        mol_type = other DNA
                        organism = synthetic construct
SEQUENCE: 18
tctagaacta gtgaatagga acttcggaat                                     30
```

```
SEQ ID NO: 19           moltype = DNA  length = 8113
FEATURE                 Location/Qualifiers
misc_feature            1..8113
                        note = Synthetic plasmid pKS-orf18ifd-T-AmR(NS)
source                  1..8113
                        mol_type = other DNA
                        organism = synthetic construct
SEQUENCE: 19
gtggcacttt tcggggaaat gtgcgcggaa cccctatttg tttatttttc taaatacatt  60
caaatatgta tccgctcatg agacaataac cctgataaat gcttcaataa tattgaaaaa  120
ggaagagtat gagtattcaa catttccgtg tcgcccttat tccctttttt gcggcatttt  180
gccttcctgt ttttgctcac ccagaaacgc tggtgaaagt aaaagatgct gaagatcagt  240
tgggtgcacg agtgggttac atcgaactgg atctcaacag cggtaagatc cttgagagtt  300
ttcgccccga agaacgtttt ccaatgatga gcacttttaa agttctgcta tgtggcgcgg  360
tattatcccg tattgacgcc gggcaagagc aactcggtcg ccgcatacac tattctcaga  420
atgacttggt tgagtactca ccagtcacag aaaagcatct tacggatggc atgacagtaa  480
gagaattatg cagtgctgcc ataaccatga gtgataacac tgcggccaac ttacttctga  540
caacgatcgg aggaccgaag gagctaaccg cttttttgca caacatgggg gatcatgtaa  600
ctcgccttga tcgttgggaa ccggagctga atgaagccat accaaacgac gagcgtgaca  660
ccacgatgcc tgtagcaatg gcaacaacgt tgcgcaaact attaactggc gaactactta  720
ctctagcttc ccggcaacaa ttaatagact ggatggaggc ggataaagtt gcaggaccac  780
ttctgcgctc ggcccttccg gctggctggt ttattgctga taaatctgga gccggtgagc  840
gtgggtctcg cggtatcatt gcagcactgg ggccagatgg taagccctcc cgtatcgtag  900
ttatctacac gacggggagt caggcaacta tggatgaacg aaatagacag atcgctgaga  960
```

-continued

```
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt tttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatggaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaatttc acacaggaaa cagctatgac catgattacg  2160
ccaagcgcgc aattaaccct cactaaaggg aacaaaagct gggtaccggg ccccccctcg  2220
agcatatgtt catgtgcagc tccatcagca aaaggggatg ataagtttat caccaccgac  2280
tatttgcaac agtgccgttg atcgtgctat gatcgactga tgtcatcagc ggtggagtgc  2340
aatgtcgtgc aatacgaatg gcgaaaagcc gagctcatcg gtcagcttct caaccttggg  2400
gttacccccg gcggtgtgct gctggtccac agctccttcc gtagcgtccg gcccctcgaa  2460
gatgggccac ttggactgat cgaggccctg cgtgctgcgc tgggtccggg agggacgctc  2520
gtcatgccct cgtggtcagg tctggacgac gagccgttcg atcctgccac gtcgcccgtt  2580
acaccggacc ttggagttgt ctctgacaca ttctggcgcc tgccaaatgt aaagcgcagc  2640
gcccatccat ttgcctttgc ggcagcgggg ccacaggcag agcagatcat ctctgatcca  2700
ttgcccctgc cacctcactc gcctgcaagc ccggtcgccc gtgtccatga actcgatggg  2760
caggtacttc tcctcggcgt gggacacgat gccaacacga cgctgcatct tgccgagttg  2820
atggcaaagg ttccctatgg ggtgccgaga cactgcacca ttcttcagga tggcaagttg  2880
gtacgcgtcg attatctcga gaatgaccac tgctgtgagc gctttgcctt ggcggacagg  2940
tggctcaagg agaagagcct tcagaaggaa ggtccagtcg gtcatgcctt tgctcggttg  3000
atccgctccc gcgacattgt ggcgacagcc ctgggtcaac tgggccgaga tccgttgatc  3060
ttcctgcatc cgccagaggc gggatgcgaa gaatgcgatg ccgctcgcca gtcgattggc  3120
tgagctcatg aagttcctat tccgaagttc ctattcacta gtcagagcag gattcccgtt  3180
gagcaccgcc aggtgcgaat aagggacagt gaagaaggaa cacccgctcg cgggtgggcc  3240
tacttcacct atcctgcccg gctgacgccg ttggatacac caaggaaagt ctacacgaac  3300
cctttggcaa aatcctgtat atcgtgcgaa aaaggatgga tataccgaaa aaatcgctat  3360
aatgaccccg aagcagggtt atgcagcgga aaatgcagct cacggtaact gatgccgtat  3420
ttgcagtacc agcgtacggc ccacagaatg atgtcacgct gaaaatgccg gcctttgaat  3480
gaagcttgcc ggggccgacg cggcgggcgg cctcgtccat cgggacgcgc cagtcgacgc  3540
cgacgatgtc cgcgccggcc tcgcccatga gccccagcag ctcgccggtg ccgacgccga  3600
agtggatgcg cgggacgccg tggccggcca ccgcgcggaa caccttcgcc gaggcgggca  3660
gcaccgaacg ccggtagtcg gagggggcga gcgcgccggc ccaggagtcg aagagctgca  3720
cggccgaggc gccggcccgg atctggacgt cgaggaaggc cgccgtgatg tcggcgaggc  3780
ggtcgagcag gtcggcccag agctcggggt cgccgtacat catcgccttg gcgttctcgt  3840
acgtacggga cgggccgccc tcgacgaggt aactcgcaag ggtgaacggg gcgcccgcga  3900
aaccgatcag cggggtggac ccgagctcac gggtcagcat gccgatggcc tcggtgacgt  3960
aggagacgtc ctccggggtc aggtcgcgca gccgggcgag gtcggcgcgg gtgcgcaccg  4020
gctgctcgac gaccgggccg atgccgggct tgatgtcgag gtcgatgccg atggccttga  4080
gcgggacgac gatgtcgctg aagtagatcg ccgcgtcgac gtggtggcgg cgcaccggct  4140
ggagggtgat ctcggtgacc agctcgggcc gcatgcagga gtcgagcatc ccgatgccct  4200
cgcgcacctt gcggtactcc ggcagtgagc gcccggcctg ccgcatgaac cacaccggcg  4260
tgtgcggcac cggctcgcgc cggcacgcct tgaggaaggc tgattcccgg acggcgtcgt  4320
tcttgacggg gtcgggggtc gcggtaggcg tctggccctt cgggctcgtg ttggcactca  4380
caccggccag tctcgcacga cccgtccgcc gccccggacc ccaggggcgt ccggcgggcg  4440
gggccgcggt gcaggatccg gacagcgccg ggcggcgcgg gtgtccctcc ctgcgccggg  4500
ggcccgttcc gcttaatctt cccggcatgg ctgcggctca gggacgactg tcggacggcg  4560
ctggcggaat ggacgaaccg aaggagggcg ggggggatcc cgggcacgga ggtgcgcctc  4620
cgccgccctt ccgggccgct gtcgaggcgc tgcagagcgc ccggctgcgg ccgcagatcg  4680
aggtggagac ggtgcccgcg ccgaaacggc tcgccccgta cgcgcacgcg ctggaggcgg  4740
cggtcgtcga cggcgaggag gatctggccg acggccggct ggtgctgctg tgcgacccgg  4800
ccggacacga cgcctggcgg gggaccttcc gtctggtgac gctggtgcgc gccgagctgg  4860
agccggagat ggcggcggat ccgctgctgc cggacgtgtg ctggtcctgg ctgaccggcg  4920
cgctggcggc gcgcggcctg tcgtacggcg agccgagcgg cacggtgacg cgggcgagtt  4980
cgcactactt cggcgggctg tccgcgcggc ccgccgcctc ccagatcgag atccgtgcct  5040
cgtggacgcc gcgtgagggt ctgggcgggg ttccggacac ggccgcccat ctggtcgcgt  5100
ggtccgatct gctggcgcag gtcgcggggc tgccgccggc cgctccgggg gacgcgtccg  5160
tggtgacgct gccgcagcgg agggggccgc agtcgcgctg agcctcccgc tgcggggtcc  5220
cgacgaccgg cctcctgcat ctctctttgt cgatacggcc actttcggaa gcgttgcgac  5280
gcagaccgaa accgttcgat cttcgaatga tcgatcgtgc gtccgaattg cccggattgt  5340
tactcatcac ttcgtgatca ttcgttaaag gacaccaggt ttgctgccga agacgactgt  5400
gaccttgaaa gcacggttcg tcccgccttc acccccacga gccggcccgt cccgcacccc  5460
aggaggcctg gtgtttaatt aatgaccctt ccgtcccgcc cccgatccgc ccgtccccga  5520
tccgcccgcc cacggccaag cgaacacgtt ctttcactct tctgaccgga atacgaccca  5580
ccggcgcccg tcacggagca caaccgtcga cgggcgcctt cgcggcacgg atacccttga  5640
caggtgaccg acgcccacga caccgcagca gacagttcac tgcgcaccac cggaggcgct  5700
```

```
cctccggacg acggcggatc ttctgttacg gaggcgccga ccccccttgct ggaaccccgc  5760
gagggcattc cgcccgtgat agcggacgag gccgccctcg ccgaggcggt cgccgccttc  5820
gcggccggca gcggacccgt cgccgtggac gccgagcgcg cctccgggta ccgctacggc  5880
cagcgcgcct acctcgtcca gctgcgccgc gagggtgcgg gtaccgcgct gatcgacccc  5940
gtggcctgcc ccgacctgtc cgccctcggc gaggcgctgt ccggcgtcga gtgggtgctg  6000
cacgccgcca cccaggacct gccctgtctg cgcgagatag gcatggtgcc ctcccgcctc  6060
ttcgacaccg agctggccgg ccgccttgcc gggttccccc gcgtcgggct cggcgcgatg  6120
gtcgagaacg tgctcggctt cgtcctggag aagggccact ccgccgtcga ctggtccacc  6180
cgtccgctgc ccgagccctg gctgcggtac gccgccctcg acgtcgaact gctggtcgat  6240
ctgcgggacg ccctggagaa ggagctggac cgccagggca agctggactg ggcccggcag  6300
gagttcgacg cgatcgcctc ggccccgccg ccggagcccc gcaaggaccc ctggcgccgc  6360
acctccggca tgcacaaggt gcgccggcgc cgccagatgg cggtggtgcg ggagctgtgg  6420
gagacccgcg accggatcgc ccggcgcccgt gacgtctccc ccggcaaggt gctttccgac  6480
gcggcgatcg tggaggccgc gctcgcgctg cccgccaacc tgcacgccat ggccgcgctc  6540
aacgggttcg ggcagcgggt ggggcggcgc cagctggagc agtggcaggc ggccgtcgac  6600
cgcgcgaagg cgctgagcga ggcccagctg ccgcagcccg gccagccggt gaccggccct  6660
ccgccgccgc gcgcctgggc ggacaaggac cccgttgccg cggcccggct gtcggcggcc  6720
cgcgcggggg tcgccgaact cgccgagcgg ctgaacatgc cgccggagaa cctgatcacc  6780
ccggacacgg tgcgcagggt ctgctgggag ccgccggggc ccgacgagcg gtccgtcgcc  6840
gcggcgctga cggcgcacgg ggcacgcgcg tggcaggtcg accaggtcac tcccgtgctg  6900
gtggccgcgc tggctacttc gtcgcccccc gcatgaaccc gttgtagatg aagcgctgga  6960
ggaacaggaa gacgatcaag gtgggcagga tgaccaggac cgcgcccgcc gagatcgtct  7020
cccagtgcgc gccgaagggg cccttgaagc ggaacaggga cgtcgagatg acccccaggt  7080
cctcggaggg catgtagagg aaggggatgt agaagtcgtt gtagacgttg atccccttta  7140
cgatcaccac cgtcgcgatc gccggcttga gcagcgggaa gatcaccttg cggtagacgg  7200
tgaacgcgtt ggcgccgtcc aggcgcgccg cctcgtccag ggagacgggg atggagcgga  7260
tgaactgcag gaagacgtag atcgagacga tgtccgtgcc catgtagagg gcgatcggcg  7320
cccacaggct gtcgaacatg ccgaagctgt tgacgatctg gaaggtcgcc acctgggtgg  7380
tcaccccggg gaccagcgcg gccagcagga acagcgccac gaccagctag ttctagagcg  7440
gccgccaccg cggtggagct ccaattcgcc ctatagtgag tcgtattacg cgcgctcact  7500
ggccgtcgtt ttacaacgtc gtgactggga aaaccctggc gttacccaac ttaatcgcct  7560
tgcagcacat ccccctttcg ccagctggcg taatagcgaa gaggcccgca ccgatcgccc  7620
ttcccaacag ttgcgcagcc tgaatggcga atggaaattg taagcgttaa tattttgtta  7680
aaattcgcgt taaatttttg ttaaatcagc tcatttttta accaataggc cgaaatcggc  7740
aaaatccctt ataaatcaaa agaatagacc gagatagggt tgagtgttgt tccagtttgg  7800
aacaagagtc cactattaaa gaacgtggac tccaacgtca aagggcgaaa aaccgtctat  7860
cagggcgatg gcccactacg tgaaccatca ccctaatcaa gtttttttggg gtcgaggtgc  7920
cgtaaagcac taaatcggaa ccctaaaggg agcccccgat ttagagcttg acggggaaag  7980
ccggcgaacg tggcgagaaa ggaagggaag aaagcgaaag gagcgggcgc tagggcgctg  8040
gcaagtgtag cggtcacgct gcgcgtaacc accacacccg ccgcgcttaa tgcgccgcta  8100
cagggcgcgt cag                                                       8113

SEQ ID NO: 20           moltype = DNA  length = 7120
FEATURE                 Location/Qualifiers
misc_feature            1..7120
                        note = Synthetic plasmid pXY152-endorf24-camtsr
source                  1..7120
                        mol_type = other DNA
                        organism = synthetic construct
SEQUENCE: 20
gaattcgtaa tcatgtcata gctgtttcct gtgtgaaatt gttatccgct cacaattcca  60
cacaacatac gagccggaag cataaagtgt aaagcctggg gtgcctaatg agtgagctaa  120
ctcacattaa ttgcgttgcg ctcactgccc gctttccagt cgggaaacct gtcgtgccag  180
ctgcattaat gaatcggcca acgcgcgggg agaggcggtt tgcgtattgg gcgctcttcc  240
gcttcctcgc tcactgactc gctgcgctcg gtcgttcggc tgcggcgagc ggtatcagct  300
cactcaaagg cggtaatacg gttatccaca gaatcagggg ataacgcagg aaagaacatg  360
tgagcaaaag gccagcaaaa ggccaggaac cgtaaaaagg ccgcgttgct ggcgtttttc  420
cataggctcc gcccccctga cgagcatcac aaaaatcgac gctcaagtca gaggtggcga  480
aacccgacag gactataaag ataccaggcg tttccccctg gaagctccct cgtgcgctct  540
cctgttccga ccctgccgct taccggatac ctgtccgcct ttctcccttc gggaagcgtg  600
gcgctttctc atagctcacg ctgtaggtat ctcagttcgg tgtaggtcgt tcgctccaag  660
ctgggctgtg tgcacgaacc ccccgttcag cccgaccgct gcgccttatc cggtaactat  720
cgtcttgagt ccaacccggt aagacacgac ttatcgccac tggcagcagc cactggtaac  780
aggattagca gagcgaggta tgtaggcggt gctacagagt tcttgaagtg gtggcctaac  840
tacggctaca ctagaagaac agtatttggt atctgcgctc tgctgaagcc agttaccttc  900
ggaaaaagag ttggtagctc ttgatccggc aaacaaacca ccgctggtag cggtggtttt  960
tttgtttgca agcagcagat tacgcgcaga aaaaaaggat ctcaagaaga tcctttgatc  1020
ttttctacgg ggtctgacgc tcagtggaac gaaaactcac gttaagggat tttggtcatg  1080
agattatcaa aaaggatctt cacctagatc cttttggttc atgtgcagct ccatcagcaa  1140
aaggggatga taagtttatc accaccgact atttgcaaca gtgccgttga tcgtgctatg  1200
atcgactgat gtcatcagcg gtggagtgca atgtcgtgca atacgaatgg cgaaaagccg  1260
agctcaataa ctgccttaaa aaaattacgc cccgccctgc cactcatcgc agtactgttg  1320
taattcatta agcattctgc cgacatggaa gccatcacaa acggcatgat gaacctgaat  1380
cgccagcggc atcagcacct tgtcgccttg cgtataatat ttgcccatcg tgaaaacggg  1440
ggcgaagaag ttgtccatat tggccacgtt taagtcaaaa ctggtgaaac tcacccaggg  1500
attggctgag acgaaaaaca tattctcaat aaacccttta gggaaatagg ccaggttttc  1560
accgtaacac gccacatctt gcgaatatat gtgtagaaac tgccggaaat cgtcgtggta  1620
ttcactccag agcgatgaaa acgtttcagt ttgctcatgg aaaacggtgt aacaagggtg  1680
aacactatcc catatcacca gctcaccgtc tttcattgcc atacgaaatt ccggatgagc  1740
```

-continued

```
attcatcagg cgggcaagaa tgtgaataaa ggccggataa aacttgtgct tattttctt  1800
tacggtcttt aagaaggccg taatatccag ttgaacggtc tggttatagg tacattgagc  1860
aactgactga aatgcctcaa aatgttcttt acgatgccat tgggatatat caacggtggt  1920
atatccagtg attttttct ccattttagc ttccttagct cctgaaaatc tcgataactc  1980
aaaaaatacg cccggtagtg atcttatttc attatggtga aagttggaac ctcttacgtg  2040
ccgatcaacg tctcattttc gccaaaagtt ggcccagggc ttcccggtat caacagggac  2100
accaggattt atttattctg cgaagtgatc ttccgtcaca ggtatttatt cgcgataagc  2160
tcatggagcg gcgtaaccgt cgcacaggaa ggacagagaa agcgcggaag cttatttaaa  2220
taccgcgcgg gtcccggacg gggaagagcg gggagctttg ccagagagcg acgacttccc  2280
cttgcgttgg tgattgccgg tcagggcagc catccgccat cgtcgcgtag ggtgtcacac  2340
cccaggaatc gcgtcactga acacagcagc cggtaggacg accatgactg agttggacac  2400
catcgcaaat ccgtccgatc cggcggtgca gcggatcatc gatgtcacca agccgtcgcg  2460
atccaacata aagacaacgt tgatcgagga cgtcgagccc ctcatgcaca gcatcgcggc  2520
cggggtggag ttcatcgagg tctacggcag cgacagcagt ccttttccat ctgagttgct  2580
ggatctgtgc gggcggcaga acataccggt ccgcctcatc gactcctcga tcgtcaacca  2640
gttgttcaag gggggagcgga aggccaagac attcggcatc gcccgcgtcc ctcgcccggc  2700
caggttcggc gacatcgcga gccggcgtgg ggacgtcgtc gttctcgacg gggtgaagat  2760
cgtcgggaac atcggcgcga tagtacgcac gtcgctcgcg ctcggagcgt cggggatcat  2820
cctggtcgac agtgacatca ccagcatcgc ggaccggcgt ctccaaaggg ccagccgagg  2880
ttacgtcttc tcccttcccg tcgttctctc cggtcgcgag gaggccatcg ccttcattcg  2940
ggacagcggt atgcaactga tgacgctcaa ggcggatggc gacatttccg tgaaggaact  3000
cggggacaat ccggatcggc tggccttgct gttcggcagc gaaaagggtg ggccttccga  3060
cctgttcgag gaggcgtctt ccgcctcggt ttccatcccc atgatgagcc agaccgagtc  3120
tctcaacgtt tccgtttccc tcggaatcgc gctgcacgag aggatcgaca ggaatctcgc  3180
ggccaaccga taagctagct agagtcgacc tgcaggtccc cggggatcgg tcttgccttg  3240
ctcgtcggtg atgtacttca ccagctccgc gaagtcgctc ttcttgatgg agcgcatggg  3300
gacgtgcttg gcaatcacgc gcaccccccg gccgttttag cggctaaaaa agtcatggct  3360
ctgccctcgg gcggaccacg cccatcatga ccttgccaag ctcgtcctgc ttctcttcga  3420
tcttcgccag cagggcgagg atcgtggcat caccgaaccg cgccgtgcgc gggtcgtcgg  3480
tgagccagag tttcagcagg ccgcccaggc ggcccaggtc gccattgatg cgggccagct  3540
cgcggacgtg ctcatagtcc acgacgcccg tgattttgta gccctggccg acggccagca  3600
ggtaggccga caggctcatg ccggccgccg ccgccttttc ctcaatcgct cttcgttcgt  3660
ctggaaggca gtacaccttg ataggtgggc tgcccttcct ggttggcttg gtttcatcag  3720
ccatccgctt gccctcatct gttacgccgg cggtagccgg ccagcctcgc agagcaggat  3780
tcccgttgag caccgccagg tgcgaataag ggacagtgaa gaaggaacac ccgctcgcgg  3840
gtgggcctac ttcacctatc ctgcccggct gacgccgttg gatacaccaa ggaaagtcta  3900
cacgaaccct ttggcaaaat cctgtatatc gtgcgaaaaa ggatggatat accgaaaaaa  3960
tcgctataat gaccccgaag cagggttatg cagcggaaaa gatccgtcga cctgcaggca  4020
tgcaagctct agcgattcca gacgtcccga aggcgtggcg cggcttcccc gtgccggagc  4080
aatcgccctg ggtgggttac acgacgcccc tctatggccc gtactgacgg acacaccgaa  4140
gccccggcgg caaccctcag cggatgcccc ggggcttcac gttttcccag gtcagaagcg  4200
gttttcggga gtagtgcccc aactggggta acctttgagt tctctcagtt gggggcgtag  4260
ggtcgccgac atgacacaag gggttgtgac cggggtggac acgtacgcgg gtgcttacga  4320
ccgtcagtcg cgcgagcgcg agaactcgag cgcagcaagc ccagcgacac agcgtagcgc  4380
caacgaagac aaggcggccg accttcagcg cgaagtcgag cgcgacgggg gccggttcag  4440
gttcgtcggg catttcagcg aagcgccggg cacgtcggcg ttcgggacgg cggagcgccc  4500
ggagttcgaa cgcatcctga acgaatgccg cgccgggcgg ctcaacatga tcattgtcta  4560
tgacgtgtcg cgcttctcgc gcctgaaggt catggacgcg attccgattg tctcggaatt  4620
gctcgccctg ggcgtgacga ttgtttccac tcaggaaggc gtcttccggc agggaaacgt  4680
catggacctg attcacctga ttatgcggct cgacgcgtcg cacaaagaat cttcgctgaa  4740
gtcggcgaag attctcgaca cgaagaacct tcagcgcgaa ttgggcgggt acgtcggcgg  4800
gaaggcgcct tacggcttcg agcttgtttc ggagacgaag gagatcacgc gcaacggccg  4860
aatggtcaat gtcgtcatca acaagcttgc gcactcgacc actcccctta ccggaccctt  4920
cgagttcgag cccgacgtaa tccggtggtg gtggcgtgag atcaagacgc acaaacacct  4980
tcccttcaag ccgggcagtc aagccgccat tcacccgggc agcatcacgg ggctttgtaa  5040
gcgcatggac gctgacgccg tgccgacccg gggcgagacg attgggaaga agaccgcttc  5100
aagcgcctgg gacccggcaa ccgttatgcg aatccttcgg gacccgcgta ttgcgggctt  5160
cgccgctgag gtgatctaca agaagaagcc ggacggcacg ccgaccacga agattgaggg  5220
ttaccgcatt cagcgcgacc cgatcacgct ccggccggtc gagcttgatt gcggaccgat  5280
catcgagccc gctgagtggt atgagcttca ggcgtggttg gacggcaggg ggcgcggcaa  5340
ggggctttcc cgggggcaag ccattctgtc cgccatggac aagctgtact gcgagtgtgg  5400
cgccgtcatg acttcgaagc gcggggaaga atcgatcaag gactcttacc gctgccgtcg  5460
ccggaaggtg gtcgacccgt ccgcacctgg gcagcacgaa ggcacgtgca acgtcagcat  5520
ggcggcactc gacaagttcg ttgcggaacg catcttcaac aagatcaggc acgccgaagg  5580
cgacgaagag acgttggcgc ttctgtggga agccgcccga cgcttcggca agctcactga  5640
ggcgcctgag aagagcggcg aacgggcgaa ccttgttgcg gagcgcgccg acgccctgaa  5700
cgcccttgaa gagctgtacg aagaccgcgc ggcaggcgcg tacgacggac ccgttggcag  5760
gaagcacttc cggaagcaac aggcagcgct gacgctccgg cagcaagggg cggaagagcg  5820
gcttgccgaa cttgaagccg ccgaagcccc gaagcttccc cttgaccaat ggttccccga  5880
agacgccgac gctgacccga ccggccctaa gtcgtggtgg gggcgcgcgt cagtagacga  5940
caagcgcgtg ttcgtcgggc tcttcgtaga caagatcgtt gtcacgaagt cgactacggg  6000
cagggggcag ggaacgccca tcgagaagcg cgcttcgatc acgtgggcga agccgccgac  6060
cgacgacgac gaagacgacg cccaggacgg cacggaagac gtagcggcgt aggtgagtga  6120
agatctagac gtggcaccgc gatgctgttg tgggcacaat cgtgccggtt ggtaggatcc  6180
acatatggaa ataagttcgc tctccaccga cggctccccg cggatcgacg gggagagtcc  6240
cgagcacgtg gaaatgctgg ccgccgccga caccgcgctt ccaccgatca tggtgcaccg  6300
ccgcaccggg cgggtcatcg acggcatgca ccggctgcgc gccgcgatgc tgacgggccg  6360
tacgacgatc gcggtgaggt tcttcgacgg caccgaggag gacgccttcg tcctcgccgt  6420
gaagtcgaac atcgcgcacg gactgccgct gtccgccgcc gaccgccggc gggccgccgg  6480
```

```
gcgcatcatg gccacccatc cccggtggtc ggaccggatg atcgcctcgg tggtcggcac  6540
ctccgccagg acggtcgccg agatccgccg cgacgccggc gccgccgggg cgggggagcc  6600
caccccgcatc ggccgggacg gcagggtacg gcccgtcgac gtgagcgagg gccgcagact  6660
ggcccacgac atgatcgtcc gcgacccggg cctgtcgctg cgccaggtcg cccgcgccgc  6720
cgggatctcg ccggagaccg tcagggacgt cagacaccgg atgctccgcg gtgaggaccc  6780
ggtgcccgcg ccgcggccgc ggaccctggt ggagcgcggc gcggaccgcc gggcggagcc  6840
ggccgggaag gccgccgcgc cgtgcgggac ggagccgccg cccgccgtcg tgatgaagcg  6900
gctgagggcc gatccggcgc tgcgtctcaa cgagaacgga cgcgacctgc tgcggcttct  6960
ggatatccac acggtccggc tggaggactg gaaccgcatt atcgaaagcg tgccgccgca  7020
ccgtctggag acggtggcgc agctggcacg ctcctgcgcc gacaaatggt ccgagatcgc  7080
gtcacgcatc gaaagcaacg catcacatct ggccgggtga                        7120

SEQ ID NO: 21          moltype = DNA  length = 30
FEATURE                Location/Qualifiers
misc_feature           1..30
                       note = Synthetic oligonucleotide primer
source                 1..30
                       mol_type = other DNA
                       organism = synthetic construct
SEQUENCE: 21
gtggcaattt aaatggaaat gtgcgcggaa                                   30

SEQ ID NO: 22          moltype = DNA  length = 31
FEATURE                Location/Qualifiers
misc_feature           1..31
                       note = Synthetic oligonucleotide primer
source                 1..31
                       mol_type = other DNA
                       organism = synthetic construct
SEQUENCE: 22
tatatagagc tcaacttggt ctgacagtta c                                 31

SEQ ID NO: 23          moltype = DNA  length = 7162
FEATURE                Location/Qualifiers
misc_feature           1..7162
                       note = Synthetic pXY152-endorf24-blatsr
source                 1..7162
                       mol_type = other DNA
                       organism = synthetic construct
SEQUENCE: 23
gaattcgtaa tcatgtcata gctgtttcct gtgtgaaatt gttatccgct cacaattcca  60
cacaacatac gagccggaag cataaagtgt aaagcctggg gtgcctaatg agtgagctaa  120
ctcacattaa ttgcgttgcg ctcactgccc gctttccagt cgggaaacct gtcgtgccag  180
ctgcattaat gaatcggcca acgcgcgggg agaggcggtt tgcgtattgg gcgctcttcc  240
gcttcctcgc tcactgactc gctgcgctcg gtcgttcggc tgcggcgagc ggtatcagct  300
cactcaaagg cggtaatacg gttatccaca gaatcagggg ataacgcagg aaagaacatg  360
tgagcaaaag gccagcaaaa ggccaggaac cgtaaaaagg ccgcgttgct ggcgtttttc  420
cataggctcc gcccccctga cgagcatcac aaaaatcgac gctcaagtca gaggtggcga  480
aacccgacag gactataaag ataccaggcg tttccccctg gaagctccct cgtgcgctct  540
cctgttccga ccctgccgct taccggatac ctgtccgcct ttctcccttc gggaagcgtg  600
gcgctttctc atagctcacg ctgtaggtat ctcagttcgg tgtaggtcgt tcgctccaag  660
ctgggctgtg tgcacgaacc ccccgttcag cccgaccgct gcgccttatc cggtaactat  720
cgtcttgagt ccaacccggt aagacacgac ttatcgccac tggcagcagc cactggtaac  780
aggattagca gagcgaggta tgtaggcggt gctacagagt tcttgaagtg gtggcctaac  840
tacggctaca ctagaagaac agtatttggt atctgcgctc tgctgaagcc agttaccttc  900
ggaaaaagag ttggtagctc ttgatccggc aaacaaacca ccgctggtag cggtggtttt  960
tttgtttgca agcagcagat tacgcgcaga aaaaaaggat ctcaagaaga tcctttgatc  1020
ttttctacgg ggtctgacgc tcagtggaac gaaaactcac gttaagggat tttggtcatg  1080
agattatcaa aaaggatctt cacctagatc cttttggttc atgtgcagct ccatcagcaa  1140
aaggggatga taagtttatc accaccgact atttgcaaca gtgccgttga tcgtgctatg  1200
atcgactgat gtcatcagcg gtggagtgca atgtcgtgca atacgaatgg cgaaaagccg  1260
agctcaactt ggtctgacag ttaccaatgc ttaatcagtg aggcacctat ctcagcgatc  1320
tgtctatttc gttcatccat agttgcctga ctccccgtcg tgtagataac tacgatacgg  1380
gagggcttac catctggccc cagtgctgca atgataccgc gagacccacg ctcaccggct  1440
ccagatttat cagcaataaa ccagccagcc ggaagggccg agcgcagaag tggtcctgca  1500
actttatccg cctccatcca gtctattaat tgttgccggg aagctagagt aagtagttcg  1560
ccagttaata gtttgcgcaa cgttgttgcc attgctacag gcatcgtggt gtcacgctcg  1620
tcgtttggta tggcttcatt cagctccggt tcccaacgat caaggcgagt tacatgatcc  1680
cccatgttgt gcaaaaaagc ggttagctcc ttcggtcctc cgatcgttgt cagaagtaag  1740
ttggccgcag tgttatcact catggttatg gcagcactgc ataattctct tactgtcatg  1800
ccatccgtaa gatgcttttc tgtgactggt gagtactcaa ccaagtcatt ctgagaatag  1860
tgtatgcggc gaccgagttg ctcttgcccg gcgtcaatac gggataatac cgcgccacat  1920
agcagaactt taaaagtgct catcattgga aaacgttctt cggggcgaaa actctcaagg  1980
atcttaccgc tgttgagatc cagttcgatg taacccactc gtgcacccaa ctgatcttca  2040
gcatctttta ctttcaccag cgtttctggg tgagcaaaaa caggaaggca aaatgccgca  2100
aaaaagggaa taagggcgac acggaaatgt tgaatactca tactcttcct ttttcaatat  2160
tattgaagca tttatcaggg ttattgtctc atgagcggat acatatttga atgtatttag  2220
aaaaataaac aaataggggt tccgcgcaca tttccattta aataccgcgc gggtcccgga  2280
cggggaagag cggggagctt tgccagagag cgacgacttc cccttgcgtt ggtgattgcc  2340
```

-continued

```
ggtcagggca gccatccgcc atcgtcgcgt agggtgtcac accccaggaa tcgcgtcact  2400
gaacacagca gccggtagga cgaccatgac tgagttggac accatcgcaa atccgtccga  2460
tccggcggtg cagcggatca tcgatgtcac caagccgtcg cgatccaaca taaagacaac  2520
gttgatcgag gacgtcgagc ccctcatgca cagcatcgcg gccggggtgg agttcatcga  2580
ggtctacggc agcgacagca gtccttttcc atctgagttg ctggatctgt gcgggcggca  2640
gaacataccg gtccgcctca tcgactcctc gatcgtcaac cagttgttca agggggagcg  2700
gaaggccaag acattcggca tcgcccgcgt ccctcgcccg gccaggttcg gcgacatcgc  2760
gagccggcgt ggggacgtcg tcgttctcga cggggtgaag atcgtcggga acatcggcgc  2820
gatagtacgc acgtcgctcg cgctcggagc gtcggggatc atcctggtcg acagtgacat  2880
caccagcatc gcggaccggc gtctccaaag ggccagccga ggttacgtct tctcccttcc  2940
cgtcgttctc tccggtcgcg aggaggccat cgccttcatt cgggacagcg gtatgcaact  3000
gatgacgctc aaggcggatg gcgacatttc cgtgaaggaa ctcggggaca atccggatcg  3060
gctggccttg ctgttcggca gcgaaaaggg tgggccttcc gacctgttcg aggaggcgtc  3120
ttccgcctcg gtttccatcc ccatgatgag ccagaccgag tctctcaacg tttccgtttc  3180
cctcggaatc gcgctgcacg agaggatcga caggaatctc gcggccaacc gataagctag  3240
ctagagtcga cctgcaggtc cccggggatc ggtcttgcct tgctcgtcgg tgatgtactt  3300
caccagctcc gcgaagtcgc tcttcttgat ggagcgcatg gggacgtgct tggcaatcac  3360
gcgcaccccc cggccgtttt agcggctaaa aaagtcatgg ctctgccctc gggcggacca  3420
cgcccatcat gaccttgcca agctcgtcct gcttctcttc gatcttcgcc agcagggcga  3480
ggatcgtggc atcaccgaac cgcgccgtgc gcgggtcgtc ggtgagccag agtttcagca  3540
ggccgcccag gcggcccagg tcgccattga tgcgggccag ctcgcggacg tgctcatagt  3600
ccacgacgcc cgtgattttg tagccctggc cgacggccag caggtaggcc gacaggctca  3660
tgccggccgc cgccgccttt tcctcaatcg ctcttcgttc gtctggaagg cagtacacct  3720
tgataggtgg gctgcccttc ctggttggct tggtttcatc agccatccgc ttgccctcat  3780
ctgttacgcc ggcggtagcc ggccagcctc gcagagcagg attcccgttg agcaccgcca  3840
ggtgcgaata agggacagtg aagaaggaac acccgctcgc gggtgggcct acttcaccta  3900
tcctgcccgg ctgacgccgt tggatacacc aaggaaagtc tacacgaacc ctttggcaaa  3960
atcctgtata tcgtgcgaaa aaggatggat ataccgaaaa aatcgctata atgaccccga  4020
agcagggtta tgcagcggaa aagatccgtc gacctgcagg catgcaagct ctagcgattc  4080
cagacgtccc gaaggcgtgg cgcggcttcc ccgtgccgga gcaatcgccc tgggtgggtt  4140
acacgacgcc cctctatggc ccgtactgac ggacacaccg aagccccggc ggcaaccctc  4200
agcggatgcc ccggggcttc acgttttccc aggtcagaag cggttttcgg gagtagtgcc  4260
ccaactgggg taacctttga gttctctcag ttgggggcgt agggtcgccg acatgacaca  4320
aggggttgtg accggggtgg acacgtacgc gggtgcttac gaccgtcagt cgcgcgagcg  4380
cgagaactcg agcgcagcaa gcccagcgac acagcgtagc gccaacgaag acaaggcggc  4440
cgaccttcag cgcgaagtcg agcgcgacgg gggccggttc aggttcgtcg ggcatttcag  4500
cgaagcgccg ggcacgtcgg cgttcgggac ggcggagcgc ccggagttcg aacgcatcct  4560
gaacgaatgc cgcgccgggc ggctcaacat gatcattgtc tatgacgtgt cgcgcttctc  4620
gcgcctgaag gtcatggacg cgattccgat tgtctcggaa ttgctcgccc tgggcgtgac  4680
gattgtttcc actcaggaag gcgtcttccg gcagggaaac gtcatggacc tgattcacct  4740
gattatgcgg ctcgacgcgt cgcacaaaga atcttcgctg aagtcggcga agattctcga  4800
cacgaagaac cttcagcgcg aattgggcgg gtacgtcggc gggaaggcgc cttacggctt  4860
cgagcttgtt tcggagacga aggagatcac gcgcaacggc cgaatggtca atgtcgtcat  4920
caacaagctt gcgcactcga ccactcccct taccggaccc ttcgagttcg agcccgacgt  4980
aatccggtgg tggtggcgtg agatcaagac gcacaaacac cttcccttca agccgggcag  5040
tcaagccgcc attcacccgg gcagcatcac ggggctttgt aagcgcatgg acgctgacgc  5100
cgtgccgacc cggggcgaga cgattgggaa gaagaccgct tcaagcgcct gggacccggc  5160
aaccgttatg cgaatccttc gggacccgcg tattgcgggc ttcgccgctg aggtgatcta  5220
caagaagaag ccggacggca cgccgaccac gaagattgag ggttaccgca ttcagcgcga  5280
cccgatcacg ctccggccgg tcgagcttga ttgcggaccg atcatcgagc ccgctgagtg  5340
gtatgagctt caggcgtggt tggacggcag ggggcgcggc aaggggcttt cccgggggca  5400
agccattctg tccgccatgg acaagctgta ctgcgagtgt ggcgccgtca tgacttcgaa  5460
gcgcggggaa gaatcgatca aggactctta ccgctgccgt cgccggaagg tggtcgaccc  5520
gtccgcacct gggcagcacg aaggcacgtg caacgtcagc atggcggcac tcgacaagtt  5580
cgttgcggaa cgcatcttca acaagatcag gcacgccgaa ggcgacgaag agacgttggc  5640
gcttctgtgg gaagccgccc gacgcttcgg caagctcact gaggcgcctg agaagagcgg  5700
cgaacgggcg aaccttgttg cggagcgcgc cgacgccctg aacgcccttg aagagctgta  5760
cgaagaccgc gcggcaggcg cgtacgacgg acccgttggc aggaagcact tccggaagca  5820
acaggcagcg ctgacgctcc ggcagcaagg ggcggaagag cggcttgccg aacttgaagc  5880
cgccgaagcc ccgaagcttc cccttgacca atggttcccc gaagacgccg acgctgaccc  5940
gaccggccct aagtcgtggt gggggcgcgc gtcagtagac gacaagcgcg tgttcgtcgg  6000
gctcttcgta gacaagatcg ttgtcacgaa gtcgactacg ggcagggggc agggaacgcc  6060
catcgagaag cgcgcttcga tcacgtgggc gaagccgccg accgacgacg acgaagacga  6120
cgcccaggac ggcacggaag acgtagcggc gtaggtgagt gaagatctag acgtggcacc  6180
gcgatgctgt tgtgggcaca atcgtgccgg ttggtaggat ccacatatgg aaataagttc  6240
gctctccacc gacggctccc cgcggatcga cggggagagt cccgagcacg tggaaatgct  6300
ggccgccgcc gacaccgcgc ttccaccgat catggtgcac cgccgcaccg ggcgggtcat  6360
cgacggcatg caccggctgc gcgccgcgat gctgacgggc cgtacgacga tcgcggtgag  6420
gttcttcgac ggcaccgagg aggacgcctt cgtcctcgcc gtgaagtcga acatcgcgca  6480
cggactgccg ctgtccgccg ccgaccgccg gcgggccgcc gggcgcatca tggccaccca  6540
tccccggtgg tcggaccgga tgatcgcctc ggtggtcggc acctccgcca ggacggtcgc  6600
cgagatccgc cgcgacgccg gcgccgccgg ggcgggggag cccacccgca tcggccggga  6660
cggcagggta cggcccgtcg acgtgagcga gggccgcaga ctggcccacg acatgatcgt  6720
ccgcgacccg ggcctgtcgc tgcgccaggt cgcccgcgcc gccgggatct cgccggagac  6780
cgtcagggac gtcagacacc ggatgctccg cggtgaggac ccggtgcccg cgccgcggcc  6840
gcggaccctg gtggagcgcg gcgcggaccg ccgggcggag ccggccggga aggccgccgc  6900
gccgtgcggg acggagccgc cgcccgccgt cgtgatgaag cggctgaggg ccgatccggc  6960
gctgcgtctc aacgagaacg gacgcgacct gctgcggctt ctggatatcc acacggtccg  7020
gctggaggac tggaaccgca ttatcgaaag cgtgccgccg caccgtctgg agacggtggc  7080
```

```
gcagctggca cgctcctgcg ccgacaaatg gtccgagatc gcgtcacgca tcgaaagcaa  7140
cgcatcacat ctggccgggt ga                                           7162

SEQ ID NO: 24           moltype = DNA  length = 24
FEATURE                 Location/Qualifiers
misc_feature            1..24
                        note = Synthetic oligonucleotide primer
source                  1..24
                        mol_type = other DNA
                        organism = synthetic construct
SEQUENCE: 24
aaggagaaga gccttcagaa ggaa                                         24

SEQ ID NO: 25           moltype = AA  length = 321
FEATURE                 Location/Qualifiers
source                  1..321
                        mol_type = protein
                        organism = Streptomyces griseus
SEQUENCE: 25
MDPTRVDIFA LPAVEIELSR LSSASSPRTS GEDPEHVETL LSAEGELPPI LVHRPTMQVL  60
DGLHRLKVAR VRGDTKILAR LVDATESDAF VLAVEANIRH GLPLSLADRK RAAVQIIGTH  120
PQWSDRRVAS ATGISAGTVA DLRRRAGEDG TEARIGRDGR VRPSDGSERR RLAAELIRSD  180
PGLSLRQVAK QVGISPETVR DVRGRLERGE SPTPDGTRRL PAKPHPLRLS EPDFGRAVDQ  240
DRLALLERLK SDPALRLNEV GRILLRMLTM HSMDGQEWER ILQGVPPHLH GVIAGFARDH  300
ARVWAEFADH LESRATELAA G                                            321

SEQ ID NO: 26           moltype = AA  length = 311
FEATURE                 Location/Qualifiers
source                  1..311
                        mol_type = protein
                        organism = Streptomyces fungicidicus
SEQUENCE: 26
VEISSLSTDG SPRIDGESPE HVEMLAAADT ALPPIMVHRR TGRVIDGMHR LRAAMLTGRT  60
TIAVRFFDGT EEDAFVLAVK SNIAHGLPLS AADRRRAAGR IMATHPRWSD RMIASVVGTS  120
ARTVAEIRRD AGAAGAGEPT RIGRDGRVRP VDVSEGRRLA HDMIVRDPGL SLRQVARAAG  180
ISPETVRDVR HRMLRGEDPV PAPRPRTLVE RGADRRAEPA GKAAAPCGTE PPPAVVMKRL  240
RADPALRLNE NGRDLLRLLD IHTVRLEDWN RIIESVPPHR LETVAQLARS CADKWSEIAS  300
RIESNASHLA G                                                       311

SEQ ID NO: 27           moltype = DNA  length = 15
FEATURE                 Location/Qualifiers
misc_feature            1..15
                        note = Synthetic oligonucleotide primer
source                  1..15
                        mol_type = other DNA
                        organism = synthetic construct
SEQUENCE: 27
gtgtttaatt aatga                                                   15

SEQ ID NO: 28           moltype = AA  length = 321
FEATURE                 Location/Qualifiers
source                  1..321
                        mol_type = protein
                        organism = Amycolatopsis balhimycina
SEQUENCE: 28
MDPTRVDIFA LPAVEIELSR LSSASSPRTS GEDPEHVETL LSAEGELPPI LVHRPTMQVL  60
DGLHRLKVAR VRGDTKILAR LVDATESDAF VLAVEANIRH GLPLSLADRK RAAVQIIGTH  120
PQWSDRRVAS ATGISAGTVA DLRRRAGEDG TEARIGRDGR VRPSDGSERR RLAAELIRSD  180
PGLSLRQVAK QVGISPETVR DVRGRLERGE SPTPDGTRRL PAKPHPLRLS EPDFGRAVDQ  240
DRLALLERLK SDPALRLNEV GRILLRMLTM HSMDGQEWER ILQGVPPHLH GVIAGFARDH  300
ARVWAEFADH LESRATELAA G                                            321

SEQ ID NO: 29           moltype = AA  length = 395
FEATURE                 Location/Qualifiers
source                  1..395
                        mol_type = protein
                        organism = Streptomyces kasugaensis
SEQUENCE: 29
MAETVRADSP LKSSYRNVPA AEVQGSGLSV GQRTTRIAIS SLLAADSPRS AGENAEHIRL  60
LADSGARLPP IVVQRSTMRV IDGMHRLRAA ALRGETEIEV RFFDGAEEDS FLLAVRSNIA  120
HGLPLSQEER AAAAQRIIRS HAQWSNQAIG EVTGLDAKTI AALRRDAKDV PQLDARIGRD  180
GRVRPVDGAQ GRRLAGELMA EQPDAPLRKI AHAAGVSLGT ASDVRRRIRN GQDPVPAGRQ  240
KADPQPPARY AASEDRSGTT APRTGEQNRR VLLQKLRKDP SLRCNEAGRA LLRWLEVQAV  300
EGEDWERLLD SVPMHCAATI VELARRKDPS LRCNEAGRAL LRWLEVQAVE GEDWERLLDS  360
VPMHCAATIV ELARGCSGVW QDFAAQLERR GRASA                             395
```

```
SEQ ID NO: 30          moltype = AA  length = 367
FEATURE                Location/Qualifiers
source                 1..367
                       mol_type = protein
                       organism = Streptomyces niveus
SEQUENCE: 30
MTNSGDEEIT PASLKATRKG ERVSIGSLLP PSELVRSGES TEHIRVLAET DEDLPPIVVH  60
RGTRRVVDGM HRLWAARFRG DESIEVVFVD GSPADVFVLA VELNRAHGLP LTLDERKSAA  120
AQIMDSHPHW SDRKIARTTG LAASTVASLR SSSTAGTVGR RTGQDGRSRP NDGTDGRQRA  180
AALLARNPNA SLREVTRAAG ISVGTASDVR ARLRRGEPAL TARQQAVMKL RPAARNPNAS  240
LREVTRAAGI SVGTASDVRA RLRRGEPALT ARQQAVMKLR PAAAQRSGPD YGRVLENLRK  300
DPSLRFTDLG RRLLRLLDGS VPGSVEQIAQ IADGVPEHCR TVVVDMAREC AAAWQHLADQ  360
LADRDTA                                                            367

SEQ ID NO: 31          moltype = AA  length = 359
FEATURE                Location/Qualifiers
source                 1..359
                       mol_type = protein
                       organism = Streptomyces globosus
SEQUENCE: 31
MKSDSAQRAV ERSRRVVRID ELIPADSPRL NGIDRSHVQR LATVYASLPP VLVHRPTMRV  60
VDGMHRIGAA RLKGLDTVEV TFFEGAEEQV FLRSVAANIT NGLPLSVADR KTAAARILAS  120
HPTLSDRAVA AHVGLDAKTV AGVRTCSAAG SPLLNMRTGA DGRVHPLDRT AERLHAAALL  180
TQDPGLPLRS VVEQTGLSLG TAHDVRRRLL RGEDPVPQNR QSAMLEPGLA PQKKATAKPP  240
VGPAARPVPK VPPAVAGRPP VSPRSRAPLE ALRKLSNDPS LRHSDQGREL MRWLHNRFVV  300
DEAWRRRADA VPAHCVDSMA ELAQHCSDAW HRFAEEMVRR RHSAAADGSG LRTTQPTRR   359

SEQ ID NO: 32          moltype = AA  length = 329
FEATURE                Location/Qualifiers
source                 1..329
                       mol_type = protein
                       organism = Actinoplanes teichomyceticus
SEQUENCE: 32
MTPDEEALNR QPIMEMEISS LSLGGSPRLA GGDPVHLEAM VAAQGELPPI VVHRPTMRVI  60
DGSHRIQAAL RRGETTIAGR FFDGSDDEAF VMSVWLNVSH GLPLALADRK RAAERIAVSH  120
PQWSDRRVAA VTGISPSTVA DIRRRVAGTS APEASRIGQD GRVRPLDCSA GRLLAGRLMA  180
ENPALSLRQV AKAAAISPET ARDVRNRLLS GAELVPNRRP RDAAPVGVKG GRDRRPLNLI  240
RSGDRPEPVP DHAVVINRLM SDPALRYTDT GRNLLRLLSL HTRWAKEWEA IVDNLPPHCA  300
DAVADLARQF ADLWADFASR VGPEERMAS                                    329

SEQ ID NO: 33          moltype = AA  length = 221
FEATURE                Location/Qualifiers
source                 1..221
                       mol_type = protein
                       organism = Streptomyces coelicolor
SEQUENCE: 33
MTIRLLIVDD QELIRTGFRL FLQTQNDLEV VGEADDGHGA LAQAAALRPD VVLMDIRMPR  60
MDGVEATSRL TASDSPPRVL ILTTYDLDEY VFGALRAGAS GFLLKDASRD RLLEAIRVVH  120
AGEALLSPSI TRRLIEDYAT RAAPVRPREA VLAGLTPRER EILLLVARGL SNPEIAARLV  180
VTEATVKSHV GSMFAKLHLR DRAQAVVFAY ENAIVLPGGT G                      221

SEQ ID NO: 34          moltype = AA  length = 222
FEATURE                Location/Qualifiers
source                 1..222
                       mol_type = protein
                       organism = Streptomyces coelicolor
SEQUENCE: 34
MIRVLLADDE TIIRAGVRSI LTTEPGIEVV AEASDGREAV ELARKHRPDV ALLDIRMPEM  60
DGLTAAGEMR TTNPDTAVVV LTTFGEDRYI ERALDQGVAG FLLKASDPRD LISGVRAVAS  120
GGSCLSPLVA RRLMTELRRA PSPRSEVSGE RTTLLTKREQ EVLGMLGAGL SNAEIAQRLH  180
LVEGTIKTYV SAIFTQLEVR NRVQAAIIAY EAGLVKDADL NR                     222

SEQ ID NO: 35          moltype = AA  length = 218
FEATURE                Location/Qualifiers
source                 1..218
                       mol_type = protein
                       organism = Streptomyces coelicolor
SEQUENCE: 35
MREDGKIRVF LLDDHEVVRR GVHDLLSGEA DIEVVGEAGT AAEAQARVTA TRPDVAVLDV  60
RLPDGSGVEV CRDIRSRDES VRCLMLTSFA DDEALFDAIM AGASGYVLKD IRGAELLGAV  120
REVAAGKSLL DPAATARVLE RLRGGGARPD DRLARLTEQE RRILELIGEG LTNRAIGERL  180
HLAEKTIKNY VSSLLGKLGM QRRSQAAAFV ARLEAENR                          218

SEQ ID NO: 36          moltype = AA  length = 220
FEATURE                Location/Qualifiers
source                 1..220
                       mol_type = protein
                       organism = Streptomyces fungicidicus
```

```
SEQUENCE: 36
VSVLLEQPAS LVAYRPNKPT AMVVVADPRV RSTVTRHLWA LGVRDVIEAS SVAEARPRIG  60
NPRDICVAEV HLPDGSGLTL LSETRAAGWP NGLALSAADD IGAVRNALAG GVKGYVVTGT  120
RTNLGLPTRP GAAPIGAAAA RLHRRPPGAP SHPGGYRELS GREVEVLRLV AEGQSNKAIG  180
VSMGLSALTV KSHLARIARK LGTGDRAGMV AVALRTGIIH                       220

SEQ ID NO: 37          moltype = DNA  length = 663
FEATURE                Location/Qualifiers
source                 1..663
                       mol_type = other DNA
                       organism = Streptomyces fungicidicus
SEQUENCE: 37
gtgtccgttc tcctcgagca gcccgcaagc ctggtcgcct accgcccgaa caagccgacc  60
gccatggtgg tcgtggccga cccccgcgtc cgttcgaccg tcacccgcca cctgtgggcg  120
ctcggcgtac gcgacgtcat cgaggcctcg tccgtcgcgg aggctcgtcc ccgcatcggc  180
aacccccgcg acatctgcgt cgccgaagtc catctgccgg atggttccgg cctcaccctc  240
ctctccgaga cccgcgccgc gggctggccc aacggcctcg ccctctccgc ggcggacgac  300
atcggcgccg tgcgcaacgc cctcgcgggc ggagtcaagg gctacgtcgt caccggcacc  360
cgcaccaacc tcgggctccc cacccggccg ggtgccgctc ccatcggcgc cgccgccgcg  420
cgcctgcacc gccgcccccc gggtgccccg agccacccgg gcggctaccg cgagctgtcc  480
ggccgcgagg tggaggtgct gcggctggtg gcggaaggcc agtcgaacaa ggcgatcggc  540
gtctcgatgg gcctgtccgc actgaccgtc aagagccacc tggcccggat cgcccgcaag  600
ctcggcacgg gcgaccgcgc cggcatggtg gccgtggccc tgcgcaccgg catcatccac  660
tga                                                               663

SEQ ID NO: 38          moltype = DNA  length = 936
FEATURE                Location/Qualifiers
source                 1..936
                       mol_type = other DNA
                       organism = Streptomyces fungicidicus
SEQUENCE: 38
gtggaaataa gttcgctctc caccgacggc tccccgcgga tcgacgggga gagtcccgag  60
cacgtggaaa tgctggccgc cgccgacacc gcgcttccac cgatcatggt gcaccgccgc  120
accgggcggg tcatcgacgg catgcaccgg ctgcgcgccg cgatgctgac gggccgtacg  180
acgatcgcgg tgaggttctt cgacggcacc gaggaggacg ccttcgtcct cgccgtgaag  240
tcgaacatcg cgcacggact gccgctgtcc gccgccgacc gccggcgggc cgccgggcgc  300
atcatggcca cccatccccg gtggtcggac cggatgatcg cctcggtggt cggcacctcc  360
gccaggacgg tcgccgagat ccgccgcgac gccggcgccg ccggggcggg ggagcccacc  420
cgcatcggcc gggacggcag ggtacggccc gtcgacgtga gcgagggccg cagactggcc  480
cacgacatga tcgtccgcga cccgggcctg tcgctgcgcc aggtcgcccg cgccgccggg  540
atctcgccgg agaccgtcag ggacgtcaga caccggatgc tccgcggtga ggacccggtg  600
cccgcgccgc ggccgcggac cctggtggag cgcggcgcgg accgccgggc ggagccggcc  660
gggaaggccg ccgcgccgtg cgggacggag ccgccgcccg ccgtcgtgat gaagcggctg  720
agggccgatc cggcgctgcg tctcaacgag aacggacgcg acctgctgcg gcttctggat  780
atccacacgg tccggctgga ggactggaac cgcattatcg aaagcgtgcc gccgcaccgt  840
ctggagacgg tggcgcagct ggcacgctcc tgcgccgaca aatggtccga gatcgcgtca  900
cgcatcgaaa gcaacgcatc acatctggcc gggtga                           936

SEQ ID NO: 39          moltype = DNA  length = 39331
FEATURE                Location/Qualifiers
misc_feature           1..39331
                       note = Synthetic the fosmid pXYF148
source                 1..39331
                       mol_type = other DNA
                       organism = synthetic construct
SEQUENCE: 39
atcgaatata acttcgtata atgtatgcta tacgaagtta ttagcgatga gctcggactt  60
ccattgttca ttccacggac aaaaacagag aaaggaaacg acagaggcca aaaagctcgc  120
tttcagcacc tgtcgtttcc tttcttttca gagggtattt taaataaaaa cattaagtta  180
tgacgaagaa gaacggaaac gccttaaacc ggaaaatttt cataaatagc gaaaacccgc  240
gaggtcgccg ccccgtaacc tgtcggatca ccggaaagga cccgtaaagt gataatgatt  300
atcatctaca tatcacaacg tgcgtggagg ccatcaaacc acgtcaaata atcaattatg  360
acgcaggtat cgtattaatt gatctgcatc aacttaacgt aaaaacaact tcagacaata  420
caaatcagcg acactgaata cggggcaacc tcatgtccga gctcgcgagc tcgtcgacag  480
cgacacactt gcatcggatg cagcccggtt aacgtgccgg cacggcctgg gtaaccaggt  540
attttgtcca cataaccgtg cgcaaaatgt tgtggataag caggacacag cagcaatcca  600
cagcaggcat acaaccgcac accgaggtta ctccgttcta caggttacga cgacatgtca  660
atacttgccc ttgacaggca ttgatggaat cgtagtctca cgctgatagt ctgatcgaca  720
atacaagtgg gaccgtggtc ccagaccgat aatcagaccg acaacacgag tgggatcgtg  780
gtcccagact aataatcaga ccgacgatac gagtgggacc gtggtcccag actaataatc  840
agaccgacga tacgagtggg accgtggttc cagactaata atcagaccga cgatacgagt  900
gggaccgtgg tcccagacta ataatcagac cgacgatacg agtgggacca tggtcccaga  960
ctaataatca gaccgacgat acgagtggga ccgtggtccc agtctgatta tcagaccgac  1020
gatacgagtg ggaccgtggt cccagactaa taatcagacc gacgatacga gtgggaccgt  1080
ggtcccagac taataatcag accgacgata cgagtgggac cgtggtccca gtctgattat  1140
cagaccgacg atacaagtgg aacagtgggc ccagagagaa tattcaggcc agttatgctt  1200
tctggcctgt aacaaaggac attaagtaaa gacagataaa cgtagactaa aacgtggtcg  1260
catcagggtg ctggcttttc aagttcctta agaatggcct caattttctc tatacactca  1320
gttggaacac gagacctgtc caggttaagc accattttat cgcccttata caatactgtc  1380
```

```
gctccaggag caaactgatg tcgtgagctt aaactagttc ttgatgcaga tgacgtttta  1440
agcacagaag ttaaaagagt gataacttct tcagcttcaa atatcacccc agcttttttc  1500
tgctcatgaa ggttagatgc ctgctgctta agtaattcct ctttatctgt aaaggctttt  1560
tgaagtgcat cacctgaccg ggcagatagt tcaccggggt gagaaaaaag agcaacaact  1620
gatttaggca atttggcggt gttgatacag cgggtaataa tcttacgtga aatattttcc  1680
gcatcagcca gcgcagaaat atttccagca aattcattct gcaatcggct tgcataacgc  1740
tgaccacgtt cataagcact tgttgggcga taatcgttac ccaatctgga taatgcagcc  1800
atctgctcat catccagctc gccaaccaga acacgataat cactttcggt aagtgcagca  1860
gctttacgac ggcgactccc atcggcaatt tctatgacac cagatactct tcgaccgaac  1920
gccggtgtct gttgaccagt cagtagaaaa gaagggatga gatcatccag tgcgtcctca  1980
gtaagcagct cctggtcacg ttcattacct gaccataccc gagaggtctt ctcaacacta  2040
tcaccccgga gcacttcaag agtaaacttc acatcccgac cacatacagg caaagtaatg  2100
gcattaccgc gagccattac tcctacgcgc gcaattaacg aatccaccat cggggcagct  2160
ggtgtcgata acgaagtatc ttcaaccggt tgagtattga gcgtatgttt tggaataaca  2220
ggcgcacgct tcattatcta atctcccagc gtggtttaat cagacgatcg aaaatttcat  2280
tgcagacagg ttcccaaata gaaagagcat ttctccaggc accagttgaa gagcgttgat  2340
caatggcctg ttcaaaaaca gttctcatcc ggatctgacc tttaccaact tcatccgttt  2400
cacgtacaac atttttttaga accatgcttc cccaggcatc ccgaatttgc tcctccatcc  2460
acggggactg agagccatta ctattgctgt atttggtaag caaaatacgt acatcaggct  2520
cgaacccttt aagatcaacg ttcttgagca gatcacgaag catatcgaaa aactgcagtg  2580
cggaggtgta gtcaaacaac tcagcaggcg tgggaacaat cagcacatca gcagcacata  2640
cgacattaat cgtgccgata cccaggttag gcgcgctgtc aataactatg acatcatagt  2700
catgagcaac agtttcaatg gccagtcgga gcatcaggtg tggatcggtg ggcagtttac  2760
cttcatcaaa tttgcccatt aactcagttt caatacggtg cagagccaga caggaaggaa  2820
taatgtcaag ccccggccag caagtgggct ttattgcata agtgacatcg tccttttccc  2880
caagatagaa aggcaggaga gtgtcttctg catgaatatg aagatctggt acccatccgt  2940
gatacattga ggctgttccc tgggggtcgt taccttccac gagcaaaaca cgtagcccct  3000
tcagagccag atcctgagca agatgaacag aaactgaggt tttgtaaacg ccacctttat  3060
gggcagcaac cccgatcacc ggtggaaata cgtcttcagc acgtcgcaat cgcgtaccaa  3120
acacatcacg catatgatta atttgttcaa ttgtataacc aacacgttgc tcaacccgtc  3180
ctcgaatttc catatccggg tgcggtagtc gccctgcttt ctcggcatct ctgatagcct  3240
gagaagaaac cccaactaaa tccgctgctt cacctattct ccagcgccgg gttattttcc  3300
tcgcttccgg gctgtcatca ttaaactgtg caatggcgat agccttcgtc atttcatgac  3360
cagcgtttat gcactggtta agtgtttcca tgagtttcat tctgaacatc ctttaatcat  3420
tgctttgcgt ttttttatta aatcttgcaa tttactgcaa agcaacaaca aaatcgcaaa  3480
gtcatcaaaa aaccgcaaag ttgtttaaaa taagagcaac actacaaaag gagataagaa  3540
gagcacatac ctcagtcact tattatcact agcgctcgcc gcagccgtgt aaccgagcat  3600
agcgagcgaa ctggcgagga agcaaagaag aactgttctg tcagatagct cttacgctca  3660
gcgcaagaag aaatatccac cgtgggaaaa actccaggta gaggtacaca cgcggatagc  3720
caattcagag taataaactg tgataatcaa ccctcatcaa tgatgacgaa ctaacccccg  3780
atatcaggtc acatgacgaa gggaaagaga aggaaatcaa ctgtgacaaa ctgccctcaa  3840
atttggcttc cttaaaaatt acagttcaaa aagtatgaga aaatccatgc aggctgaagg  3900
aaacagcaaa actgtgacaa attaccctca gtaggtcaga acaaatgtga cgaaccaccc  3960
tcaaatctgt gacagataac cctcagacta tcctgtcgtc atggaagtga tatcgcggaa  4020
ggaaaatacg atatgagtcg tctggcggcc tttctttttc tcaatgtatg agaggcgcat  4080
tggagttctg ctgttgatct cattaacaca gacctgcagg aagcggcggc ggaagtcagg  4140
catacgctgg taactttgag gcagctggta acgctctatg atccagtcga ttttcagaga  4200
gacgatgcct gagccatccg gcttacgata ctgacacagg gattcgtata aacgcatggc  4260
atacggattg gtgatttctt ttgtttcact aagccgaaac tgcgtaaacc ggttctgtaa  4320
cccgataaag aagggaatga gatatgggtt gatatgtaca ctgtaaagcc ctctggatgg  4380
actgtgcgca cgtttgataa accaaggaaa agattcatag cctttttcat cgccggcatc  4440
ctcttcaggg cgataaaaaa ccacttcctt ccccgcgaaa ctcttcaatg cctgccgtat  4500
atccttactg gcttccgcag aggtcaatcc gaatatttca gcatatttag caacatggat  4560
ctcgcagata ccgtcatgtt cctgtagggt gccatcagat tttctgatct ggtcaacgaa  4620
cagatacagc atacgttttt gatcccggga gagactatat gccgcctcag tgaggtcgtt  4680
tgactggacg attcgcgggc tatttttacg tttcttgtga ttgataaccg ctgtttccgc  4740
catgacagat ccatgtgaag tgtgacaagt ttttagattg tcacactaaa taaaaaagag  4800
tcaataagca gggataactt tgtgaaaaaa cagcttcttc tgagggcaat ttgtcacagg  4860
gttaagggca atttgtcaca gacaggactg tcatttgagg gtgatttgtc acactgaaag  4920
ggcaatttgt cacaacacct tctctagaac cagcatggat aaaggcctac aaggcgctct  4980
aaaaaagaag atctaaaaac tataaaaaaa ataattataa aaatatcccc gtggataagt  5040
ggataacccc aagggaagtt ttttcaggca tcgtgtgtaa gcagaatata taagtgctgt  5100
tccctggtgc ttcctcgctc actcgaccgg gagggttcga gaagggggggg cacccccctt  5160
cggcgtgcgc ggtcacgcgc acagggcgca gccctggtta aaaacaaggt ttataaatat  5220
tggtttaaaa gcaggttaaa agacaggtta gcggtggccg aaaaacgggc ggaaaccctt  5280
gcaaatgctg gattttctgc ctgtggacag cccctcaaat gtcaataggt gcgcccctca  5340
tctgtcagca ctctgcccct caagtgtcaa ggatcgcgcc cctcatctgt cagtagtcgc  5400
gcccctcaag tgtcaatacc gcagggcact tatccccagg cttgtccaca tcatctgtgg  5460
gaaactcgcg taaaatcagg cgttttcgcc gatttgcgag gctggccagc tccacgtcgc  5520
cggccgaaat cgagcctgcc cctcatctgt caacgccgcg ccgggtgagt cggcccctca  5580
agtgtcaacg tccgcccctc atctgtcagt gagggccaag ttttccgcga ggtatccaca  5640
acgccggcgg ccggccgcgg tgtctcgcac acggcttcga cggcgtttct ggcgcgtttg  5700
cagggccata gacggccgcc agcccagcgg cgagggcaac cagccgaggg cttcgccctg  5760
tcgctcgact gcggcgagca ctactggctg taaaaggaca gaccacatca tggttctgtg  5820
ttcattaggt tgttctgtcc attgctgaca taatccgctc cacttcaacg taacaccgca  5880
cgaagatttc tattgttcct gaaggcatat tcaaatcgtt ttcgttaccg cttgcaggca  5940
tcatgacaga acactacttc ctataaacgc tacacaggct cctgagatta ataatgcgga  6000
tctctacgat aatgggagat ttcccgact gtttcgttcg cttctcagtg gataacagcc  6060
agcttctctg tttaacagac aaaaacagca tatccactca gttccacatt tccatataaa  6120
```

```
ggccaaggca tttattctca ggataattgt ttcagcatcg caaccgcatc agactccggc  6180
atcgcaaact gcacccggtg ccgggcagcc acatccagcg caaaaacctt cgtgtagact  6240
tccgttgaac tgatggactt atgtcccatc aggctttgca gaactttcag cggtataccg  6300
gcatacagca tgtgcatcgc ataggaatgg cggaacgtat gtggtgtgac cggaacagag  6360
aacgtcacac cgtcagcagc agcggcggca accgcctccc caatccaggt cctgaccgtt  6420
ctgtccgtca cttcccagat ccgcgctttc tctgtccttc ctgtgcgacg gttacgccgc  6480
tccatgagct tatcgcgaat aaatacctgt gacggaagat cacttcgcag aataaataaa  6540
tcctggtgtc cctgttgata ccgggaagcc ctgggccaac ttttggcgaa aatgagacgt  6600
tgatcggcac gtaagaggtt ccaactttca ccataatgaa ataagatcac taccgggcgt  6660
atttttttgag ttatcgagat tttcaggagc taaggaagct aaaatggaga aaaaaatcac  6720
tggatatacc accgttgata tatcccaatg gcatcgtaaa gaacattttg aggcatttca  6780
gtcagttgct caatgtacct ataaccagac cgttcagctg gatattacgg cctttttaaa  6840
gaccgtaaag aaaaataagc acaagtttta tccggccttt attcacattc ttgcccgcct  6900
gatgaatgct catccggaat ttcgtatggc aatgaaagac ggtgagctgg tgatatggga  6960
tagtgttcac ccttgttaca ccgttttcca tgagcaaact gaaacgtttt catcgctctg  7020
gagtgaatac cacgacgatt tccggcagtt tctacacata tattcgcaag atgtggcgtg  7080
ttacggtgaa aacctggcct atttccctaa agggtttatt gagaatatgt ttttcgtctc  7140
agccaatccc tgggtgagtt tcaccagttt tgatttaaac gtggccaata tggacaactt  7200
cttcgccccc gttttcacca tgggcaaata ttatacgcaa ggcgacaagg tgctgatgcc  7260
gctggcgatt caggttcatc atgccgtttg tgatggcttc catgtcggca gaatgcttaa  7320
tgaattacaa cagtactgcg atgagtggca gggcggggcg taattttttt aaggcagtta  7380
ttggtgccct taaacgcctg gttgctacgc ctgaataagt gataataagc ggatgaatgg  7440
cagaaattcg atgataagct gtcaaacatg agaattggtc gacggcccgg gcggccgcaa  7500
ggggttcgcg ttggccgatt cattaatgca gctggcacga caggtttccc gactggaaag  7560
cgggcagtga gcgcaacgca attaatgtga gttagctcac tcattaggca ccccaggctt  7620
tacactttat gcttccggct cgtatgttgt gtggaattgt gagcggataa caatttcaca  7680
caggaaacag ctatgaccat gattacgcca agctatttag gtgagactat agaatactca  7740
agcttgcatg cctgcaggtc gactctagag gatcccacca ccgccggacg gggtcgccg  7800
gcccggaagt ccaccaggat cgagccgccg atctgccgcc cgcgccacca cgactccatc  7860
agcccgacct cctcctccgg gctgcgcacc agccgcagca gcagcgagca ggaccgctcc  7920
accaggacgc tctccacccc ggagatgaac tccatgtaga acggctccag gccgagcagc  7980
cgggcgggcc ggcagaccgc gagacccacc acgtccaccc gcgacccggc cagcgtgcgc  8040
gcggttcggc tcggcgccca ccccagctcc cgcgccgccc ggaagatgcg gtcccgggtc  8100
gcctccgaca gcccgggctt ccggttgaag gcgagggaca cggcgccctt ggacacgccg  8160
gcgcgcgcgg cgacgtccct gatggtgacg cgaggggtcg gcgttgccgt catcgagtgg  8220
gctccacgca gtacagggcg gaacgggcgg tgtccgggtc cggagtcttc cacccccgca  8280
ccccgatggt cacctgttcc ccggggagca gggtcaccag cccccggtcg gcccgcgccc  8340
cggggtccag ccggtcggcc tggagcagca ggtcccgtac gagggtgcgg gccgtgaccg  8400
tgatcccgtc cggcgcgagg gcgacctcga actccggcgg ggggtagggg atctcccggt  8460
ccggcgccgg gaagtgccac gcccgcaccc cgtccgcgtc ggcgaccagg aactccccgg  8520
ggccgtccgg cagcagttcg accgggacct cgaccacggc caccgtccgc cccccggcgt  8580
ccagcgccgg ggccgcctcc gcgatcgggg cgccgtcgac ggacatccgg cgcagccgca  8640
gcgttccccg ccagtcctcc gcggactggt tgaccgccgc caccaccaga ccgtcaccgt  8700
ccgcgcgcac ggtcagcagc cggtccgcgt acagccggcg cagctcgtgg tagagcggct  8760
tctcccgccc gtccccgtcg atcgcggccc acgacgtcac cggccagcag tcgttgagct  8820
gccagaccac cgtgcccgcg cacaccggcc agtgcgagcg ccagtgctcg acaccggccg  8880
ccaccgcacg cgcctggttg acctgcgtca gatagtgcca gcggtcgaag tcgccctccg  8940
gcacggcgaa gtggcgggcg aggccgcgct ccagcttgcc gttgccgtcc tccgccttct  9000
ggtggtgcag catgccgggg gagtccggcg cggggtcctc cccgggcagc gcccgccgca  9060
gcgtggcgtg cgcgggaggc gcctgccagc cgaactcggc cacgaagcgc gggacgtcgc  9120
gccggtagtc ggcgtagtcg gcgcggttcc acacctccca ggagtggtgg gtgccgtgcg  9180
ccggatcgtt ggggtggtgc cgccaggaac cggaccaggg actgcccgcc gtgtacggcc  9240
gcgtcgggtc cagctccgcg accacccgcg gcaggacgcc gaggtagtag ccctcgcccc  9300
aggagtcccc ggcgagcccc tgctcccagt cccagtcccg gaacccccac aggttctcgt  9360
tgttgccgtt ccacagcacc agggaggggt gcggcatcag ccgtacgacg ttctcccggg  9420
cctccgcctc cacctccccg cgcagcggct gctcctcggg gtaggcggcg cacgcgaacg  9480
ggaagtcctg ccagaccagc agccccaact cgtcgcaggc gtcgtagaag tcctcgtcct  9540
cgtagatccc gccgccccag acccggacca ggtccaccc cgcgccggcc gcctgctcca  9600
gccggtgccg gtagcgctcc cgggtgatcc gggacgggaa cacgtcgtcc gggatccagt  9660
tgacgccccg cgcgaacagc cgctcaccgt tgacgaccag ggtgaacccg gtgccgtgcg  9720
cgtcggccga ggtgtccagc tcaaccgtcc ggaacccggt cctgcgccgc caggcgtcca  9780
gcgcctcgtc accgtgggac aacgtcagct cgacgtcgta cagcggctgt tcgccgtatc  9840
cgcgcggcca ccacaggcgg acgtccggca cccggagccg cacggtcccg gccgtcccat  9900
cgacccgcgc ccgggcgcgc acgcccccgg cgctcgcctc cagggtgagc ggtgcctcga  9960
cccgggagcg ctccacgtcg accgccagct cgatctgccc caccccgtcc tcgacggtga  10020
ccagcgggcg cacccgggcg atccgcgccg tcgaccagcg ctccagccgc accggccgcc  10080
agatcccggc cgtcaccagc gtcggccccc agtcccagcc gaacgagcag gccatcttcc  10140
gcaggtactg gtacggctcg gcgtacgctc cggggcgctc gcccagcctg ccgcgcaccg  10200
cctccgcctc ggcgtacgcg gaggcgaacc gcaccgtgag ccggccgctc agtcccgtca  10260
cgtcgaagcg gtacgagcgg tgcatgttcc gcgtccggcc cagtggccgg ccgtcgagca  10320
ggatctcggc gacggtgtcg agaccgtcga agacgaggtc cgtctgctcg tgcgggcccg  10380
tcccggcggt cagctccgtc tcgtacgtcc actcccgccg gcccacccag gccacctcgg  10440
tctcgttgcg gccgaggaac ggatcgggga tcagcccggc cgccagcaga tcggtgtgca  10500
cacaccccgg caccgaggcg gggagggcgt cccccgtgcc gtccgggtgt cgcaggatcc  10560
atccctcggt gagcggtgtg acctgacgca tgcacactcc ctaaaccggt tgagccttct  10620
ctgaagagtg gtctggcatc gttggcgcga ttgcgacttt accggttcag ttcagggctg  10680
ccagagtgcc gaatcagcca tcccactcgt gctcgtccgt cccgtgaacg gagccgtgat  10740
gcatctgaac cgccgtacga cactcaccgg atcgctcgcc ctgctcgccc tcctggcctc  10800
cgcctgcacg ggcacggggg gttcctcgaa gggcgcggac gccaaggctc ccgacgaccc  10860
```

-continued

```
gtcaaaggtc aaggggtccc tcacggtcct cacccaccgg accgatctgg tgcaggacgg  10920
gacgatgaag aagtacgccg ccgagttcaa cgagacctat cccggggtga aggtggagtt  10980
cgacggcctc accgactacg agggcgaggt caagatccgt atgaacacgg agaactacgg  11040
cgacgtcctc atgatcccgg cggtcgtcga gaagaaggac tacccgaagt tcttcgcctc  11100
cctgggcacc aaggccgaac gcgccgccaa gtaccggttc accgactact ccaccgtcga  11160
cggcaaggtc tacgggcaga gccccgtcgg cgtcgtcccc gggttcatct acaacaagcg  11220
ggtgtggagc gaggccggcg tcaccgactg gcccaccacc cccgccgagt tcctggacga  11280
cctgaaggcg atccggtcga agaccgacgc ggtgccgtac tacaccaact tcaaggacat  11340
gtggccgctg acccagtgga ccaacgtcaa cggctccgtc ggctgcgacc cgcacgccac  11400
cacgaagctc gccgagggcg acccgtgggc cgaggggggcc gacctgcgcg tgggcgacac  11460
cctgctccac gacatcgtgc gcggcggact cgccgagaag gacccgacca ccaccaactg  11520
ggagggctcc aagcccaagc tggccaaggg cgagatcgcc accatgtggc tgggctcctg  11580
ggccgtcgtg cagatgcggg acgcggcgaa gcaggccggc gccgaccccg ccgacatcgg  11640
cttcatgccc ttccccgcac agcgggacgg cacgttctgc gcggtgacct ccccggacta  11700
ccagcaggcg gtcaacgtca actccgacaa caaggaggcc gcccgcgcct ggatcgactg  11760
gttcaccgac aagtccggct acgccgaggc caacctcgcc ctatcccccc tgaaggacgc  11820
cccgctgccc gccgtcctcg agccctacga gaaggccggc gtgaagctcc tggacctcga  11880
ggacagcaag ggcgccgagg tgaagtccct cgacaaccgc tccgaggtcg gcatctacaa  11940
gcccgactac cgccaggaac tcgtcgacct cgcccgcggc gcccgcaagg gcggcctgga  12000
cgactacctc ggcggcctcg gcgagcgctg ggccgaggcg cgcagcgcgc tgggggcctg  12060
atgacggaca ccacccgcaa ggcggcgcgg ccggttcccc cggccgcgcc cgccgggccg  12120
ggccgcgcgg cgccggcccc gcgccgcacc cggctgtcgc gccgcctcac cccgtggctg  12180
ttcctggccg caccgctggc cctgctcctg accttcacct acgcgcccga tcgccaacat  12240
ggtcgcgtac agcttcaccg actgggacgg cgtgagcccg gagctgaact ggacgggcac  12300
cgggaactac accgaactcc tcacccgctc cgagctgttc gaggtcttct tcgtcagcgg  12360
ctactacctc gtcgcctccg cggtgcagat cgtgctcgcc ctctacttcg ccacggtcct  12420
cagcttcgac gtccgcttcc ggaacttctt caagggcgtg ctgttcttcc cgtacctcat  12480
caacggggtg gccatcggct tcgtcttcct ctacttcttc caggacggcg gcaccctcga  12540
ctccgtactg ggcctgctcg gcgtcgagac cgaccacgcc tggctgggca cgccgttctc  12600
cgcgaacacc tcgctggccg gcgtctccgt ctggcgctac ctcggactga acttcgtcct  12660
cttcctcggc gcgatccagt ccatcccggg cgagctgtac gaggcggccg agatcgacgg  12720
cgcgaaccgc tggcagcagt tccggcacat catcgcgccc ggcatcagac ccgtgctgag  12780
cctgagcgtg atcctctcgg tctccggctc gctgtcggtc ttcgagatcc cgtacatcat  12840
gaccggcggc gccaccggca cggagacctt cgtgatccag accgtgaagc tggcgttcca  12900
gttcaacaag acgggactcg cctcggccgc cgccgtcgtc ctgctgctga tcgtcctggc  12960
ggtcacctgg gtgcagcggc gcatcgtccc cgacgagaag gtggacctcg tatgacccgc  13020
cgtaccgcgg cacgcgccct ggtcctgacg tccctgatcc tggcgacgct ggtggtgctg  13080
ctgccgctcg ccgtggtctt cctgacctcg ctgaagtcct ccgaggagat ggcgaacggc  13140
agcggagcgc tgacgccgcc cgacgacccg ctgaacttcg gcaactacgt gacggcgttc  13200
cgggacggcc agatgctgtc cgcgttcggg aacacggccg tcatcctggt cgtggccgtc  13260
ggcggaacga tcctgatcgg ctcgatgacg gcgtacgcga tcgaccgctt ccggttccgc  13320
ttcaagaagc tggtcgtggc gctgttcctg ctggccgcgc tggtccccgg ggtgaccacc  13380
caggtggcga ccttccagat cgtcaacagc ttcggcatgt tcgacagcct gtgggcgccg  13440
atcgccctct acatgggcac ggacatcgtc tcgatctacg tcttcctgca gttcatccgc  13500
tccatccccg tctccctgga cgaggcggcg cgcctggacg gcgccaacgc gttcaccgtc  13560
taccgcaagg tgatcttccc gctgctcaag ccggcgatcg cgacggtggt gatcgtaaag  13620
gggatcaacg tctacaacga cttctacatc cccttcctct acatgccctc cgaggacctg  13680
ggggtcatct cgacgtccct gttccgcttc aagggcccct tcggcgcgca ctgggagacg  13740
atctcggcgg gcgcggtcct ggtcatcctg cccaccttga tcgtcttcct gttcctccag  13800
cgcttcatct acaacgggtt catgcggggg gcgacgaagt agccagcgcg gccaccagca  13860
cgggagtgac ctggtcgacc tgccacgcgc gtgccccgtg cgccgtcagc gccgcggcga  13920
cggaccgctc gtcgggcccc ggcggctccc agcagaccct gcgcaccgtg tccggggtga  13980
tcaggttctc cggcggcatg ttcagccgct cggcgagttc ggcgaccccc gcgcgggccg  14040
ccgacagccg ggccgcggca acggggtcct tgtccgccca ggcgcgcggc ggcggagggc  14100
cggtcaccgg ctggccgggc tgcggcagct gggcctcgct cagcgccttc gcgcggtcga  14160
cggccgcctg ccactgctcc agctggcgcc gccccacccg ctgcccgaac ccgttgagcg  14220
cggccatggc gtgcaggttg gcgggcagcg cgagcgcggc ctccacgatc gccgcgtcgg  14280
aaagcacctt gccgggggag acgtcacggc gccgggcgat ccggtcgcgg gtctcccaca  14340
gctcccgcac caccgccatc tggcggcgcc ggcgcacctt gtgcatgccg gaggtgcggc  14400
gccaggggtc cttgcggggc tccggcggcg gggccgaggc gatcgcgtcg aactcctgcc  14460
gggcccagtc cagcttgccc tggcggtcca gctccttctc cagggcgtcc cgcagatcga  14520
ccagcagttc gacgtcgagg gcggcgtacc gcagccaggg ctcgggcagc ggacgggtgg  14580
accagtcgac ggcggagtgg cccttctcca ggacgaagcc gagcacgttc tcgaccatcg  14640
cgccgagccc gacgcggggg aacccggcaa ggcggccggc cagctcggtg tcgaagaggc  14700
gggagggcac catgcctatc tcgcgcagac agggcaggtc ctgggtggcg gcgtgcagca  14760
cccactcgac gccggacagc gcctcgccga gggcggacag gtcggggcag gccacggggt  14820
cgatcagcgc ggtacccgca ccctcgcggc gcagctggac gaggtaggcg cgctggccgt  14880
agcggtaccc ggaggcgcgc tcggcgtcca cggcgacggg tccgctgccg gccgcgaagg  14940
cggcgaccgc ctcggcgagg gcggcctcgt ccgctatcac gggcggaatg ccctcgcggg  15000
gttccagcaa gggggtcggc gcctccgtaa cagaagatcc gccgtcgtcc ggaggagcgc  15060
ctccggtggt gcgcagtgaa ctgtctgctg cggtgtcgtg ggcgtcggtc acctgtcaag  15120
ggtatccgtg ccgcgaaggc gcccgtcgac ggttgtgctc cgtgacgggc gccggtgggt  15180
cgtattccgg tcagaagagt gaaagaacgt gttcgcttgg ccgtgggcgg gcggatcggg  15240
gacgggcgga tcgggggcgg gacggaaggg tcagtggatg atgccggtgc gcagggccac  15300
ggccaccatg ccggcgcggt cgcccgtgcc gagcttgcgg gcgatccggg ccaggtggct  15360
cttgacggtc agtgcggaca ggcccatcga gacgccgatc gccttgttcg actggccttc  15420
cgccaccagc cgcagcacct ccacctcgcg gccggacagc tcgcggtagc cgcccgggtg  15480
gctcggggca cccggggggc ggcggtgcag gcgcgcggcg gcggcgccga tgggagcggc  15540
acccggccgg gtggggagcc cgaggttggt gcgggtgccg gtgacgacgt agcccttgac  15600
```

-continued

```
tccgcccgcg agggcgttgc gcacggcgcc gatgtcgtcc gccgcggaga gggcgaggcc  15660
gttgggccag cccgcggcgc gggtctcgga gaggagggtg aggccggaac catccggcag  15720
atggacttcg gcgacgcaga tgtcgcgggg gttgccgatg cggggacgag cctccgcgac  15780
ggacgaggcc tcgatgacgt cgcgtacgcc gagcgcccac aggtggcggg tgacggtcga  15840
acggacgcgg gggtcggcca cgaccaccat ggcggtcggc ttgttcgggc ggtaggcgac  15900
caggcttgcg ggctgctcga ggagaacgga caccaggcct cctggggtgc gggacgggcc  15960
ggctcgtggg ggtgaaggcg ggacgaaccg tgctttcaag gtcacagtcg tcttcggcag  16020
caaacctggt gtcctttaac gaatgatcac gaagtgatga gtaacaatcc gggcaattcg  16080
gacgcacgat cgatcattcg aagatcgaac ggtttcggtc tgcgtcgcaa cgcttccgaa  16140
agtggccgta tcgacaaaga gagatgcagg aggccggtcg tcgggacccc gcagcgggag  16200
gctcagcgcg actgcggccc cctccgctgc ggcagcgtca ccacggacgc gtcccccgga  16260
gcggccggcg gcagccccgc gacctgcgcc agcagatcgg accacgcgac cagatgggcg  16320
gccgtgtccg gaaccccgcc cagaccctca cgcggcgtcc acgaggcacg gatctcgatc  16380
tgggaggcgg cgggccgcgc ggacagcccg ccgaagtagt gcgaactcgc ccgcgtcacc  16440
gtgccgctcg gctcgccgta cgacaggccg cgcgccgcca gcgcgccggt cagccaggac  16500
cagcacacgt ccggcagcag cggatccgcc gccatctccg gctccagctc ggcgcgcacc  16560
agcgtcacca gacggaaggt cccccgccag gcgtcgtgtc cggccgggtc gcacagcagc  16620
accagccggc cgtcggccag atcctcctcg ccgtcgacga ccgccgcctc cagcgcgtgc  16680
gcgtacgggg cgagccgttt cggcgcgggc accgtctcca cctcgatctg cggccgcagc  16740
cgggcgctct gcagcgcctc gacagcggcc cggaagggcg gcggaggcgc acctccgtgc  16800
ccgggatccc ccccgccctc cttcggttcg tccattccgc cagcgccgtc cgacagtcgt  16860
ccctgagccg cagccatgcc gggaagatta agcggaacgg gcccccggcg cagggaggga  16920
cacccgcgcc gcccggcgct gtccggatcc tgcaccgcgg ccccgcccgc cggacgcccc  16980
tggggtccgg ggcggcggac gggtcgtgcg agactggccg gtgtgagtgc caacacgagc  17040
ccgaagggcc agacgcctac cgcgaccccc gaccccgtca agaacgacgc cgtccgggaa  17100
tcagccttcc tcaaggcgtg ccggcgcgag ccggtgccgc acacgccggt gtggttcatg  17160
cggcaggccg ggcgctcact gccggagtac cgcaaggtgc gcgagggcat cgggatgctc  17220
gactcctgca tgcggcccga gctggtcacc gagatcaccc tccagccggt gcgccgccac  17280
cacgtcgacg cggcgatcta cttcagcgac atcgtcgtcc cgctcaaggc catcggcatc  17340
gacctcgaca tcaagcccgg catcggcccg gtcgtcgagc agccggtgcg cacccgcgcc  17400
gacctcgccc ggctgcgcga cctgaccccg gaggacgtct cctacgtcac cgaggccatc  17460
ggcatgctga cccgtgagct cgggtccacc ccgctgatcg gtttcgcggg cgccccgttc  17520
acccttgcga gttacctcgt cgagggcggc ccgtcccgta cgtacgagaa cgccaaggcg  17580
atgatgtacg gcgaccccga gctctgggcc gacctgctcg accgcctcgc cgacatcacg  17640
gcggccttcc tcgacgtcca gatccgggcc ggcgcctcgg ccgtgcagct cttcgactcc  17700
tgggccggcg cgctcgcccc ctccgactac cggcgttcgg tgctgcccgc ctcggcgaag  17760
gtgttccgcg cggtggccgg ccacggcgtc ccgcgcatcc acttcggcgt cggcaccggc  17820
gagctgctgg ggctcatggg cgaggccggc gcggacatcg tcggcgtcga ctggcgcgtc  17880
ccgatggacg aggccgcccg ccgcgtcggc cccggcaagg cgctccaggg caacctggac  17940
ccgaccgtgc tgttcgccgg ccgggaggcc gtcgagacga aggcgcgcga ggtcctggac  18000
accgccgcgg gcctggaggg ccacatcttc aacctcggtc acggagtgat gccctccacc  18060
gacccggacg ccctcacccg tctcgtggag tacgtccaca cgcagacggc gcgctgaccc  18120
accgctcacg cgccggacgc gagtcggaat ccgggggcgg ggtactgggc acgggtgccc  18180
accacgttca cccccgggta cgggcaggtg gaggccccat gaggctcgag atgttcgacc  18240
ccgccccgat cggcgtcgtg ttcacccagg ggccggagca ccggctcgcg tacaccaacg  18300
ccgtctaccg ggagaccttc ggcgaccgcc cgctggggcg gacgatccgc gaggccttcc  18360
ccgacctcgc gcagtccggc tacttcgaca tcttcgaccg ggtcctcacc acgggcgcgg  18420
ccgaggtggt caccgcggtg cccctcgacc tgatctaccc cggctccacg ggcgagggca  18480
ggcgctactt cacgttcagc atctcccgcg ccacgatgag cgacggccgg ccgggagtgc  18540
tcggcgtgat cgtggaggtg accgcgcagg tgaccgccgc ggaacggatc cgtgtgctgg  18600
ccgaggagcg ccgccgcgcg ctgcagcgct accgcagcct ggtgaacgcc ggaacgcaga  18660
tggtgtgggt ggcggacgcc aagggccgga tcaccgagcc gagccccggc tgggaacgcg  18720
tgaccgggca gacctgggag gagttccgcg gcgagggctg gatgaacgcc gtccaccccg  18780
acgaccgcgc cgcctcggtc gaggcgtggc ggcgggcgac gaccgaacag gtgccgcgct  18840
ggatccacac ctaccggctg cggctggccg ccggcgggta ccggcacttc gtcgtcgacg  18900
ccgcgcccgt gcgcgacggg aacacggtga tcgaatgggt gggcacctgc acggacatcg  18960
agcgggaatg gcaggagggc cgccgtacgg aactgctggc gcgggccgcc accgccacgt  19020
ccggcatcgc gcggctggac gagatgctcg ccgccctggc cgatgtgatc gtgcccgaca  19080
tcgccgacaa ctgcaccatc cacctcctgc cgcaggccct gcaccgtctg ccgggcaccc  19140
cgctgaccac cgaacgcgtc gccgcggtca cccgcccggg gctcccggac ctgcccccgc  19200
accacgagga gcacctgcgg cccggcagcc cgctggcccg cgccgccgac cgccgcagcc  19260
cgctccactt cgtcttcccg cccggcgagc cgccggccga cctcgctccg ctcgacggcg  19320
agccctggat ggccgaggac gtcaacagcg tcgtgctgct gcccgtcgtc gtcgacggca  19380
ccaccgccgc cctggtcgcc gtctccacca gcggcgcccg cccgcccctc ggccaggcgg  19440
agatcggcct gctgcagaca ctcctggaac gcgcccacac ccccctcagc aacgccctgg  19500
agtaccagcg cacccggcag gtggccctgg ccctgcagaa cagcctgctc accgacccgc  19560
cggacgcgcc cggcctggac atcgccgtcc gctaccggcc cagcaccgcc gccgccgagg  19620
tcggcgggga ctggtacgac gcgttcgtgc tgcgcgacgg cgccaccgtc ctcaccatcg  19680
gcgacgtctc cggccacgac ctgccggccg ccgtcaccat gagccagctg cgcaacatgc  19740
tgcgcgggct cacgctggac cgccaggaac cgaccggcac catcctgcgc cggctggaca  19800
tcgccgtgca gaccctctat acggagtgca ccgccacctg cgtgctggcc cgggtggaac  19860
gcccggactc cggcggcgtc cggctgcact actccgtcgc cggtcacccg ccgccgctgc  19920
tcgtcgaggc ggacggctcc gcgcgcttcc tgaccggggc gcggtccccg atgctcgggc  19980
tcgtccccgc gccggagtac tcgagcgcca tggaaccgct gccgcccggc tccaccctgc  20040
tgctgtacac cgacgggctg gtggagcgcc gcgacgagga tctcaccgtg ggcctggagc  20100
ggctgcggca ccacgcctcg gaggcggtca gccgcccgct gcaggacttc tgcgacacac  20160
tgctcaccgg ccagctcacc gtcgacaacg acgacgacgt ggcgatgctg gtcctgcgcc  20220
ggtaggagcg tgccgaggag cgccactctg gccgatttta cccttgcttt tccatcggga  20280
ttcgttctcc ggatttcccg atccggcgcc gacggcgaga ccgttgggat caccaatacc  20340
```

-continued

```
ccggaattcc cgcctccgcc accgttgggc agcgacggat cctgtgatat ttcgactacg  20400
cgcggtgatg aattggctcg gtgccggtcg cgcccggctg tagcagttct ggagcgcgtc  20460
tggacatcgt cacgagcgct tgtgattctt ggtcctgtac acgcaagccg gcgcaacgtc  20520
cacgttgccc atcagcggtt atcggcggtc caccggcgcg acggtgaccg cgggcgggta  20580
ctcatagggg gaactgcaat gaattactca aaagcagcga gaggaatgcc gacagccgga  20640
caaggtgccg ttcgggcggc gcgcgtcgtc cgtgaaagtc cggcggaatc agaaacggtc  20700
acagttcaga tagcgtcgtt attaccgggt gagtcgctgc gctcgaaagg gatcgagcag  20760
aaccacgtcg cggcactcgc ggaggtagac gcgccgcttc cgcccatact ggtggaccgg  20820
aagacgatgc gggtcgtcga cgggatgcac cggctcctcg cggctctgct caacggacgg  20880
cagacgatcg aggccgaact gttcgacgga accgcggatg agggattcct gcgcgccgtc  20940
cgggagaacg tggtgcacgg actcccgctg tcgcaggcgg accgccgggc cgccgctgcg  21000
cgcatcatcg tgtcccaccc gcatctgtcg gacagggcga tcgcccgggc gtccgggctc  21060
ggggcgaaga ccgtcgcggc cgtgcggcgc agttcaactg ccgtcgtgcc gcagttgaac  21120
acccgggtgg gccaggacgg cagggtccgg ccgctgaacg ggggcgaggg gcggcgcagg  21180
gccatggcgg tactggccga acaccccgac gcgtccctgc gcgaggtcgc ccgtctgtcc  21240
ggggtgtcgc ccgcgacggt cagcgacgta cgcccggcgc tggccgccgg cgagtcgccc  21300
ctgccgtcga gacgggaacc ggccgaaccg cggacgggcg ccgactccca ccgcaaccag  21360
agcttcgtgg atcccgtccc ggtgctggag aagctgctgc gcgacccctc tctgcggcac  21420
aaggagggcg gccgccagct gctccagctg ctccgccaga acgcggtcgg cgtgcaggac  21480
ctgatggagc tgtccgacgc cgtgccgtcc cactgcaggt ccctggtgat ccatctcgcg  21540
cagcagtacc gggacgcctg gcagtccttc gcggagaagc tggacgagcc cgcctgcgcc  21600
tgtcccgggt gacgaacggg cggcacggac ccgttcaccg gacatgaccg gcgccgcgcc  21660
gcgttcacgg cgcgccgccg gcactcccac ggcacccgga ccaccgccgc gtatccggcg  21720
gacccgggcc cgggcgggcc ggattcagcg ggcgggggcc caggtgccac ccgattccag  21780
ccaccgggag agctccgccg ccgagtcctt gcgcacgacc agttcgacga ggccgcgggt  21840
ctggtcctga ccgtgctcga tgcggacgtc ctcgatgttg acgcccaagt cgccgatcga  21900
cgtgaacagt tcggccaggg cgccgggctt gtcggagatg gtcaccgaga cggtcgcgag  21960
ctccgtccgg cgcgtaccgg gtttgcgcac gatcctggcg cacccccggt tcccctcccg  22020
caacagctcc tcgagctcct cctgcgcgcg gcggcggacc agcgggtcgg cgtcggagac  22080
ggcgcgcagc gcgccgacgg cccggcccag gccggcggcg agggagtcga gaacgtccgc  22140
cacggccgtg gcgttggaac gcaggatgtc cccccagagc cgggcgtcac cggccgcgat  22200
ccgggtgacg tcggcgacgc cctgccccgc cagccggacg ctgtcctccg ccgcgtgctc  22260
cagccgcgcg gcgagcaggg aggagagccg atggggcgcg tgcgagacga gggccaccgc  22320
gtggtcgtgc acaccggcgt ccatgaccac cggcatgccg tcgcacaacg acaccatctc  22380
cagggcggtg ttcagcacgt cctgcccggt cagctccgac ggggtgagca cccaggggcg  22440
cccctcgaag aggtccgccc gggcggcgag cggcccggaa cgctcggtgc cggccagcgg  22500
atggcttcct atgtagctgg ccgggtcggc ccgcatcgcg cgcacgtcgt cgtgcgggac  22560
cttcttgacg ctggcgacat cgaggtaggc tcgggccagc ccgctctcct gtgcgcgcgc  22620
gagcacgcgt ccgacctgtg ccgggggcac ggccagcacc gccaggtcga cctgacggtc  22680
cggtctctcc aggatcccgc cgcccatcgc ctccgccgtc ctggcggcgt tccggtcgac  22740
gtcctccagg tgcacgccga ccccgcggcg ggtcagcgcg agagcgacgg acgtgccgat  22800
ggccccggtg ccgatgactg tggtggtcct caacgcgcgc ccccaggtgc ggtgatccga  22860
aatcggctcg gacaagtgcc gtgcccggca cgggaaaagg gaattcccat ggcgccgtgc  22920
gccgccaatt taacgcttcg gcgcgcatgt tcaactgcgg cgtcgcagcg gtcgaacaca  22980
gtagcggtac accggaccat tgaggcatcg tgctcagttg gcgacaccgg gtcggataaa  23040
cgccggaatc cgaggagttg acgttgcagt cagcgctgag acacgacgac ctgcatccga  23100
tagaagaagt ggaaataagt tcgctctcca ccgacggctc cccgcggatc gacggggaga  23160
gtcccgagca cgtggaaatg ctggccgccg ccgacaccgc gcttccaccg atcatggtgc  23220
accgccgcac cgggcgggtc atcgacggca tgcaccggct gcgcgccgcg atgctgacgg  23280
gccgtacgac gatcgcggtg aggttcttcg acggcaccga ggaggacgcc ttcgtcctcg  23340
ccgtgaagtc gaacatcgcg cacggactgc cgctgtccgc cgccgaccgc cggcgggccg  23400
ccgggcgcat catggccacc catccccggt ggtcggaccg gatgatcgcc tcggtggtcg  23460
gcacctccgc caggacggtc gccgagatcc gccgcgacgc cggcgccgcc ggggcggggg  23520
agcccacccg catcggccgg gacggcaggg tacggcccgt cgacgtgagc gagggccgca  23580
gactggccca cgacatgatc gtccgcgacc cgggcctgtc gctgcgccag gtcgcccgcg  23640
ccgccgggat ctcgccggag accgtcaggg acgtcagaca ccggatgctc cgcggtgagg  23700
acccggtgcc cgcgccgcgg ccgcggaccc tggtggagcg cggcgcggac cgccgggcgg  23760
agccggccgg gaaggccgcc gcgccgtgcg ggacggagcc gccgcccgcc gtcgtgatga  23820
agcggctgag ggccgatccg gcgctgcgtc tcaacgagaa cggacgcgac ctgctgcggc  23880
ttctggatat ccacacggtc cggctggagg actggaaccg cattatcgaa agcgtgccgc  23940
cgcaccgtct ggagacggtg gcgcagctgg cacgctcctg cgccgacaaa tggtccgaga  24000
tcgcgtcacg catcgaaagc aacgcatcac atctggccgg gtgaacgagg aaacacacga  24060
atccttcgag gagccgtcgg agaaagcggg acggcccgtc ggaacaccct tgtggagggg  24120
caatggagat acggtcgatc gatcacgtcg aattgttcgt cgaggacgcc caggacacgg  24180
ccggcaggct gtgcgactcc ttcggcttcg tccgcgtggg ccgcggcgcc gggaccaccg  24240
gactgcgcgg ctgcgagtcc gtcctgctgc gccagaacga catcgccctg ctgctgacca  24300
cggccaccga cgccgaccac cgtgccgccg agtacgtgaa gcagcacggg gacggggtcg  24360
cggtgatcgg catcggggtg gacgacgcgc gcgccgccta cgccgaggcc gtgcggcgcg  24420
gagccgtccc ggtcgccgcg cccgaggagt tcgggcccgc cggcgcccgt gtcgtcttcg  24480
cctcggtggc gggattcggc gacgtggagc accgcttcgt ctcccgggag gaccccggag  24540
cgccgttcgc gcccttcatc gaggagaccg gcgcccacgg ctccgggggc atgctgaagc  24600
gggtcgacca cttcgcggtc tgcgtcccgg ccggcgaact cgacgggacc gtccgccgct  24660
accaggaggt gttcggcctc agccagacct tcgaggagcg gatcgtcgtc ggctcgcagg  24720
ccatggactc caaggtcgtg cagagcgacc gcggcgcggt gacgttcacc gtcatcgagc  24780
cggacaccac ccgcgcaccc ggccagatcg acgcgttcgt ggcctcccac ggcggggccg  24840
gtgtgcagca cgtcgcgttc ctcactgagg acatcaccac cgcggtgcgc acctgcaccg  24900
ggcgcggggt ccgcttcctc accacgccgc cgagctacta cgagatgctg ccggggcggc  24960
tgggcccggt cggcgtaccc gtggaggagc tcagcgcgct caacatcctg gccgaccgcg  25020
acccgtccgg gatcatgctg cagatcttca ccgagtcgac gcacccgagg cggaccctgt  25080
```

-continued

```
tctgggaact gatcgaccgc cgcggcgcgc agaccttcgg cagcaacaac atccaggccc  25140
tgtacgaggc cgtggagcgc cagcaggcgg cggaggcggc cgaccaggaa tgaggaagct  25200
ccccgcagac gcgtgtggac ccggaggaca cgccctccgg gtccacacgc gtctgcgggg  25260
ccagcgtcgg ctacgccccg aggagccggc cgccgtgcag cgtctccccg tacgcgaaca  25320
catggccggc ccccacctcc acgggcgcga gcagtgccag atccgtgccc ggacggcgg   25380
agagggcgag ccggccggga ccgctccaga ccggtgagaa ctcgacgccg ctcacctccg  25440
aggcgaccag gcggggccgt ggcggggcgt cggacggcac ccaccgcgga aggacgagac  25500
tgtgcgccag cgggacgtcg tgcagcgcgg gcggccgctc ggagcggcgc tcgaccgtga  25560
ccgacgcctc ggcggtgagc cggccgtgga cggagagcgc gccgtcgaag cggcccccgg  25620
gagcgagccg tgagcccgcc cggccgacgg tcaccggcct ggtctggtgg atggcgccga  25680
actgcttggg catgccctgg acccagccgc gcaccatcgg cacgggctgg tcgacccagg  25740
cgaacgggca gcgcgccatc ggccggccct cgaacgcgca cccgaggagg atcaggaact  25800
ccgagaaccg gcagacggcc gggtcggcca gctccgcgcc gtcctcggag caccactgcc  25860
aggtggcgaa cacggcggcc gccgcacccg gatccgctcc cgcgtccagg cccggcggca  25920
ggaaacgccg tgcggcgtcg gggtcgacac ggtagtcgac catgaggatc tcgccggaga  25980
agtgccacgg cggaggcgtg agcatcgacg cctgccccga aggggacagg ggaaggctgt  26040
agccgatggg cccggcggcc ccggccgcgt ccggatccgt cggatgtgtg tgcccggtgg  26100
tggccgtcat gggttccctc cgatctgccg gtccggcggg ccgccggacc atgcctgggt  26160
cagccgtcga gcggcgcgtt cgagcagcgg gggcggattg aagctgtagg ccaggcgcac  26220
gctcggctcc cgtgtgccgc cgaagcgcga acccgcggtg acgcgcacac ccgcccgctc  26280
cgcacgggcg agcagttcgt cctcgccgag cccggtgccg caccggagcc agaggaagaa  26340
cccgccctcc ggacggctga tccgcaccgg gaggtccgcc gcctcccgca gcgcgtcgag  26400
gagggcgtcg cgccgcgccc tcagacccgc ccgcaacatt tccagatgcc ggtcgtagcc  26460
gccgtcggac agcagccctg cgacggcgag cgaggtgatg tggttgagcg acccgccgct  26520
gcggaacagc ccgtgcgacg cgatccgttc ggccagtgcc ggctccgtca ccagccagcc  26580
cagccggagc cccggcccca gggtcttgga gaagctgccc agccgcacca cgccccggtg  26640
tccggcgagg gccgccagtg gcggcggggc cgggggaccg tccgtcaggc ccagttcgcc  26700
gtaggcgtcg tcctcgacga ccaggacgcc gtgctccgcc gccgcctcca gcagccgcag  26760
ccggcgctcc agcggcatgg tggcgcccgt cggattgtgg tgggtcgggg tgaggtacac  26820
gaacgcggtg cggccggtgc cgccttcgcc gccccgcgcg gtcccggcga gggcgcgccg  26880
gagcgcctcc ggcaccatgc ccgacgcgtc gagggcgacc cgcctcaggc gcagcgcgca  26940
gtccccgagg atgcgctgcc cgaggtcgta gccgaggccc tccacgagca ccgtgtcgcc  27000
gggcctcgcg agggtggtcg ccagcaggtg gagcgcctgg gacgtgcccg ccgtgacgac  27060
cacgtgctcc ggcccgcacg gggaccgccc ccgcacggtg gcccgggcgg ccagctcggc  27120
gcgcaggggc agggcgcccg gatcgtgtcc gtagcccagt gccgccgctc cgtactcctc  27180
cagcgcgcgt gcgtaggcgt cccgcaccag ccccaccggc agcagcgccg gttcgaggta  27240
gccgggcccc aggtcgagga cgcccgcggg ggcgacctcc tgcaccacac cgcgacgcca  27300
ccgccgcgtg tgcgacaacg ggcgggccgt gccgtacggc aggtcccct cgccggcagc   27360
ggtcatcagc ggggtgtcag cacatggcgc aacgcccgta cgcactgggc cagcggggcg  27420
gacgcccggg cgagcgccag gcgcagcgtg cggtcgccgc gggcggggtc agcccagtag  27480
aaggcacggc agggcagggc gtacacatgg tgctcgcgca gcgcctccca gacctcggtc  27540
ccggtcagat gcctgatcag cacccgctcc acactggccc ggctgtccgg gtcgggcacc  27600
ccggtggtcg acaggtccgc cagcccggcg cgcaccaccg accgctgggc ggcgatgaac  27660
tcgtgcagct ccgtcagccc gccggcggcg gcgtcctcgg agaagcggcg gaccatcccg  27720
aggatcagcg gggagacgcc cagcaggatg tcggagtaga tcttctccac cggcaggccc  27780
aggttctcgg agtggaccag catgccgacc ttgaggtcga gggtcggcca gagcttgccc  27840
gtgtcctcga tgacgaccca gcgcacatcg ctggcgtcga ggatctcgta gtggtcgtac  27900
tgggcgcggg tgtcgaagcc gcggaaggac gtgtcgaggg cgaggatcac gccgtgccgt  27960
gcgcactgcc cggccagccg gcgcagccgc tccgccgaca cgacccggcc cgtcgggttg  28020
ttcggcgtgg tgacgaagac acagcccacg gactcgagca gctccgcggg caggtcgtcg  28080
gcgtgcagcg gatcctcctc caggggcacc agacccaggc ggttgccgcg caacaggtcg  28140
gcgatgttgt cgaaggtggg gtggaccagc gccacggagt ccgtgaccga cgccagggcg  28200
cgggagagga tctccatggc caccgacgag gagtagcagc tcagcacacg gccgggtgcg  28260
gacgggtagc ggtgctggcc gagggccttg aagaaggccg cgtgggcctc gcgttcgagc  28320
tgctcgacgg ggcgcttctc gccgtcctcg aaaagcagcg ggagatcatt gacgatcttg  28380
ctctggccgg gagtgagcgg ctgccgggca tgcccgtcgg cgatgttgaa ctcgctgttg  28440
agtgcgagga attccagttg ggtgaggttc tccgcgcctg atccggcgtg cgcagcgtgg  28500
gccttgcttt gcagtgttcc ggacacaggt atgcctctct gggatgtgag ggtttccaga  28560
agcggagcgg acgtaaatga gcggcccact ctacggcctt cgccctccgg ctgaaatgcc  28620
tcttcttttc ggcaccgtgt tcaactgcgg tggtgcggca gtcgaacgag ccgtctcgcc  28680
cgccgtatcg gccggacatc gcgttccgac ggtgacgcgc gtgcggttcc cgtgtccaac  28740
tgacctgagg gcgcagttgg acgggccacc ggcacacggc cgcccgatcc ttgtcggacg  28800
ggcccgggca cgcgaaagtg gacgtgcggg atctgtgttc cgccgccggt gtctcttcgt  28860
aagccgtgaa gtggggcctt gatggaattg tcgctcgatg aattcgcgtc gctcgcccgg  28920
gaacggctgg acccggccgt ctgggatttc atcgaaggcg gcgccggaga ggaacgcacg  28980
ctcgccgcga acaccgcggc attcgaccgc gtcccgctgc ggccgtcggt gctgcgcggc  29040
gcgggcagcc cgcacaccgg caccacgatc ctcgggcgga cgtgggacgc gcccctcgcg  29100
gtcgccccgg tggcctacca cacgctcgcg gacccggccg gtgaggtcgc caccgtccgg  29160
ggaacggcgg ccgccgccgg actcccggtc gtcgtcagca ccttcgcggg ccgcacgttc  29220
gaggacatcg ccgccgaggc caccgtcccg ctctggctcc aggtgtactg cctgcgggac  29280
cgctccctca cccgaggcct catcgaacgc gccgagaacg cgggcttcga ggccctggtc  29340
ctcacggtcg acgcgccgca cctcggccgc cggctgcggg acctgcgcaa cggcttccgg  29400
ctgcccgccg gcacggtccc cgccaacctc ccggtggacg gattcgcgga ccccgcggcg  29460
cactcccgcg ccgacttcga ccccggcctg gactggtcgg tggtggagtg gctgcgctcg  29520
gtctccgaac tgccgttgct cgtcaagggg atcctcaccg gcgccgacgc ggtgcgcgcg  29580
gccgaggccg gggtggacgg cgtcatggtc tccaaccacg gggccgccca gctcgacgga  29640
gtgccggcca ccctcgacgt cctgcccgag gtcgccgagg cggtcggcgg acgcctcccc  29700
gtcctcctcg acggcggggt ccgccggggg cgggacatcc tggcggcgct cgcgctcggc  29760
gccgacgcgg ccctcgtcgg ccgcccggtg ctgcacggcc tcgcggccgg cggggccggc  29820
```

-continued

```
ggggtgaccg gcgtcctctc cgtcctcctg gaggagctga cggacgcgat gtcccttgcg  29880
ggcctgagga ccctcgccga catcggcccc tcactcgtcg gccgggctcc tgaccacccc  29940
cgcccgaagca ccgtggacgc cgggaagggc gcggggagcg accggcgcac cgccgccggg  30000
ggaggggccg ggctgcgcct cgcggacctg cacccgagtg tcgccgaccc ggtcatggac  30060
accatgaact tcctcaacga ggtgacactg cgctaccccg aggcggtgtc cttcgccccc  30120
ggacggccct acgcggagtt cttcgagacc gagcaggtct tccgccatct gcgccgctac  30180
ctcgaccacc tggccgagca gggccgttcg cccgcgcagg tgcgcgacgc gctgttccag  30240
tacggtccgt ccgccggtgt gatccgcgag ctgatcgccc actcgctgcg ggtggacgag  30300
ggcatcgacg tgtcgcccga gtcgatcgtg gtgacggtcg gctgccagga ggcgatgttc  30360
ctgacgctgc gcgcgctcat gtccggcccg gacgacgtgc tgctcgtctc cagcccctgc  30420
tacgtgggga tcaccggggc cgcccggctg ctggacgtcg cggtgaccgc cgtcgaggag  30480
ggcgaggacg gcctgtcgtg cgacgccctc gaggccgccg tctcggcgga gcgggcgcgc  30540
ggcaggcggc cgcgggccgt ctacgtggtc ccggaccact cgaacccgtc cggcgcgacc  30600
atgccgctcg aggcccggaa gtccctcctg gagctggcgc agcggctcga cgtcctcgtc  30660
ctggaggaca gcccgtaccg gcacgtcagc ccgggcacgc aggtggcgtc cctgaaggcc  30720
ctcgaccgga cacggcgagt gatccacctc ggttcctacg ccaagaccgt cttccccggg  30780
gcacgcctcg ggttcgcggt cgccgaccag ccggtgctgg cgccggacgg cggcacgagt  30840
ctgctggcgg acgaactcgc caagatcaag agcatggtca cggtcaacac ctcgccgctc  30900
agccaggccg cggtggcggg cgcgctgctg gagtcgggcg gccgtgtctc ggagctcaac  30960
gcccgcaacg ccgcccacta cggggaggcc atgcgcttca ccctgcagtg cctggagcgg  31020
gagttcccgg ccgcgcggcg gacccggctc ggcgtccgct ggaacgcgcc cagcggcggg  31080
ttcttcctca ccctccaggt gccgttccgc gcggacaact ccgcgctggc ccggtccgcg  31140
caggacttcg gggtcatctg gacgccgatg tcgtacttct atccgcaggg cggcggcctg  31200
cacaccctca ggctctccac cagctacctg acccacgccg acatcgagaa gggcatctcc  31260
cggctggccg ggttcatcga gttcgagtgc ggggacccgg tggcctgaac cgccgcgacg  31320
acgaagggcc ccggccgcgc cggcggggcc cttcgtcggt cgcgacgctc aggacggatg  31380
cggctcctcc cagaacatgc tgtcggacga ggcgacgaga ccgccgtcga agagcgggac  31440
gtcctcgccg gcgtactctc ccagctgcgc ccgggtctgc acctgcgagc cctcctgcat  31500
cgcccggctc accgccgacg accggaacag cggggccatg ttctcctcct gccgcccggc  31560
catgtcgtcg acggcgtcgg cgaactccgc cgactgctgc ttgagccgca ggacgctcga  31620
ctcggcgtcg gagaggtcga agtccgtgct ggacatgccc gccaccagct ccacgaacga  31680
ctccagctcg gcgtggctgc tccgggtgac cttcttcgcc gtccagaagt aggagtcctc  31740
gtcgacgtgc atgtcgtaga acgaggtcag gaactcgtag aagacgccgt actcccgccg  31800
gtaccgggcc tcgaactcgt cgaaggcccg ccgctcgtcg atccgccccg ccagcacgct  31860
gttgagggag cgggcggcca gcagcgcgct gtaggtggcc agatggaccc cggaggagaa  31920
gacggggtcg acgaagcacg ccgcgtcacc gacgagcacc atccccggcc gccagaaggt  31980
cgtgtggtgg tacgagtagt ccttgcgcac ccgcagctgc ccgtactgac cggtcgtgac  32040
ccgggtggcg tccgccaggt actccttgat catcgggcat tcgtcgatga ggccgcgcag  32100
cgcgctctcc gggtcgccct gcaccttggc cgcgtcctcc cggcggacga ccgcgccgac  32160
gctggtcagc gtggagctga gcgggatgta ccagaaccag ccgctgccga acgccacaca  32220
gaggatgttg ccggcgtagg gcgccggcat ccgcttgccg ttctcgaagt agccgaacag  32280
cgccaggctc ttgaagaagt ccgagtacgt gcgcgagccg ccgacccgct tgtggatgcg  32340
gctggtgttg cccgaggcgt ccaccacgta ccgggccgac acctcgtgct ccgtgccgtc  32400
cgggtcggtg taccgcagcc cgcgggcccg cccgtcggcg tcgtccacga catcggtgac  32460
cgtgcggtcc tggcggacca cgacaccctt gcgggccgcg ttgtccagca ggatcttgtc  32520
gaatttgctc cgctccacct gataggcgaa cgaggtcggt ccggagacct tggacgagac  32580
ggagaaggag aaattccacg gcttggggct cgcaccccac cggaacgtcc caccgcgctt  32640
gtgcggaaaa ccggcggcgg cgagttcgtc ggtgacaccg agcagatggc agatgccgtg  32700
aatggtcgac ggcagaagcg actcgcctat ctggtacctg gggaaggtct ccttttcgag  32760
cagcagcaca ctgtgcccct gcatggccac cagggtcgag agcgtcgacc ccgaagggcc  32820
gccgcccacg accacgacgt cgaattcctc gtgctgtcct gtactcattc ggcctcccgg  32880
cacgcactga tgcggtcatc gcgctggtga ctcttttgtc agggttccac aggactcaaa  32940
ggggccaaag ggtggacgac attccgtgaa tggacagccg ggcccgggcg cgcgcacgca  33000
aaggcgccgc cggggaattc ccggcggcgc ccggaccggc gtcgggtgag acgggggtca  33060
actcacccgg cgccggatcc gccacacccc gaacaccgtg aggattccgc tgagtgccac  33120
atagatcgcg gtctccagcc actggaacgc ccagtagcgg ctgctggggt ggtacaggac  33180
gtcgacgtgc aggtcgtgtt cggcgaggca caccgcggtg tcgccgaacg tgccccccgc  33240
gccggtcttg ggcgggtcgt cgaggcagcc gttgaactcg ctggaggcga gggtcctgcc  33300
gtccgcggtg cgcagcggac tggtctcggc gatccacgcg tccggcgcgt ccgggatccg  33360
caccccgccg atgacggatc cgccgccgat actgcccagg ttctgcgccg agttgatcgc  33420
ctcggccgtc atcgccagcg tcgtcctgtc cggcggcatc aggctgggcc gcaccacgtt  33480
cgggaagaag aactggaagg cgatgaagac caccagcgtc accgccatcg cgggcagggt  33540
ccgccgcagc aggagcccga cgacggtgcc gaacgtgaag gccagcgcgg cgtagccgat  33600
cggggcgatg ttgcgcgcac cgaacacgaa ggtgtcgaac tgctccttga cgacgtcgtc  33660
gaagggccgg gccgcccagg tgagcagggc cgcggccgca ccggtcacga tcaccgaggc  33720
cgcgccgatg agcaggatct tgctgagcag ccagcgcggc cgggtgacgc tctggttcca  33780
caccagccga tgggtgccgt tctcgagttc cctggcgatc aggggagcgc cccagaaggt  33840
gccgatgagc gcggggatca gggccaggcc ggtcgccagg aacagcaggg tgttctggaa  33900
ggtgctgcgg aactggctcc tggcctgggc gcagttggcc gagttgtcgc agttggcctg  33960
gtagacgtca tgggcgtcac ggatgtcccc gcccaggtag agcaggtaga cggcgatcac  34020
ggccagcgcg ccggcgccga acagggcctg gacgcggaac tgccgccagc tgagccacat  34080
catcgggtgg ccccccaggc tgcggcctcg gtgcgggcgg cgggaacggc ggccgcccgg  34140
gtcatgtagg cgagcacgag ttcctcgagg gtgaccggct cggaccggta gggcagtgcc  34200
tcggtcgcgg cgccggtgcg gacgaccgcg ctgctgtgct tgccgctgtg ctcgaccgag  34260
atcacctcga tcccggcggg cggctggtcg aactcgccgc gggccgcgac cagccgggcg  34320
tgcccggcca gcagctcccg ggtgtcgccg gcgacctgca cccgggcgtc gcacagcacg  34380
atgagatagt cgcagacctg ctccacgtca ccgaggaggt gcgaggagag gacggcgctg  34440
gcgccgagct ccagcacgaa ctccatcagg ttctgcagga acccccggcg cgccaggggg  34500
tccagggccg ccgccggctc gtcgaagatc agcagctccg gccgcttggc cgccgcgatg  34560
```

```
gtcagcgcaa gctgcgcgcg ctggccaccc gagagctgcc cggccttctg cccggcgctg  34620
agccccacct ggctgatgcg ccgctctgcc aggaccgggt cccagcccgg gttcatcttc  34680
gcgccgaact tcaggtgctc cgccacggtg aacgcgccgt acaccggcgt gttctgcgcg  34740
acgaacccca cccgggccag gtgcgacgcg ttggccgccg gacgcgagcc gaggacgctc  34800
agtgagccgg acgtcggttc ggtcagcccg caggccaggt gcaggagggt cgatttgccg  34860
gccccgttcg ggccgaccag tccgatgaca cggccggcgg ggacgctgag gtgcacgtcg  34920
ctcagggcga gcttgccgcg gcggccgtac ttcttcgtca agccctccgc gtgaagcacg  34980
ggaggggagt ctgcgtgtgg catgactcca tcctcgaatt ccgcccccgtt cacggcatca  35040
gtccaaagca cggttcccgt tgccggcggc cgtactttcg gccggtcggc cacggccctg  35100
ctggtgggcg aactgggtgc ggtacagctc ggagtagaga ccgccgccgg ccagcagctg  35160
gtcgtgggtg ccccgctcct ggatccgccc gtcgtcgatg acgaggatct ggtcggcgtc  35220
ctggatggtg gacagccggt gcgcgatgac gagcgaggtg cgcccggtca gggcggtctt  35280
gagggcccgc tggatggcca gctcggactc ggagtccagg tgcgccgtcg cctcgtccag  35340
gacgacgatc ggaggcgact tgagcaggag ccgggcgatg gccagccgct gcttctcacc  35400
gccggacagc cggtagccgc ggtcgccgac gaccgtgtcg agaccgtccg ggagctggga  35460
gatcgtcggc cagatccgcg ccgcctcgca cgcctggacg atctcgggct cggaggcgtc  35520
cgggcgggcg tacagcaggt tggcccggat ggtgtcgtgg aacaggtgcg cgtcctgggt  35580
gaccacgccg accgtgttct gcagcgagcc gagggtcagg tcgcggacgt cgtggccgcc  35640
gatccgcacc gttcccgagg tggcgtcgta gagccgtggc accaggtggg tgatcgtggt  35700
cttgccccgcg ccggacgggc cgaccagcgc cgtgagccgg ccggccgggg cgtggaagct  35760
cacgtcgttg aggaccagcg cgccggggcc ctgctcgctc ttgcgctgcg gcatcaactc  35820
cagtgagggc agggacactt cctcggcgct ggggtagcgg aaggcgacct ggtcgaactc  35880
gacgggggga gcggtgccgt cgccgttcgc cgaggcgcgg gccggcaggg ggcgggcgcc  35940
gggacgctcg gtgatcagcg gcttcaggtc cagcacctcg aagacgcggt cgaagctgac  36000
cagcgcggtc atgacgtcgc tctggatgtt cgtcagctgg ttgacggggc cgtacagcat  36060
cagcagcagg gcgaccatgg ccaccagcgt gccgatctgc agcgagccgt cgatgacgaa  36120
ccagccgccg aagccgtaca ccatcgccgt ggtgacggtg gtgagcaggg tgacgaggat  36180
gaacagcagc cgtgcgtgca cgtccatcga gatcgcgatg tcccggacga ggcccgcctt  36240
cttggagaac tcggcggact cgtcctccgg acggccgtag agcttgacga gcatcgcgcc  36300
ggagatgttg aaccgctcgg tcatcatcga gcccagcttg gcgtcgttct gcatgccggc  36360
gcgggccagc ttctccagcc gctgggcgat gatcttcccg gggatgaaga acagcgggat  36420
catgatcagc gccgccacgg tgatcggcca cgagaggtag agcatcgccg cgagcaccag  36480
gaccagcgtc agcagcgtcg acagcgactg cgacagcagc gaggtgaggg cctgttgggc  36540
gcccacgatg tcggtgttga tccggctgac cagcgacccg gtctgggtgc gggtgaagaa  36600
cgccaccggc tgccgctgga tgtgggagaa caccgcggtc cgcaggtcga agatgaggcc  36660
ctggccgacc cttccggaga accacgtctg cgtgtagacc gccacgacgt tcagcagggc  36720
cagtccggcg acgagcccgg cgaggccgaa cacgacggac gtcttcccgg ggatgatgcc  36780
gtcatcgatg atcattttga gggtcagcgg gatcgacacc gtgatcaggg agtcgacgat  36840
cgtcgccacc atgaccatcg ccatggcccg gcggtagcgc atggcgtagg gaatgatccg  36900
cttgaacgtg ccggacctga ccggctgcgg gtccaccagt ccttcgaccc gcagtccgat  36960
cgtgcccatc gtcgggtcgt gtcccacggt cacggagact ctcctcagtg tgtgtcgcgt  37020
cgctatgtgt cgcgtcgctg tgtggcgcgt cgctgtgtgt cgtcggggcg tcgcgtcagt  37080
gcttgtcgag gaactcgacg atcgccgcgt tgaccgcgtc gggccgctcg aagtacccga  37140
ggtgcccgca gtccgggatc tccacgagat cgcagtcggg aacggcctcg gcgacctcca  37200
cgcccaggtg cggcggggtg atgaggtcgt cggcgaaggt cacgacgcga cagggggcgg  37260
ccacccggcg cagcgccggg cggcggtcgt ccatgatgtc ggcccaggcg tgccgggcct  37320
gcgcctcccc gcccccggac agctcgaaga cgtccagcca ggcggtcacc gcctggtcgt  37380
cgttgagcgt cgcgggcgag aacatccgga acaccgtcga cgcggcgtcg tacgcggccg  37440
gcagccgcac cccgctctcc accagtgccg tctccgcccg cgtctgggcc cgccgcgcgg  37500
cgtccgcacg ggcccgggtg gcgatgagca ccgcgcaccg cacgagttcg ggatgcccga  37560
tcgccagctc ctgcgcgatc atcgcccccca gggaggtgcc cacgatccgg cacggcgcca  37620
gatccagggc ctcgatcagg cccttggcgt cggcggtcat gtccagcagc gagtacctgc  37680
ccggcggcgc gtcggacggc gggacacccc ggtggtcgaa gacgaccgtg gagtagcccg  37740
ccgtgtgcag cgccggcgtc tggtgcaggg tccaggcatg gccggccgag cccgagccca  37800
tgatcatgag caccggttcg ccccggcccg cacgctggta ggcgatgcgg acgcccccca  37860
cggtgacgaa gtgcggggcg cgccggcccg cggtgtggtc catgccgcct ctccctcctc  37920
gtcgtcgcgg gggccgcccg gtggtaccgg ccggccccgg gggcggctca ctatcgcacg  37980
cggccacggg gcggggcagt gtgcgcgggg cacgtccatg gacacccccc ggcccgcgtc  38040
caactgcggt gatgccctca gttggacacc ggccggccgc gtccaagcag gcccggccga  38100
cggttgatcc gctgtgtgga gctgagccat attgggccgc cgtgagccac tgacgcccac  38160
caagtccccg cgcttcttcc gcaccggccg cctggcgcgc ccgtcgcgcc gagggaggga  38220
ccaccttgtc agcttccgac cttccagcca cccggctgac acccgagaag atccggtcct  38280
ggctcgtcga ccgggtcgcc tactacgcca ggctgcccgc cgaggagatc ggcgccgacg  38340
tcccgctcgc gcactacgga ctggactcgg tgtacgcctt cgccctgtgc ggagacatcg  38400
aggacggcct cggcctcgtc gtcgagcccg tcctgctctg ggacgtcgac accatcaccg  38460
agctcaccga ccatctcgcc gaactgacag ccgactgagg gccttcgagg gggaggacga  38520
tgcgtcgaaa ggacctggag aggctgacgt ccggtcagct cggcgtctgg tacgcgcagc  38580
agctcgaacc cctgagcccc gtgtacaaca tcgccgagta cgtggagatc cgcggcgacg  38640
tggacgtcgg gcttctggtg tcggcgctgc ggtctgccct cgacgaggcc cagacctacc  38700
ggctccgctt ccggcaggag gacgccggcc ccggacagta cgtcgacgac tcgctggagc  38760
ttcccgtcca cgtcgccgac ctcggctccg caggggaccc gcgcgccgcg gccgtggagt  38820
ggatgaccgc cgacctggac cgccccgcgg acccccctcac cggcccgctg gccgcccacg  38880
ccgtgttccg gctgggaccc ggccatgtcc tctggtacca gcgtgcccac cacctcgtcc  38940
tcgacgggac cagcctctcc gtgttcgccg gtgggatccc cgggtaccga gctcgaattc  39000
gccctatagt gagtcgtatt acaattcact ggccgtcgtt ttacaacgtc gtgactggga  39060
aaaccctggc gttacccaac ttaatcgcct tgcagcacat cccccctttcg ccagctggcg  39120
taatagcgaa gaggcccgca ccgatcgccc ttcccaacag ttgcgcagct gaatggcgaa  39180
tggcgcctga tgcggtattt tctccttacg catctgtgcg gtatttcaca ccgcatatgg  39240
tgcactctca gtacaatctg ctctgatgcc gcatagttaa gccagccccg acacccgcca  39300
```

```
acacccgctg acgcgaaccc cttgcggccg c                             39331

SEQ ID NO: 40          moltype = DNA  length = 40551
FEATURE                Location/Qualifiers
misc_feature           1..40551
                       note = Synthetic fosmid pXYF24
source                 1..40551
                       mol_type = other DNA
                       organism = synthetic construct
SEQUENCE: 40
atcgaatata acttcgtata atgtatgcta tacgaagtta ttagcgatga gctcggactt  60
ccattgttca ttccacggac aaaaacagag aaaggaaacg acagaggcca aaaagctcgc  120
tttcagcacc tgtcgtttcc tttcttttca gagggtattt taaataaaaa cattaagtta  180
tgacgaagaa gaacggaaac gccttaaacc ggaaaatttt cataaatagc gaaaacccgc  240
gaggtcgccg ccccgtaacc tgtcggatca ccggaaagga cccgtaaagt gataatgatt  300
atcatctaca tatcacaacg tgcgtggagg ccatcaaacc acgtcaaata atcaattatg  360
acgcaggtat cgtattaatt gatctgcatc aacttaacgt aaaaacaact tcagacaata  420
caaatcagcg acactgaata cggggcaacc tcatgtccga gctcgcgagc tcgtcgacag  480
cgacacactt gcatcggatg cagcccggtt aacgtgccgg cacggcctgg gtaaccaggt  540
attttgtcca cataaccgtg cgcaaaatgt tgtggataag caggacacag cagcaatcca  600
cagcaggcat acaaccgcac accgaggtta ctccgttcta caggttacga cgacatgtca  660
atacttgccc ttgacaggca ttgatggaat cgtagtctca cgctgatagt ctgatcgaca  720
atacaagtgg gaccgtggtc ccagaccgat aatcagaccg acaacacgag tgggatcgtg  780
gtcccagact aataatcaga ccgacgatac gagtgggacc gtggtcccag actaataatc  840
agaccgacga tacgagtggg accgtggttc cagactaata atcagaccga cgatacgagt  900
gggaccgtgg tcccagacta ataatcagac cgacgatacg agtgggacca tggtcccaga  960
ctaataatca gaccgacgat acgagtggga ccgtggtccc agtctgatta tcagaccgac  1020
gatacgagtg ggaccgtggt cccagactaa taatcagacc gacgatacga gtgggaccgt  1080
ggtcccagac taataatcag accgacgata cgagtgggac cgtggtccca gtctgattat  1140
cagaccgacg atacaagtgg aacagtgggc ccagagagaa tattcaggcc agttatgctt  1200
tctggcctgt aacaaaggac attaagtaaa gacagataaa cgtagactaa aacgtggtcg  1260
catcagggtg ctggcttttc aagttcctta agaatggcct caattttctc tatacactca  1320
gttggaacac gagacctgtc caggttaagc accattttat cgcccttata caatactgtc  1380
gctccaggag caaactgatg tcgtgagctt aaactagttc ttgatgcaga tgacgtttta  1440
agcacagaag ttaaaagagt gataacttct tcagcttcaa atatcacccc agcttttttc  1500
tgctcatgaa ggttagatgc ctgctgctta agtaattcct ctttatctgt aaaggctttt  1560
tgaagtgcat cacctgaccg ggcagatagt tcaccggggt gagaaaaaag agcaacaact  1620
gatttaggca atttggcggt gttgatacag cgggtaataa tcttacgtga aatattttcc  1680
gcatcagcca gcgcagaaat atttccagca aattcattct gcaatcggct tgcataacgc  1740
tgaccacgtt cataagcact tgttgggcga taatcgttac ccaatctgga taatgcagcc  1800
atctgctcat catccagctc gccaaccaga acacgataat cactttcggt aagtgcagca  1860
gctttacgac ggcgactccc atcggcaatt tctatgacac cagatactct tcgaccgaac  1920
gccggtgtct gttgaccagt cagtagaaaa gaagggatga gatcatccag tgcgtcctca  1980
gtaagcagct cctggtcacg ttcattacct gaccataccc gagaggtctt ctcaacacta  2040
tcaccccgga gcacttcaag agtaaacttc acatcccgac cacatacagg caaagtaatg  2100
gcattaccgc gagccattac tcctacgcgc gcaattaacg aatccaccat cggggcagct  2160
ggtgtcgata acgaagtatc ttcaaccggt tgagtattga gcgtatgttt tggaataaca  2220
ggcgcacgct tcattatcta atctcccagc gtggtttaat cagacgatcg aaaatttcat  2280
tgcagacagg ttcccaaata gaaagagcat ttctccaggc accagttgaa gagcgttgat  2340
caatggcctg ttcaaaaaca gttctcatcc ggatctgacc tttaccaact tcatccgttt  2400
cacgtacaac atttttttaga accatgcttc cccaggcatc ccgaatttgc tcctccatcc  2460
acggggactg agagccatta ctattgctgt atttggtaag caaaatacgt acatcaggct  2520
cgaacccttt aagatcaacg ttcttgagca gatcacgaag catatcgaaa aactgcagtg  2580
cggaggtgta gtcaaacaac tcagcaggcg tgggaacaat cagcacatca gcagcacata  2640
cgacattaat cgtgccgata cccaggttag gcgcgctgtc aataactatg acatcatagt  2700
catgagcaac agtttcaatg gccagtcgga gcatcaggtg tggatcggtg ggcagtttac  2760
cttcatcaaa tttgcccatt aactcagttt caatacggtg cagagccaga caggaaggaa  2820
taatgtcaag ccccggccag caagtgggct ttattgcata agtgacatcg tccttttccc  2880
caagatagaa aggcaggaga gtgtcttctg catgaatatg aagatctggt acccatccgt  2940
gatacattga ggctgttccc tgggggtcgt taccttccac gagcaaaaca cgtagcccct  3000
tcagagccag atcctgagca agatgaacag aaactgaggt tttgtaaacg ccacctttat  3060
gggcagcaac cccgatcacc ggtggaaata cgtcttcagc acgtcgcaat cgcgtaccaa  3120
acacatcacg catatgatta atttgttcaa ttgtataacc aacacgttgc tcaacccgtc  3180
ctcgaatttc catatccggg tgcggtagtc gccctgcttt ctcggcatct ctgatagcct  3240
gagaagaaac cccaactaaa tccgctgctt cacctattct ccagcgccgg gttattttcc  3300
tcgcttccgg gctgtcatca ttaaactgtg caatggcgat agccttcgtc atttcatgac  3360
cagcgtttat gcactggtta agtgtttcca tgagtttcat tctgaacatc ctttaatcat  3420
tgctttgcgt ttttttatta aatcttgcaa tttactgcaa agcaacaaca aaatcgcaaa  3480
gtcatcaaaa aaccgcaaag ttgtttaaaa taagagcaac actacaaaag gagataagaa  3540
gagcacatac ctcagtcact tattatcact agcgctcgcc gcagccgtgt aaccgagcat  3600
agcgagcgaa ctggcgagga agcaaagaag aactgttctg tcagatagct cttacgctca  3660
gcgcaagaag aaatatccac cgtgggaaaa actccaggta gaggtacaca cgcggatagc  3720
caattcagag taataaactg tgataatcaa ccctcatcaa tgatgacgaa ctaacccccg  3780
atatcaggtc acatgacgaa gggaaagaga aggaaatcaa ctgtgacaaa ctgccctcaa  3840
atttggcttc cttaaaaatt acagttcaaa aagtatgaga aaatccatgc aggctgaagg  3900
aaacagcaaa actgtgacaa attaccctca gtaggtcaga acaaatgtga cgaaccaccc  3960
tcaaatctgt gacagataac cctcagacta tcctgtcgtc atggaagtga tatcgcggaa  4020
ggaaaatacg atatgagtcg tctggcggcc tttctttttc tcaatgtatg agaggcgcat  4080
tggagttctg ctgttgatct cattaacaca gacctgcagg aagcggcggc ggaagtcagg  4140
```

```
catacgctgg taactttgag gcagctggta acgctctatg atccagtcga ttttcagaga  4200
gacgatgcct gagccatccg gcttacgata ctgacacagg gattcgtata aacgcatggc  4260
atacggattg gtgatttctt ttgtttcact aagccgaaac tgcgtaaacc ggttctgtaa  4320
cccgataaag aagggaatga gatatgggtt gatatgtaca ctgtaaagcc ctctggatgg  4380
actgtgcgca cgtttgataa accaaggaaa agattcatag ccttttcat cgccggcatc  4440
ctcttcaggg cgataaaaaa ccacttcctt ccccgcgaaa ctcttcaatg cctgccgtat  4500
atccttactg gcttccgcag aggtcaatcc gaatatttca gcatatttag caacatggat  4560
ctcgcagata ccgtcatgtt cctgtagggt gccatcagat ttctgatct ggtcaacgaa  4620
cagatacagc atacgttttt gatcccggga gagactatat gccgcctcag tgaggtcgtt  4680
tgactggacg attcgcgggc tatttttacg tttcttgtga ttgataaccg ctgtttccgc  4740
catgacagat ccatgtgaag tgtgacaagt ttttagattg tcacactaaa taaaaaagag  4800
tcaataagca gggataactt tgtgaaaaaa cagcttcttc tgagggcaat ttgtcacagg  4860
gttaagggca atttgtcaca gacaggactg tcatttgagg gtgatttgtc acactgaaag  4920
ggcaatttgt cacaacacct tctctagaac cagcatggat aaaggcctac aaggcgctct  4980
aaaaaagaag atctaaaaac tataaaaaaa ataattataa aaatatcccc gtggataagt  5040
ggataacccc aagggaagtt ttttcaggca tcgtgtgtaa gcagaatata taagtgctgt  5100
tccctggtgc ttcctcgctc actcgaccgg gagggttcga gaagggggggg cacccccctt  5160
cggcgtgcgc ggtcacgcgc acagggcgca gccctggtta aaaacaaggt ttataaatat  5220
tggtttaaaa gcaggttaaa agacaggtta gcggtggccg aaaaacgggc ggaaaccctt  5280
gcaaatgctg gattttctgc ctgtggacag cccctcaaat gtcaataggt gcgcccctca  5340
tctgtcagca ctctgcccct caagtgtcaa ggatcgcgcc cctcatctgt cagtagtcgc  5400
gcccctcaag tgtcaatacc gcagggcact tatccccagg cttgtccaca tcatctgtgg  5460
gaaactcgcg taaaatcagg cgttttcgcc gatttgcgag gctggccagc tccacgtcgc  5520
cggccgaaat cgagcctgcc cctcatctgt caacgccgcg ccgggtgagt cggcccctca  5580
agtgtcaacg tccgcccctc atctgtcagt gagggccaag ttttccgcga ggtatccaca  5640
acgccggcgg ccggccgcgg tgtctcgcac acggcttcga cggcgtttct ggcgcgtttg  5700
cagggccata gacggccgcc agcccagcgg cgagggcaac cagccgaggg cttcgccctg  5760
tcgctcgact gcggcgagca ctactggctg taaaaggaca gaccacatca tggttctgtg  5820
ttcattaggt tgttctgtcc attgctgaca taatccgctc cacttcaacg taacaccgca  5880
cgaagatttc tattgttcct gaaggcatat tcaaatcgtt ttcgttaccg cttgcaggca  5940
tcatgacaga acactacttc ctataaacgc tacacaggct cctgagatta ataatgcgga  6000
tctctacgat aatgggagat ttcccgact gtttcgttcg cttctcagtg gataacagcc  6060
agcttctctg tttaacagac aaaaacagca tatccactca gttccacatt tccatataaa  6120
ggccaaggca tttattctca ggataattgt ttcagcatcg caaccgcatc agactccggc  6180
atcgcaaact gcacccggtg ccgggcagcc acatccagcg caaaaacctt cgtgtagact  6240
tccgttgaac tgatggactt atgtcccatc aggctttgca gaactttcag cggtataccg  6300
gcatacagca tgtgcatcgc ataggaatgg cggaacgtat gtggtgtgac cggaacagag  6360
aacgtcacac cgtcagcagc agcggcggca accgcctccc caatccaggt cctgaccgtt  6420
ctgtccgtca cttcccagat ccgcgctttc tctgtccttc ctgtgcgacg gttacgccgc  6480
tccatgagct tatcgcgaat aaatacctgt gacggaagat cacttcgcag aataaataaa  6540
tcctggtgtc cctgttgata ccgggaagcc ctgggccaac ttttggcgaa aatgagacgt  6600
tgatcggcac gtaagaggtt ccaactttca ccataatgaa ataagatcac taccgggcgt  6660
attttttgag ttatcgagat tttcaggagc taaggaagct aaaatggaga aaaaaatcac  6720
tggatatacc accgttgata tatcccaatg gcatcgtaaa gaacattttg aggcatttca  6780
gtcagttgct caatgtacct ataaccagac cgttcagctg gatattacgg cctttttaaa  6840
gaccgtaaag aaaaataagc acaagtttta tccggccttt attcacattc ttgcccgcct  6900
gatgaatgct catccggaat ttcgtatggc aatgaaagac ggtgagctgg tgatatggga  6960
tagtgttcac ccttgttaca ccgttttcca tgagcaaact gaaacgtttt catcgctctg  7020
gagtgaatac cacgacgatt tccggcagtt tctacacata tattcgcaag atgtggcgtg  7080
ttacggtgaa aacctggcct atttccctaa agggtttatt gagaatatgt ttttcgtctc  7140
agccaatccc tgggtgagtt tcaccagttt tgatttaaac gtggccaata tggacaactt  7200
cttcgccccc gttttcacca tgggcaaata ttatacgcaa ggcgacaagg tgctgatgcc  7260
gctggcgatt caggttcatc atgccgtttg tgatggcttc catgtcggca gaatgcttaa  7320
tgaattacaa cagtactgcg atgagtggca gggcggggcg taatttttt aaggcagtta  7380
ttggtgccct taaacgcctg gttgctacgc ctgaataagt gataataagc ggatgaatgg  7440
cagaaattcg atgataagct gtcaaacatg agaattggtc gacggcccgg gcggccgcaa  7500
ggggttcgcg ttggccgatt cattaatgca gctggcacga caggtttccc gactggaaag  7560
cgggcagtga gcgcaacgca attaatgtga gttagctcac tcattaggca ccccaggctt  7620
tacactttat gcttccggct cgtatgttgt gtggaattgt gagcggataa caatttcaca  7680
caggaaacag ctatgaccat gattacgcca agctatttag gtgagactat agaatactca  7740
agcttgcatg cctgcaggtc gactctagag gatcccacgg ttcttctccc gggtccaccc  7800
ccggttccgg acgccgtacc ggccgacgat cctgctcggc gtcgccatcg cgatcctcgc  7860
cggcttcacc ccgctgaacg agctcgcggc gctggtgaac atcggcaccc tgttcgcctt  7920
cgtgatcgtc gcgatcagcg tgatcatcct ccgcaggacc cggcccgacc tgccccgcgc  7980
cttccgcacg ccctgggtgc ccgtgctgcc gatcgtctcg gtcgccgcgt ccctgtggct  8040
gatgctgaac ctgccggccg agacctgggt ccgcttcggc atctggatgg cggtcggcgt  8100
cgtcgtctac ttcctgtaca gccgcaaaca cagccgtctg gccgaggagc gcggcgggga  8160
acggacgtcg tcctgaggcc ggcgcctccc ggcgctaccc gtcccgccgc ggcgcccagg  8220
cgccgcccgc gggccgcacc gcgcgcgggc cggtgacgtc agcgcccagg gacgtcaccc  8280
ggcggcgcag ctcgcggtcg gccgtgacca ccaggaccgg gcggtcgccc gcctccgcca  8340
ccaggtcgac catgcggtcg tcgccgctgc ccggggccgg gtccacccgg acaccgggga  8400
ccgactccac cccgcgggcc gcccccctcgg tcaccaggac gatctccacc gggcccgggt  8460
gacccggcac gccctccgcg gccagccggt cgcgcagccg ttccgcggcg ccccggcggt  8520
cccgccacca tccgtcgggc accgacccga ccacgttggc ggcgtcgacg atcacgagca  8580
ggccggtgtc atccatggcg tcagggtccc acgcggcgcc ccggccgtcc gggtcgcggg  8640
ggtgcgaccg cgcgcggggg aggacgcccg ggaacacatg aacgatcgac atatgatgtg  8700
tcgagtttca gcgttcccgc gtcggtgacg cggcgggccg caggaagggg cacctggcga  8760
tgcggagaag gtcggcgggc cccgtgggcg cctccgtcaa ggacggacgt gccgccgggg  8820
agcaccggga ggccgcgtcc ggggccgccc acggtgactg gctcacccgc ggcaaggacg  8880
```

```
gccggctgac gctgtacgtc cccaccgacg gcggtctgct gcgctggacg gagaccgccg  8940
tgggtggccc cggctggagc ggtccgcact tcgtcccggt ggccgggctg acgcacctgg  9000
cggtggctca gggagccaac ggctacgtcc acttcctcgg ccgcagggag cgcgagggcg  9060
ccgactccac gccgggcgtg gacatcgtgc acgcgatcca gtaccagacc ggactcgcct  9120
tcagcgactg gcggtccctc ggcaacccgc accgggtccc ggaggagccc ggaccgctcg  9180
ccgtgccggt cggggcggtc gcccgggacg gcaccgtgca cgtgttcgtg cggggcgcgc  9240
acggagggct gatgctgcgg cgcgaggccc cgaacggcaa gtggaaggcg tgggaggacc  9300
tgggcggcgg cggcgccggc gcccagcccg cggcgctcgc gctcaccgac gggcggatcg  9360
aggtctgcgt ggccgccgag acgggcgtgc tggcgtggag ccagtccaag cccggcggcg  9420
acttcaccgg gccccggggt ttctcgctgc gccccgtgcc gggcacggtc gcggccctgg  9480
agaccggtcc gggccgggcc acgttcttct ggacggacgc cgagagcggc ggtgcggcgg  9540
cctggcgggc gggggcgtgg cccgtcgcgc tgggcggtac cccggccgag cggccgtgcg  9600
cggtgctccg cacgtcgctg gacggctacg actgtgtcgt cctcgcctac cgtgaccagg  9660
acggcacggc cgtgctcggc atgggcggca cggagaacga ggccgccggc ttctggtggt  9720
acgcgctgac cgagtcctgc cagggcgctc cggccctggc cctggacggg cggggccgcg  9780
tggtgatggc gctgatcggc gccgacggca ggcccagggt cgcccgccag gaggacggcg  9840
acggcctctc gctcacccgg tgggacgtcc tcgggggctg agcgcgccgt cgccgtgccg  9900
gaggtcagcc gcccgtcgcg ggcgacttct tcgcggactc ggggatctcc gcgtcggagc  9960
ggatcgcctt ccacagctgg tcggcctgcg ggtgcgcggc caccacccgg ttcgggtcgg  10020
tcttgtcgta cgccacgggg agcatgacgg tctccatgga cgccgggtcg accccgttca  10080
tgctgcgcgc gaagtccgcc aggctggtca gcgaggccag ctcggagtcg gtggtcaggg  10140
ccgaggtcag ggtgtcggcg atcttgtacg tcttggtggg gctgccgaac aggtcctgct  10200
tcttcacctc gctcagcagg gcgatcatga actgctgctg gaggcctatg cggcccaggt  10260
cgctgccgtc gccgacgccg tgccgggtcc ggacgaacgc cagggagtcg gtgccgtcca  10320
gcttgtgcgt cccggcgctc aggtccaggc cgctcgtgct gtccttgatg ggctcgtcga  10380
cggtgaccgt gacgccgccg atcgcgtcga ccagcccctt gaagccggcg aagtcgatct  10440
ccatgtagtg gtccatgcgg acgccggaca tcttctccac ggtcttgacc acgcaggccg  10500
ggccggccgt cgagtacacg gagttgaaca tgacgcgctc ggcctgcgga agggcggagc  10560
cgtccgcctt ggtgcactcc gggcgggtga cgagggtgtc gcgcgggatg ctcacggcga  10620
cggcctgccg gcggccctcc gggatgtgca tgaccagcgc ggtgtccgac cgggcgcccg  10680
ccaccttgcc ggtgcccagg ccggcgttgt ctccggcacg cgagtccgag ccgaggacca  10740
gcacgttctg tccggaggtc ggcagcttct cggggcggtc ctcgccgagg gcctcgtcca  10800
ggtcgacccc gtcgatgttc ccgttcaggt cgctgtagag ccagtagccg gtgccccccg  10860
cggcgagcac gacggccagc agggacagca ggacgatgcg tccccagcgc cggcgcttcg  10920
gccggcggcg tccgccgccg gactcgggct gcgcacgccg ggactccgtg gtggcgctgt  10980
gcgtcatggt tcttgggttc ctctcctcac gggctccgcg cggcggagtg gggcccgggt  11040
ggggggagac cggtccacag atgcgttcac gtcagtggga gaactatagg cagcggtcca  11100
cggcacatcc tgcacgggtg gaattagcac ggctcagcga tgaatgccac atgaaccgac  11160
cttgaccact cttaaggctg gaataagatg tgtcgggcct gtgaccgtcg tggagggggg  11220
ctttcacgag gtcggaggtg ctggtggggc ggagcggccg gaagccgcga agcctcacat  11280
aaggggtggg cgtccggtgt ggacgatttg gtgtcccggc gggcgaaatg tcttggtagg  11340
agtacgagtt ggtggttcag ccgcgtctga gtattgtcgt gcccttccag gacgtcgagg  11400
tgtacctcgc cgagtgtctg gaatcgatcg cgcggcagtc gttccgcgac ttcgaggtca  11460
tcctggtcga cgacggctcc accgacgggt ccgtgcggat cgcggcggac ttctgcgccg  11520
ccgaccgccg tttccggctg gtccgccagc acgcccacgg accgggccac gcgcgcaaca  11580
ccggactgcg gaacacgcac cccgcggcgg agttcctcgc cttcgtggac ggtgacgacg  11640
tcatccccga gtacgcctac gaactcctgg tgcgcacgct cgaggagtcc gagtcggact  11700
tcgtctcggg caacgtgcag atgatgaact ccaccaagaa gtggcagtca ccgctgcaca  11760
agggccccat gcagaagaac cggcgcggga cgcacatcac gaagttcgac gcgctgatct  11820
acgaccgcac cgtctggaac aaactcttcc ggcgctcctt ctggaaccag aactccatca  11880
ggttccccga aggcgtgctg tacgaggact cgtgggtcaa catgtacgcc cacttccgcg  11940
ccgccaaggt cgacgtcatc acggacgtcg tctatttctg gcgccgccgg gacggcggag  12000
cggcgccctc catcacccag cgccactccg aactgtcgaa cctccgggac cgggtcgcgg  12060
ccgtgcagtc ggtgagccgc ttcctcggcg accggcgctc gcgtgagtac gcggacagca  12120
agcggaagta cgatctcgcc tgcctgaagt ccgacctcct gctccatctg aaggtgctcc  12180
cggacgcgga cgaggagtac cagcacgcct tcatgaagtg ggccaacgag ttcctcgacg  12240
agacggatct caccatcatc gacgagctgc ccgcggactc ccgcgtcaag tggctcctgg  12300
tgcgcgagga gcggctggcc gaactgctcg aggtcatcga gttcgagcgc cgcggcggtc  12360
ccatgcccgt gcagcggcgt ttccggcgct acctgaacta cccgtacctc ggggaccggg  12420
gggtgggcct cgacaagaag gcctaccggc tggacaagga gctctcgctg cacggctcgc  12480
tgtccggagc ccgctggagc accggctccg acctgctcac cctcaccgga acggcgtacg  12540
tccgcttcat caacgtgcac aagaagcaca tgtcggtgaa ggcgatcgcc ctgcggaaca  12600
agaagcaggg gcgcatgcag atcacgacgg cgaagaccgt ctacgcgccg caggcgaccg  12660
aggacagtaa gcagaatcgt tactgctatg actgggccgg cttcgaggcg cgcatcgaca  12720
ccacccgcct caagcgcaag ggccagtggg tcgagggcac ctgggacgtg gccgccggtg  12780
tcctcagccg gggactgttc cgctaccggg gcatcgaccg gggcggcgcg ggcagcgccg  12840
ccaacccgcc ctaccgctac gtcgacaaga acacccgcat cctcccggtc ttcctccagg  12900
gcaaactcaa gctgcgcgtc gagatcgtgc gctgccggat caccaagcac cgtgtcgtcg  12960
gcgaccagct ggagctgcgc ggcgtctacc tcggccccaa ggtcccggag tggggcaagc  13020
tccgcgtcac cagcatgagc ggcgcgggac gccacgacgc acgcgtccac ttcaccccgg  13080
gcggtgaggg ctggtgcacc ttctccgcca agctccccct gagccgtctg gtgcccaagt  13140
cccgcgtcca ggcgggaacc gacgcggacg tcccgcagtc ctggggcatg ggcagcaacg  13200
gctggaagac caccttccac gtcgagggcc gcaagtcggc catctatccc gtgatggcgg  13260
aggagacccc ggacgggcac tactccatgc cgtcctccct gcagaccccg gagcgcgacc  13320
gggagatcgt cgtgcaccgc aacggctccg gctatctcgt gctcttcgaa cgagcgaccc  13380
tgcccctggc gacccggtgc gactggcagg aggacggctc gctgtggatc cagggccgtt  13440
acctggccgc ggaccagctg accccggagc agtaccgctc cgcccacctc gtggtgcgct  13500
cgcgcgccca cggcgcggaa cgctccgtac cgctcacctg ggacgggcac gagttccgct  13560
gcgtcctggc ccccgccgcg atgcggaccc tggccgggga catcccgctg gcggccggac  13620
```

-continued

```
ggtgggactt cttcctgcgc cgccaggacc tgtcggccgt ggcccgcgag gaccggctcg  13680
aagacctcat ggtgaagatc gagcaggatc tcatcgaggc gttcccgcag gagtacgaga  13740
gaaacgaacg ccgctacgag acgcaggccg aggcctacga ccggctgtcg ctgctcgtcc  13800
actcggcgat gcccgaccac gcccgcggcc cctaccggca gaagctcctg aggaccaagg  13860
cctaccccga cgcccggcgc cggccggtgc gtgacgccgt gctgttcgac gccttcaagg  13920
gcacccagta ctcggacagc cccgcgcccc tgcacgagga actcgtgcgc cgccgcaccg  13980
gcctggaaca cctctgggtg gtgcgcgacg accaggtgca ggtgccgccc acggcgacgc  14040
ccgtccgcat gtggtcgccg gagtggtacg aggccctcgc caccagccgc tacgtcgtcg  14100
ccaacaacca cctcccggac tggttcaaga agcgggacgg acaggtcgtc gtgcagacct  14160
ggcacggcac gccgctgaag aagatcggcc acgacatcga gtccatccac ttcgccgacc  14220
agcgctatct ggaacgcgtc gagaaggagg tgcagaactg ggacatgctg gtgtcgccca  14280
acagcttctc caccccgatc ctcaagcgcg ccttcggctt ccccggcgag atggtggaga  14340
gcggctaccc gcgcaacgac atcctgcgcc ggccggacac cggggcccgg gagcaggaga  14400
tccgccgcag catcgggctg ccggagggca agcgggtggt gctgtacgcg ccgacctggc  14460
gcgacgacca gttctacgcg cccggcaagt acaagctgga cttccggatc gacctggccg  14520
ccgcgcgtgc gcagctcggc cccgaccacg tcctcatggt gcgccgccac cccaacgtcg  14580
tggacccggt gccgggcgcc ggcgacggat tcgtcttcga cgtgtccgac tacccggaca  14640
tggccgacct ctcgctgatc accgacgtga tgatcaccga ctactcctcc ctgatgttcg  14700
actacgtgaa caccgggcgg cccatcctgt tcttcaccta cgacctggac cactaccggg  14760
acaccctgcg cgggttctac ttcgacttcg agggcagcgc gccgggcccc ctcctctaca  14820
cgtccgagga actggtggcg gcgatccgtg acatcgacgc catccaggac ctctacgccg  14880
agcggtaccg ctggttccag cgggagttct gcgacctgga cgacggttac gccgcggccc  14940
ggctcgccga ccggatgctg gtcgcgggcg gcgacctcgc cccgggcag gcgcacgcgc  15000
cggccgtcgg cgcggtcgac acccggcaca ccggaaggcc gatgaccccc ctccagtggg  15060
ggaactcgga gtggttcgcc ggcccccgcc cgccggcggg tctcgtcgac gccgtgcccg  15120
cccagcccgc cccggcgtac gacgccgtac cgcagcacca ggcgggtccg ttcggccata  15180
ccccgcccgc cggcgaccgc agctacgaag gcgtgatcgc gtgacgccgc cgaccccgcc  15240
cggcgcgagg tccccggcgt gccgcgcggt gccggaaggc cccggccccc gatgaccgcc  15300
gtgccgttcg ccacgcgggc gccggccgcc gctgccggtc cgtcgtccgg cggccgcccg  15360
ggcgcgtcct cagccggtgc cggtgtccac ccggatcagc agcgcgcggt ggtcggagac  15420
cccggtgtcg ctcacccggc acccgagcac gggcagcccg gtgaagaggt agtccagctt  15480
gtggtgcgag acgtgcgtcg gccgggccgg ccggagggga ccgggcgtcc cgtcgcactc  15540
ccggtgcgtg ccgtaaggct ggtcgggcca gacccgggag agcgggttgc gctctcccgg  15600
cggatccacg ttgaggtcgc cgccgtagac ggtgcgccgc tcgggcaccg cgtccaccag  15660
ggccttcagc tgtccggcgc ggaactcgcg gtccggatgc gccagatcgc cgccgcgcgg  15720
ggtcagatgc gcggtgcaca ccgtgaggtc gtgcgccgcg acgaacgcgc agagtattcc  15780
gcgctgcacc ccgaccgcgg gctggggcgc gggcaccgcg cgcacggacg acagcggata  15840
cgccgacagc agggcgtagc ccgcggagcc ccggccgggc gccccgcagc gcaccgcggt  15900
gcggcgcccg tcacggccgc gccaggtgta ggccctgaac tccgcgtgcc acgacgcccc  15960
gagggaggcg cgcaccgcct cgacgtccgc cgcgcaggtc tcctgcagga acagcacccg  16020
ggccccggat tccgcggcga ggcgttccgt ccggccgcgc ttggcgtcct cgccgcccgt  16080
gccctcgcag ttccattccc tgaccccgca catgttccag gtcgccacgg tcagtgtccg  16140
gtccccggtg gcggagcggt ccgctccatt gccgctccgc tcgtgggtca ccacggcggc  16200
gagccccgcg agggcggcgg ccgccgtgac ggcggcgagc aggcgccgtc cgcgcgggcg  16260
gggcgaccgg gttcggttcc tgagcacccg gccatcatga ccgatccgcc gctgaccagc  16320
caaaaccacc cggcgccagg cgccttccgg caggtgtcct ccccctgccc gcgcacccgc  16380
ccgtcgtcca agtacctctg agagtggagt ccgtacatgt ccaaggcacc ctcgaacggg  16440
cggcagctgc tcaacggcat cgaagcctcg ggaacgttcc cggtggagta ccggttcacc  16500
cacgccaaga gcggcaaccg gcacctcgtg gtggtcttcg ccaacttctc ggcacccgag  16560
gactacggct ggtcgaacgg cgtcttcgac aacgtccgtg ccaacatcct gtggatccgt  16620
gaccggttcg acgggatgaa cgcctactac ctgtgccgga acatggactt cggtctggcg  16680
gactcggtgc agaccctgat cgcgaacgtc accggggcgc tcgggctgac gccggaccaa  16740
gtcacgctct ggggcggctc caagggcggc agcgccgcgc tgtacttcgg cctgcggtac  16800
ggctaccgga acatcgtcgc catcgtcccg cagttcctca tcggcgacgc cctggagaag  16860
cggcacccga aggtctccgc gtacatgctc ggcgaagggg cgcaggcgca caacgcgcgg  16920
atcctggacg cgctcctgcc cgacctggtg cgcgccaagg ccaacccggg cgccaacatc  16980
tacgtgctct cctccccgca ggacgagcat tacgccgtgc aggtcgagcc gttcctcggc  17040
atgttccacg gctacgagaa cttcaatttc ctgtacagcg agtcgccgac catcacgggg  17100
cacgccacgg cgacccggcg gaacgtcccg gcgctggtcg gcctgctcaa cctgctcgcc  17160
gacggctacg ccccccggct gggcttcacc cgccacgccg ccgaggactt cgaccacgac  17220
cggtcggaca tcaacgccta cctcgcctcg acctccaagg tccagggcgc cgacgcgttc  17280
gcgccgccgg tggtgaccac cccgggcttc aacagcgagg tcccgcgcac cggaccgtgg  17340
ttcaccggga cggcccacgg agcggtgcgg gtgagcatgt ggcgcaacgg caagttcgtg  17400
gcgtcgcccc aggtcgcggc cgacggcacc tggtcctggc agccgaccgg gccgtgggag  17460
gccgggaagc acatcgtcaa gatcttcgcg gtggacccgg cgggcttcca ctccgcccgg  17520
gtcgagatcc ccttcaccgt ggtcgaccgg gatcccgtcc ctgccccgcc ggtcgtctcc  17580
gcaccggtgt ccgggcagca gaccggagcg gcggtcgggt tccacggcag cgcgccggga  17640
gcgtcacagg tcggcttccg ggagaacggc gtgctcctcg gcgcggtggc cgtcgcgccc  17700
gacggcacct ggggctggga ccccggccgg ccctggcccg aggggcagca cctggtcgag  17760
atcgtcgcgg tcgacgcgta cggcatggag tccgcgcccg ccgccgccgg cttcaccgtg  17820
ctcggccacg cggtgcccgc cggacacttc acgccgcggt actgaccgac ggcccaggac  17880
gacgacacac cacgagtggg aagcagacat gccgaaagaa gcgccgacaa cacgcgagct  17940
gatcaccggg atcgacacct ccggcgcgta tcccgtcgag taccggttca cgcacgccaa  18000
gggggcaac cggcacctcg tcgtcgtgtt cgccaacttc gcggtcaagg acgactacgg  18060
ctggtccaac ggcgtcctca acccggtgcg ggccaacatc ctgtggatcc gtgaccggtt  18120
ccgcgacatg aacagctact acctgtgcga ggggatggac ttctccctgg agcagtccgt  18180
gatcgggctc atctccaagg tgatgaacgc cctggaactc accccggagc aggtcacgat  18240
gtggggcggc tcgaagggcg gcagcgccgc gctctacttc ggcatgcgct acggcttcgg  18300
caacatcgtc tccatcgtgc cgcagttcct cgtcggcacc tatgtgaagc gggtgcaccc  18360
```

-continued

```
caaggttgcc cggttcatgc tgggcgaggc ggtgccggag gagaacgtcc gcgcggtcga  18420
cgcgctcatc ccggacctgg cccgttcggg cgtcgcccgg cactccaaca tctatctgct  18480
ctcctcgccg caggacgagc agtaccagga gcaggtcgag cctttcctcg gactgttcca  18540
ggggtacgac aacttcaact tcgtgttcag cgagtccccc cacatcaccc gtcactcgga  18600
cgtcacccgg cgcaacgtcc ccttcctgat gggcctcgtg aacatgctcg ccgacgggat  18660
gtccccgcgg ctgggcctgg tgcgcaacgg gtacgaggag ccggaccgcg acaggtccgc  18720
catcgagggc ttcctggcgg ccacttcggc ggagcggccc agcgccatcc cgatgcccgt  18780
ggtgacgcat ccgcttccgc acatggaact gcccacggac ggcgtgtact tcacagggac  18840
ggcccccggc gcggtgcggg tgagcctgtg ggagcacggc aagttcctgg gttcgccgtc  18900
ggtggcgccg gacggcacct ggtcctggaa gcgggacaag ccgtggagca agggcgacca  18960
tctggtcaag gccgtcggct gggacgcgga gaagcgccgc accaagggca ccgtggtccc  19020
gttcaccacg gtcgccggcg cgaacgccgc cgcgcccggg gcaccggccg ccgcgcccct  19080
ggcgcccggg cagccgctgc cggcgccgac ggtccacacg ccgggggcgt acgagcagat  19140
caccggcacg gccgtgcgct tcagcggctt cgcccccggc gccgcccagg tgggattcag  19200
ggcggggggc accctccttg gcacgagccg ggtcgcggcc gacggaacgt gggcctggga  19260
ctccggctgg ccctggcagg cgggcatgca caccgtggag gtgttcgccg tggacgccgc  19320
gggatccgag tcgcccgtgg cgccggtgcc cttcgacgtc atgcacgcca cggcgggcgc  19380
ctcgccgttc gcctactgac cggtcgccac gcgcggaagg gctcctggag atcgccggcg  19440
atctccagga gcccttccgc ggtctacggg gactaggcgg gcacgctcgc cgtgcccggc  19500
tccaggaacc gcttcccgtt cacccgctcg gagacgccct cgcggtccag gtacggcgtg  19560
atgccgccca ggtggaaggg ccagccggcg ccggtgatca ggcacaggtc gatgtcctgg  19620
gcctcggcga cgacgccctc gtcgagcatg agcccgatct cctgggccac cgcgtccagg  19680
acgcgggcgc ggacctgctc ctcggtgagg acggtgtcgc cctgcttcag gagcgcggcg  19740
acctccgggt ccagctcggg cttgccgctg tcgtagaggt agaagccacg cttgccggcc  19800
tcgacgaccg ccctgaggtt cggggagacc gtgaagcgct ccgggaacgc cctgttgagg  19860
gtctcggaca cgtgcagacc gatcgcgggg ccgaccagct ccagcagcac cagcggggac  19920
atcggcaggc cgagcggctc gacggccttc tccgcgacct cgaccggggt gccctcgtcg  19980
atgacgttct ggatctcgcc catgaagcgg gtcaggatgc ggttcacgac gaacgccggg  20040
gcgtccttga ccaggaccgc ggtcttcttc agcttcttgg cgacaccgaa cgccgtggcc  20100
agcgccgcgt cgtcggtccg ctcgccgcgg acgatctcca ggagcggcag gatcgcgacc  20160
gggttgaaga agtggaagcc gacgacccgc tcggggtgct tcagcttcga cgccatctcg  20220
gagacggaga gcgaggaggt gttggtggcg aggatcgcgt gcgccggggc gaccgcctcg  20280
acctccgcga acacctgctg cttgacgccc atctcctcga agacggcctc gatcacgaag  20340
tcggcgtccg cgaagccctc ggccttgtcc agcacaccgg tgaccagggc cttgaggcgg  20400
ttggccttgt cctggttgat ccggcccttg ccgagcagct tgtcgatctc ggcgtggacg  20460
tagcccacac ccttgtcgat gcgcgcctgg tcgatgtcgg tcagcacgac cggcacctcg  20520
aggcggcgca ggaacagcag cgcgagctgg gaggccatca gaccggcgcc gaccacgccc  20580
accttggtga ccgggcgggc cagcgacttg tccggggcgc cggccggccg cttgccgcgc  20640
ttctgcacca ggttgaacgc gtagatgccg gagcgcagtt caccgcccat gatcaggtcg  20700
gcgagcgcct ggtcctcggc gtcgtagccc tgctggaggt cgccgttctt ggcggcggcg  20760
atgatgtcca gggcgcggta ggcggccggg gcggcgccgt gcaccttgga gtcggcgatg  20820
aagcggccct tggcgacggc ctggtcccag gcctcgccgc ggtcgatcac cgggcgctcg  20880
atccggatct cgtccttgag gacggccgcg gtccagatca gcgactgctc caggaagtcc  20940
gcgccctcga agatcgcgtc cgcgatgccg agttcgaaga cctgcgcgcc cttgagctgc  21000
ttgttctggt tgaggctgtt ctcgatgatg accgagacgg ccttctcggc gccgatcagg  21060
ttcggcagca gcgtgcagcc gccccagccg gggacgagac cgaggaagac ctcggggagc  21120
gagaacgccg ggagggcggc cgacaccgtg cggtaggtgc agtgcagacc gacctcgacg  21180
ccaccgccca tcgccgcgcc gttgtagtac gcgaaggtcg gcacggccag cgtcgacagc  21240
cgcttgaaga cgtcgtggcc gcccttgccg atggccagcg cgtcctcgtg ccgcttcagc  21300
agctcgacgc ccttgaggtc ggcgccgacg gcgaagatga acggcttgcc ggtgacgccg  21360
acgccgacga tctcgccgtc cgcggcctcc ttctcgaccc ggtcgatcgc ggcgtcgatg  21420
ttcgccagcg actgcgggcc gagcgtggtc ggcttggtgt ggtcgtggcc gttgtccagg  21480
gtgatgagcg cgaagcgccc ggcgcccagg gggaggtcga agtggcgcac gtgcgcgctg  21540
gtgacgacct cgccggggaa cagctcggcc gcacccttca gaagctctgc ggtggtgctc  21600
acttgtcccc ctcgaagtgc gggttctccc agatgaccgt cgcgcccatg ccgaagccga  21660
cgcacatggt ggtgaggccg taacggacct gcggctgctc ctcgaactgg cgggccagct  21720
gcgtcatcag acggacgccg gaggaggcca gcgggtggcc gaacgcgatg gcgccgccgt  21780
actggttgac gcgcgcgtcg tcgtcggcga tgccgtagtg ctccaggaag gccagcacct  21840
ggacggcgaa ggcctcgttg atctcgaaca gaccgatgtc ggagatggac agccccgcct  21900
gggcgagggc cttctccgtg gccgggatcg ggccgtagcc catgacctcg ggctccacgc  21960
cggcgaagga gtaggagacc aggcgcatct tgaccgggag gccgttctcg cgggcgaagt  22020
cctcgctcgc gatgaccgag gcggtggcgc cgtcgttcag accggccgcg ttgccggcgg  22080
tgacccggcc gtggacgcgg aagggggtct tcaggccggc caggttctcc agggtggtgc  22140
ccgggcgcat cggctcgtcg gcggtgacca ggccccagcc ggtctcaccg gcctcctcgt  22200
tggtgcggcg caccgagacc gggaccaggt cggcctggat cttgccgttg gcgtaggcct  22260
tggcggcctt ctcctgggag cgcacggcgt actcgtcggc gcgctgcttg gtgatcgagg  22320
ggtagcggtc gtgcaggttc tccgcggtca tgcccatgaa cagggcggac tcgtcgacca  22380
gcttctcgga gacgaagcgc gggttggggt cgacgccctc gcccatcggg tggcggccca  22440
tgtgctcgac gccgcccgcg atggcgacgt cgtacgcgcc gaaggcgacg gagccggcga  22500
ccgtggtgac ggcggtcagg gcgccggcgc acatgcggtc gatggagtag cccgggaccg  22560
aggtgggcag gcccgcgagg atgccggccg tgcggccgat ggtcaggccc tggtcgccga  22620
tctgcgtggt cgcggcgacg gcgacctcgt cgatcttctt cgggtcgaga ccggggttgc  22680
ggcgcagcag ctcccggatc gccttcacga ccaggtcgtc ggcgcgggtc tcgtggtaga  22740
tgcccttcgg gcccgccttg ccgaacgggg tacggacgcc gtcgacgaag acgacgtccc  22800
tgacggtacg aggcacgatg gctctcctcc cagggtgcgg gacgctgagc gcttgcttac  22860
gccatgctac ttatgagtaa cgtgactgcc cagtcccggc cccccgagcg gcgaacatca  22920
cacgtacggc ggcgcccgcc aaacgccgga ggggctggaa tcagccccct ccggcgtttg  22980
aggagcggga acccctcacg gtggagccgt ggagcctcgc ggggtcagga ccggggtcgg  23040
taccgggtgc gaccccggct gctcctcccc ggtgatgacg ccgaacagcg tgcgcgccac  23100
```

-continued

```
ctccgccccg aacccgtgca catcgtgact catcgcggac agcgtcggat gcgtcagccg  23160
gcacagctgc gagtcgtccc acgccagcag cgacacgtcg tccggcaccc gcagccccat  23220
ctccgccgcc accgacagcc ccgccaccgc catgatgtcg ttgtcgtaca cgatcgccgt  23280
gggccgttcc cccggcgcgg ccgccagcag cgaacgcgtc gcccgcgccc ccgcgtcccc  23340
cgagaagtcc gtggccgtct gccacgcccg cgcgggcggc tccagcgccc ggaccgcctc  23400
gtcgaacgcc gccgtgcgga tcgaggtgtg cccgagcgcc gccgcgccgc ccacccgggc  23460
gatccgccgg tgcccgagcg ccgccagata ccgcacggcc tccgtcacgg ccgtggcgtc  23520
gtccgtccac acggaggtga gcccgcccgt cagcgccggg tgcccgacgg ccaccgccgg  23580
cagcccgagc cgctccgcca ccgccggacg gggtcgccg gcccggaagt ccaccaggat  23640
cgagccgccg atctgccgcc cgcgccacca cgactccatc agcccgacct cctcctccgg  23700
gctgcgcacc agccgcagca gcagcgagca ggaccgctcc accaggacgc tctccacccc  23760
ggagatgaac tccatgtaga acggctccag gccgagcagc cgggcgggcc ggcagaccgc  23820
gagacccacc acgtccaccc gcgacccggc cagcgtgcgc gcggttcggc tcggcgccca  23880
ccccagctcc cgcgccgccc ggaagatgcg gtcccgggtc gcctccgaca gcccgggctt  23940
ccggttgaag gcgagggaca cggcgccctt ggacacgccg gcgcgcgcgg cgacgtccct  24000
gatggtgacg cgaggggtcg gcgttgccgt catcgagtgg gctccacgca gtacagggcg  24060
gaacgggcgg tgtccgggtc cggagtcttc cacccccgca ccccgatggt cacctgttcc  24120
ccggggagca gggtcaccag cccccggtcg gcccgcgccc cggggtccag ccggtcggcc  24180
tggagcagca ggtcccgtac gagggtgcgg gccgtgaccg tgatcccgtc cggcgcgagg  24240
gcgacctcga actccggcgg ggggtagggg atctcccggt ccggcgccgg gaagtgccac  24300
gcccgcaccc cgtccgcgtc ggcgaccagg aactccccgg ggccgtccgg cagcagttcg  24360
accgggacct cgaccacggc caccgtccgc cccccggcgt ccagcgccgg ggccgcctcc  24420
gcgatcgggg cgccgtcgac ggacatccgg cgcagccgca gcgttccccg ccagtcctcc  24480
gcggactggt tgaccgccgc caccaccaga ccgtcaccgt ccgcgcgcac ggtcagcagc  24540
cggtccgcgt acagccggcg cagctcgtgg tagagcggct tctcccgccc gtccccgtcg  24600
atcgcggccc acgacgtcac cggccagcag tcgttgagct gccagaccac cgtgcccgcg  24660
cacaccggcc agtgcgagcg ccagtgctcg acaccggccg ccaccgcacg cgcctggttg  24720
acctgcgtca gatagtgcca gcggtcgaag tcgccctccg gcacggcgaa gtggcgggcg  24780
aggccgcgct ccagcttgcc gttgccgtcc tccgccttct ggtggtgcag catgccgggg  24840
gagtccggcg cggggtcctc cccgggcagc gcccgccgca gcgtggcgtg cgcgggaggc  24900
gcctgccagc cgaactcggc cacgaagcgc gggacgtcgc gccggtagtc ggcgtagtcg  24960
gcgcggttcc acacctccca ggagtggtgg gtgccgtgcg ccggatcgtt ggggtggtgc  25020
cgccaggaac cggaccaggg actgcccgcc gtgtacggcc gcgtcgggtc cagctccgcg  25080
accacccgcg gcaggacgcc gaggtagtag ccctcgcccc aggagtcccc ggcgagcccc  25140
tgctcccagt cccagtcccg gaacccccac aggttctcgt tgttgccgtt ccacagcacc  25200
agggaggggt gcggcatcag ccgtacgacg ttctcccggg cctccgcctc cacctccccg  25260
cgcagcggct gctcctcggg gtaggcggcg cacgcgaacg ggaagtcctg ccagaccagc  25320
agccccaact cgtcgcaggc gtcgtagaag tcctcgtcct cgtagatccc gccgccccag  25380
acccggacca ggtccacccc cgcgccggcc gcctgctcca gccggtgccg gtagcgctcc  25440
cgggtgatcc gggacgggaa cacgtcgtcc gggatccagt tgacgccccg cgcgaacagc  25500
cgctcaccgt tgacgaccag ggtgaacccg gtgccgtgcg cgtcggccga ggtgtccagc  25560
tcaaccgtcc ggaacccggt cctgcgccgc caggcgtcca gcgcctcgtc accgtgggac  25620
aacgtcagct cgacgtcgta cagcggctgt tcgccgtatc cgcgcggcca ccacaggcgg  25680
acgtccggca cccggagccg cacggtcccg gccgtcccat cgacccgcgc ccgggcgcgc  25740
acgcccccgg cgctcgcctc cagggtgagc ggtgcctcga cccgggagcg ctccacgtcg  25800
accgccagct cgatctgccc caccccgtcc tcgacggtga ccagcgggcg cacccgggcg  25860
atccgcgccg tcgaccagcg ctccagccgc accggccgcc agatcccggc cgtcaccagc  25920
gtcggccccc agtcccagcc gaacgagcag gccatcttcc gcaggtactg gtacggctcg  25980
gcgtacgctc cggggcgctc gcccagcctg ccgcgcaccg cctccgcctc ggcgtacgcg  26040
gaggcgaacc gcaccgtgag ccggccgctc agtcccgtca cgtcgaagcg gtacgagcgg  26100
tgcatgttcc gcgtccggcc cagtggccgg ccgtcgagca ggatctcggc gacggtgtcg  26160
agaccgtcga agacgaggtc cgtctgctcg tgcgggcccg tcccggcggt cagctccgtc  26220
tcgtacgtcc actcccgccg gcccacccag gccacctcgg tctcgttgcg gccgaggaac  26280
ggatcgggga tcagcccggc cgccagcaga tcggtgtgca cacaccccgg caccgaggcg  26340
gggagggcgt cccccgtgcc gtccgggtgt cgcaggatcc atccctcggt gagcggtgtg  26400
acctgacgca tgcacactcc ctaaaccggt tgagccttct ctgaagagtg gtctggcatc  26460
gttggcgcga ttgcgacttt accggttcag ttcagggctg ccagagtgcc gaatcagcca  26520
tcccactcgt gctcgtccgt cccgtgaacg gagccgtgat gcatctgaac cgccgtacga  26580
cactcaccgg atcgctcgcc ctgctcgccc tcctggcctc cgcctgcacg ggcacggggg  26640
gttcctcgaa gggcgcggac gccaaggctc ccgacgaccc gtcaaaggtc aaggggtccc  26700
tcacggtcct cacccaccgg accgatctgg tgcaggacgg gacgatgaag aagtacgccg  26760
ccgagttcaa cgagacctat cccggggtga aggtggagtt cgacggcctc accgactacg  26820
agggcgaggt caagatccgt atgaacacgg agaactacgg cgacgtcctc atgatcccgg  26880
cggtcgtcga gaagaaggac tacccgaagt tcttcgcctc cctgggcacc aaggccgaac  26940
gcgccgccaa gtaccggttc accgactact ccaccgtcga cggcaaggtc tacgggcaga  27000
gccccgtcgg cgtcgtcccc gggttcatct acaacaagcg ggtgtggagc gaggccggcg  27060
tcaccgactg gcccaccacc cccgccgagt tcctggacga cctgaaggcg atccggtcga  27120
agaccgacgc ggtgccgtac tacaccaact tcaaggacat gtggccgctg acccagtgga  27180
ccaacgtcaa cggctccgtc ggctgcgacc cgcacgccac cacgaagctc gccgagggcg  27240
acccgtgggc cgagggggcc gacctgcgcg tgggcgacac cctgctccac gacatcgtgc  27300
gcggcggact cgccgagaag gacccgacca ccaccaactg ggagggctcc aagcccaagc  27360
tggccaaggg cgagatcgcc accatgtggc tgggctcctg ggccgtcgtg cagatgcggg  27420
acgcggcgaa gcaggccggc gccgaccccg ccgacatcgg cttcatgccc ttccccgcac  27480
agcgggacgg cacgttctgc gcggtgacct ccccggacta ccagcaggcg gtcaacgtca  27540
actccgacaa caaggaggcc gcccgcgcct ggatcgactg gttcaccgac aagtccggct  27600
acgccgaggc caacctcgcc ctatcccccc tgaaggacgc cccgctgccc gccgtcctcg  27660
agccctacga gaaggccggc gtgaagctcc tggacctcga ggacagcaag ggcgccgagg  27720
tgaagtccct cgacaaccgc tccgaggtcg gcatctacaa gcccgactac cgccaggaac  27780
tcgtcgacct cgcccgcggc gcccgcaagg gcggcctgga cgactacctc ggcggcctcg  27840
```

-continued

```
gcgagcgctg ggccgaggcg cgcagcgcgc tgggggcctg atgacggaca ccacccgcaa  27900
ggcggcgcgg ccggttcccc cggccgcgcc cgccgggccg ggccgcgcgg cgccggcccc  27960
gcgccgcacc cggctgtcgc gccgcctcac cccgtggctg ttcctggccg caccgctggc  28020
cctgctcctg accttcacct acgcgcccga tcgccaacat ggtcgcgtac agcttcaccg  28080
actgggacgg cgtgagcccg gagctgaact ggacgggcac cgggaactac accgaactcc  28140
tcacccgctc cgagctgttc gaggtcttct tcgtcagcgg ctactacctc gtcgcctccg  28200
cggtgcagat cgtgctcgcc ctctacttcg ccacggtcct cagcttcgac gtccgcttcc  28260
ggaacttctt caagggcgtg ctgttcttcc cgtacctcat caacggggtg gccatcggct  28320
tcgtcttcct ctacttcttc caggacggcg gcaccctcga ctccgtactg ggcctgctcg  28380
gcgtcgagac cgaccacgcc tggctgggca cgccgttctc cgcgaacacc tcgctggccg  28440
gcgtctccgt ctggcgctac ctcggactga acttcgtcct cttcctcggc gcgatccagt  28500
ccatcccggg cgagctgtac gaggcggccg agatcgacgg cgcgaaccgc tggcagcagt  28560
tccggcacat catcgcgccc ggcatcagac ccgtgctgag cctgagcgtg atcctctcgg  28620
tctccggctc gctgtcggtc ttcgagatcc cgtacatcat gaccggcggc gccaccggca  28680
cggagacctt cgtgatccag accgtgaagc tggcgttcca gttcaacaag acgggactcg  28740
cctcggccgc cgccgtcgtc ctgctgctga tcgtcctggc ggtcacctgg gtgcagcggc  28800
gcatcgtccc cgacgagaag gtggacctcg tatgacccgc cgtaccgcgg cacgcgccct  28860
ggtcctgacg tccctgatcc tggcgacgct ggtggtgctg ctgccgctcg ccgtggtctt  28920
cctgacctcg ctgaagtcct ccgaggagat ggcgaacggc agcggagcgc tgacgccgcc  28980
cgacgacccg ctgaacttcg gcaactacgt gacggcgttc cgggacggcc agatgctgtc  29040
cgcgttcggg aacacggccg tcatcctggt cgtggccgtc ggcggaacga tcctgatcgg  29100
ctcgatgacg gcgtacgcga tcgaccgctt ccggttccgc ttcaagaagc tggtcgtggc  29160
gctgttcctg ctggccgcgc tggtccccgg ggtgaccacc caggtggcga ccttccagat  29220
cgtcaacagc ttcggcatgt tcgacagcct gtgggcgccg atcgccctct acatgggcac  29280
ggacatcgtc tcgatctacg tcttcctgca gttcatccgc tccatccccg tctccctgga  29340
cgaggcggcg cgcctggacg gcgccaacgc gttcaccgtc taccgcaagg tgatcttccc  29400
gctgctcaag ccggcgatcg cgacggtggt gatcgtaaag gggatcaacg tctacaacga  29460
cttctacatc cccttcctct acatgccctc cgaggacctg gggtcatct cgacgtccct  29520
gttccgcttc aagggcccct tcggcgcgca ctgggagacg atctcggcgg gcgcggtcct  29580
ggtcatcctg cccaccttga tcgtcttcct gttcctccag cgcttcatct acaacgggtt  29640
catgcggggg gcgacgaagt agccagcgcg gccaccagca cgggagtgac ctggtcgacc  29700
tgccacgcgc gtgccccgtg cgccgtcagc gccgcggcga cggaccgctc gtcgggcccc  29760
ggcggctccc agcagaccct gcgcaccgtg tccggggtga tcaggttctc cggcggcatg  29820
ttcagccgct cggcgagttc ggcgaccccc gcgcgggccg ccgacagccg ggccgcggca  29880
acggggtcct tgtccgccca ggcgcgcggc ggcggagggc cggtcaccgg ctggccgggc  29940
tgcggcagct gggcctcgct cagcgccttc gcgcggtcga cggccgcctg ccactgctcc  30000
agctggcgcc gccccacccg ctgcccgaac ccgttgagcg cggccatggc gtgcaggttg  30060
gcgggcagcg cgagcgcggc ctccacgatc gccgcgtcgg aaagcacctt gccgggggag  30120
acgtcacggc gccgggcgat ccggtcgcgg gtctcccaca gctcccgcac caccgccatc  30180
tggcggcgcc ggcgcacctt gtgcatgccg gaggtgcggc gccaggggtc cttgcggggc  30240
tccggcggcg gggccgaggc gatcgcgtcg aactcctgcc gggcccagtc cagcttgccc  30300
tggcggtcca gctccttctc cagggcgtcc cgcagatcga ccagcagttc gacgtcgagg  30360
gcggcgtacc gcagccaggg ctcgggcagc ggacgggtgg accagtcgac ggcggagtgg  30420
cccttctcca ggacgaagcc gagcacgttc tcgaccatcg cgccgagccc gacgcggggg  30480
aacccggcaa ggcggccggc cagctcggtg tcgaagaggc gggagggcac catgcctatc  30540
tcgcgcagac agggcaggtc ctgggtggcg gcgtgcagca cccactcgac gccggacagc  30600
gcctcgccga gggcggacag gtcggggcag gccacggggt cgatcagcgc ggtacccgca  30660
ccctcgcggc gcagctggac gaggtaggcg cgctggccgt agcggtaccc ggaggcgcgc  30720
tcggcgtcca cggcgacggg tccgctgccg gccgcgaagg cggcgaccgc ctcggcgagg  30780
gcggcctcgt ccgctatcac gggcggaatg ccctcgcggg gttccagcaa gggggtcggc  30840
gcctccgtaa cagaagatcc gccgtcgtcc ggaggagcgc ctccggtggt gcgcagtgaa  30900
ctgtctgctg cggtgtcgtg ggcgtcggtc acctgtcaag ggtatccgtg ccgcgaaggc  30960
gcccgtcgac ggttgtgctc cgtgacgggc gccggtgggt cgtattccgg tcagaagagt  31020
gaaagaacgt gttcgcttgg ccgtgggcgg gcggatcggg gacgggcgga tcgggggcgg  31080
gacggaaggg tcagtggatg atgccggtgc gcagggccac ggccaccatg ccggcgcggt  31140
cgcccgtgcc gagcttgcgg gcgatccggg ccaggtggct cttgacggtc agtgcggaca  31200
ggcccatcga gacgccgatc gccttgttcg actggccttc cgccaccagc cgcagcacct  31260
ccacctcgcg gccggacagc tcgcggtagc cgcccgggtg gctcggggca cccggggggc  31320
ggcggtgcag gcgcgcggcg gcggcgccga tgggagcggc acccggccgg gtggggagcc  31380
cgaggttggt gcgggtgccg gtgacgacgt agcccttgac tccgcccgcg agggcgttgc  31440
gcacggcgcc gatgtcgtcc gccgcggaga gggcgaggcc gttgggccag cccgcggcgc  31500
gggtctcgga gaggagggtg aggccggaac catccggcag atggacttcg gcgacgcaga  31560
tgtcgcgggg gttgccgatg cggggacgag cctccgcgac ggacgaggcc tcgatgacgt  31620
cgcgtacgcc gagcgcccac aggtggcggg tgacggtcga acggacgcgg gggtcggcca  31680
cgaccaccat ggcggtcggc ttgttcgggc ggtaggcgac caggcttgcg ggctgctcga  31740
ggagaacgga caccaggcct cctggggtgc gggacgggcc ggctcgtggg ggtgaaggcg  31800
ggacgaaccg tgctttcaag gtcacagtcg tcttcggcag caaacctggt gtcctttaac  31860
gaatgatcac gaagtgatga gtaacaatcc gggcaattcg gacgcacgat cgatcattcg  31920
aagatcgaac ggtttcggtc tgcgtcgcaa cgcttccgaa agtggccgta tcgacaaaga  31980
gagatgcagg aggccggtcg tcgggacccc gcagcgggag gctcagcgcg actgcggccc  32040
cctccgctgc ggcagcgtca ccacggacgc gtcccccgga gcggccggcg gcagccccgc  32100
gacctgcgcc agcagatcgg accacgcgac cagatgggcg gccgtgtccg gaaccccgcc  32160
cagaccctca cgcggcgtcc acgaggcacg gatctcgatc tgggaggcgg cgggccgcgc  32220
ggacagcccg ccgaagtagt gcgaactcgc ccgcgtcacc gtgccgctcg gctcgccgta  32280
cgacaggccg cgcgccgcca gcgcgccggt cagccaggac cagcacacgt ccggcagcag  32340
cggatccgcc gccatctccg gctccagctc ggcgcgcacc agcgtcacca gacggaaggt  32400
cccccgccag gcgtcgtgtc cggccgggtc gcacagcagc accagccggc cgtcggccag  32460
atcctcctcg ccgtcgacga ccgccgcctc cagcgcgtgc gcgtacgggg cgagccgttt  32520
cggcgcgggc accgtctcca cctcgatctg cggccgcagc cgggcgctct gcagcgcctc  32580
```

```
gacagcggcc cggaagggcg gcggaggcgc acctccgtgc ccgggatccc ccccgccctc  32640
cttcggttcg tccattccgc cagcgccgtc cgacagtcgt ccctgagccg cagccatgcc  32700
gggaagatta agcggaacgg gcccccggcg cagggaggga cacccgcgcc gcccggcgct  32760
gtccggatcc tgcaccgcgg ccccgcccgc cggacgcccc tggggtccgg ggcggcggac  32820
gggtcgtgcg agactggccg gtgtgagtgc caacacgagc ccgaagggcc agacgcctac  32880
cgcgaccccc gaccccgtca agaacgacgc cgtccgggaa tcagccttcc tcaaggcgtg  32940
ccggcgcgag ccggtgccgc acacgccggt gtggttcatg cggcaggccg ggcgctcact  33000
gccggagtac cgcaaggtgc gcgagggcat cgggatgctc gactcctgca tgcggcccga  33060
gctggtcacc gagatcaccc tccagccggt gcgccgccac cacgtcgacg cggcgatcta  33120
cttcagcgac atcgtcgtcc cgctcaaggc catcggcatc gacctcgaca tcaagcccgg  33180
catcggcccg gtcgtcgagc agccggtgcg cacccgcgcc gacctcgccc ggctgcgcga  33240
cctgaccccg gaggacgtct cctacgtcac cgaggccatc ggcatgctga cccgtgagct  33300
cgggtccacc ccgctgatcg gtttcgcggg cgccccgttc acccttgcga gttacctcgt  33360
cgagggcggc ccgtcccgta cgtacgagaa cgccaaggcg atgatgtacg gcgaccccga  33420
gctctgggcc gacctgctcg accgcctcgc cgacatcacg gcggccttcc tcgacgtcca  33480
gatccgggcc ggcgcctcgg ccgtgcagct cttcgactcc tgggccggcg cgctcgcccc  33540
ctccgactac cggcgttcgg tgctgcccgc ctcggcgaag gtgttccgcg cggtggccgg  33600
ccacggcgtc ccgcgcatcc acttcggcgt cggcaccggc gagctgctgg ggctcatggg  33660
cgaggccggc gcggacatcg tcggcgtcga ctggcgcgtc ccgatggacg aggccgcccg  33720
ccgcgtcggc cccggcaagg cgctccaggg caacctggac ccgaccgtgc tgttcgccgg  33780
ccgggaggcc gtcgagacga aggcgcgcga ggtcctggac accgccgcgg gcctggaggg  33840
ccacatcttc aacctcggtc acggagtgat gccctccacc gacccggacg ccctcacccg  33900
tctcgtggag tacgtccaca cgcagacggc gcgctgaccc accgctcacg cgccggacgc  33960
gagtcggaat ccgggggcgg ggtactgggc acgggtgccc accacgttca cccccgggta  34020
cgggcaggtg gaggccccat gaggctcgag atgttcgacc ccgcccccgat cggcgtcgtg  34080
ttcacccagg ggccggagca ccggctcgcg tacaccaacg ccgtctaccg ggagaccttc  34140
ggcgaccgcc cgctggggcg gacgatccgc gaggccttcc ccgacctcgc gcagtccggc  34200
tacttcgaca tcttcgaccg ggtcctcacc acgggcgcgg ccgaggtggt caccgcggtg  34260
cccctcgacc tgatctaccc cggctccacg ggcgagggca ggcgctactt cacgttcagc  34320
atctcccgcg ccacgatgag cgacggccgg ccgggagtgc tcggcgtgat cgtggaggtg  34380
accgcgcagg tgaccgccgc ggaacggatc cgtgtgctgg ccgaggagcg ccgccgcgcg  34440
ctgcagcgct accgcagcct ggtgaacgcc ggaacgcaga tggtgtgggt ggcggacgcc  34500
aagggccgga tcaccgagcc gagccccggc tgggaacgcg tgaccgggca gacctgggag  34560
gagttccgcg gcgagggctg gatgaacgcc gtccaccccg acgaccgcgc cgcctcggtc  34620
gaggcgtggc ggcgggcgac gaccgaacag gtgccgcgct ggatccacac ctaccggctg  34680
cggctggccg ccggcgggta ccggcacttc gtcgtcgacg ccgcgcccgt gcgcgacggg  34740
aacacggtga tcgaatgggt gggcacctgc acggacatcg agcgggaatg gcaggagggc  34800
cgccgtacgg aactgctggc gcgggccgcc accgccacgt ccggcatcgc gcggctggac  34860
gagatgctcg ccgccctggc cgatgtgatc gtgcccgaca tcgccgacaa ctgcaccatc  34920
cacctcctgc cgcaggccct gcaccgtctg ccgggcaccc cgctgaccac cgaacgcgtc  34980
gccgcggtca cccgcccggg gctcccggac ctgcccccgc accacgagga gcacctgcgg  35040
cccggcagcc cgctggcccg cgccgccgac cgccgcagcc cgctccactt cgtcttcccg  35100
cccggcgagc cgccggccga cctcgctccg ctcgacggcg agccctggat ggccgaggac  35160
gtcaacagcg tcgtgctgct gcccgtcgtc gtcgacggca ccaccgccgc cctggtcgcc  35220
gtctccacca gcggcgcccg cccgcccctc ggccaggcgg agatcggcct gctgcagaca  35280
ctcctggaac gcgcccacac ccccctcagc aacgccctgg agtaccagcg cacccggcag  35340
gtggccctgg ccctgcagaa cagcctgctc accgacccgc cggacgcgcc cggcctggac  35400
atcgccgtcc gctaccggcc cagcaccgcc gccgccgagg tcggcgggga ctggtacgac  35460
gcgttcgtgc tgcgcgacgg cgccaccgtc ctcaccatcg gcgacgtctc cggccacgac  35520
ctgccggccg ccgtcaccat gagccagctg cgcaacatgc tgcgcgggct cacgctggac  35580
cgccaggaac cgaccggcac catcctgcgc cggctggaca tcgccgtgca gaccctctat  35640
acggagtgca ccgccacctg cgtgctggcc cgggtggaac gcccggactc cggcggcgtc  35700
cggctgcact actccgtcgc cggtcacccg ccgccgctgc tcgtcgaggc ggacggctcc  35760
gcgcgcttcc tgaccggggc gcggtccccg atgctcgggc tcgtccccgc gccggagtac  35820
tcgagcgcca tggaaccgct gccgcccggc tccaccctgc tgctgtacac cgacgggctg  35880
gtggagcgcc gcgacgagga tctcaccgtg ggcctggagc ggctgcggca ccacgcctcg  35940
gaggcggtca gccgcccgct gcaggacttc tgcgacacac tgctcaccgg ccagctcacc  36000
gtcgacaacg acgacgacgt ggcgatgctg gtcctgcgcc ggtaggagcg tgccgaggag  36060
cgccactctg gccgatttta cccttgcttt tccatcggga ttcgttctcc ggatttcccg  36120
atccggcgcc gacggcgaga ccgttgggat caccaatacc ccggaattcc cgcctccgcc  36180
accgttgggc agcgacggat cctgtgatat ttcgactacg cgcggtgatg aattggctcg  36240
gtgccggtcg cgcccggctg tagcagttct ggagcgcgtc tggacatcgt cacgagcgct  36300
tgtgattctt ggtcctgtac acgcaagccg gcgcaacgtc cacgttgccc atcagcggtt  36360
atcggcggtc caccggcgcg acggtgaccg cgggcgggta ctcatagggg gaactgcaat  36420
gaattactca aaagcagcga gaggaatgcc gacagccgga caaggtgccg ttcgggcggc  36480
gcgcgtcgtc cgtgaaagtc cggcggaatc agaaacggtc acagttcaga tagcgtcgtt  36540
attaccgggt gagtcgctgc gctcgaaagg gatcgagcag aaccacgtcg cggcactcgc  36600
ggaggtagac gcgccgcttc cgcccatact ggtggaccgg aagacgatgc gggtcgtcga  36660
cgggatgcac cggctcctcg cggctctgct caacggacgg cagacgatcg aggccgaact  36720
gttcgacgga accgcggatg agggattcct gcgcgccgtc cgggagaacg tggtgcacgg  36780
actcccgctg tcgcaggcgg accgccgggc cgccgctgcg cgcatcatcg tgtcccaccc  36840
gcatctgtcg gacagggcga tcgcccgggc gtccgggctc ggggcgaaga ccgtcgcggc  36900
cgtgcggcgc agttcaactg ccgtcgtgcc gcagttgaac acccgggtgg gccaggacgg  36960
cagggtccgg ccgctgaacg ggggcgaggg gcggcgcagg gccatggcgg tactggccga  37020
acaccccgac gcgtccctgc gcgaggtcgc ccgtctgtcc ggggtgtcgc ccgcgacggt  37080
cagcgacgta cgccggcggc tggccgccgg cgagtcgccc ctgccgtcga gacgggaacc  37140
ggccgaaccg cggacgggcg ccgactccca ccgcaaccag agcttcgtgg atcccgtccc  37200
ggtgctggag aagctgctgc gcgacccctc tctgcggcac aaggagggcg gccgccagct  37260
gctccagctg ctccgccaga acgcggtcgg cgtgcaggac ctgatggagc tgtccgacgc  37320
```

-continued

```
cgtgccgtcc cactgcaggt ccctggtgat ccatctcgcg cagcagtacc gggacgcctg  37380
gcagtccttc gcggagaagc tggacgagcc cgcctgcgcc tgtcccgggt gacgaacggg  37440
cggcacggac ccgttcaccg gacatgaccg gcgccgcgcc gcgttcacgg cgcgccgccg  37500
gcactcccac ggcacccgga ccaccgccgc gtatccggcg gacccgggcc cgggcgggcc  37560
ggattcagcg ggcgggggcc caggtgccac ccgattccag ccaccgggag agctccgccg  37620
ccgagtcctt gcgcacgacc agttcgacga ggccgcgggt ctggtcctga ccgtgctcga  37680
tgcggacgtc ctcgatgttg acgcccaagt cgccgatcga cgtgaacagt tcggccaggg  37740
cgccgggctt gtcggagatg gtcaccgaga cggtcgcgag ctccgtccgg cgcgtaccgg  37800
gtttgcgcac gatcctggcg cacccccggt tcccctcccg caacagctcc tcgagctcct  37860
cctgcgcgcg gcggcggacc agcgggtcgg cgtcggagac ggcgcgcagc gcgccgacgg  37920
cccggcccag gccggcggcg agggagtcga gaacgtccgc cacggccgtg gcgttggaac  37980
gcaggatgtc cccccagagc cgggcgtcac cggccgcgat ccgggtgacg tcggcgacgc  38040
cctgccccgc cagccggacg ctgtcctccg ccgcgtgctc cagccgcgcg gcgagcaggg  38100
aggagagccg atggggcgcg tgcgagacga gggccaccgc gtggtcgtgc acaccggcgt  38160
ccatgaccac cggcatgccg tcgcacaacg acaccatctc cagggcggtg ttcagcacgt  38220
cctgcccggt cagctccgac ggggtgagca cccaggggcg cccctcgaag aggtccgccc  38280
gggcggcgag cggcccggaa cgctcggtgc cggccagcgg atggcttcct atgtagctgg  38340
ccgggtcggc ccgcatcgcg cgcacgtcgt cgtgcgggac cttcttgacg ctggcgacat  38400
cgaggtaggc tcgggccagc ccgctctcct gtgcgcgcgc gagcacgcgt ccgacctgtg  38460
ccgggggcac ggccagcacc gccaggtcga cctgacggtc cggtctctcc agggatcccg  38520
cgcccatcgc ctccgccgtc ctggcggcgt tccggtcgac gtcctccagg tgcacgccga  38580
ccccgcggcg ggtcagcgcg agagcgacgg acgtgccgat ggccccggtg ccgatgactg  38640
tggtggtcct caacgcgcgc ccccaggtgc ggtgatccga aatcggctcg gacaagtgcc  38700
gtgcccggca cgggaaaagg gaattcccat ggcgccgtgc gccgccaatt taacgcttcg  38760
gcgcgcatgt tcaactgcgg cgtcgcagcg gtcgaacaca gtagcggtac accggaccat  38820
tgaggcatcg tgctcagttg gcgacaccgg gtcggataaa cgccggaatc cgaggagttg  38880
acgttgcagt cagcgctgag acacgacgac ctgcatccga tagaagaagt ggaaataagt  38940
tcgctctcca ccgacggctc cccgcggatc gacggggaga gtcccgagca cgtggaaatg  39000
ctggccgccg ccgacaccgc gcttccaccg atcatggtgc accgccgcac cgggcgggtc  39060
atcgacggca tgcaccggct gcgcgccgcg atgctgacgg gccgtacgac gatcgcggtg  39120
aggttcttcg acggcaccga ggaggacgcc ttcgtcctcg ccgtgaagtc gaacatcgcg  39180
cacggactgc cgctgtccgc cgccgaccgc cggcgggccg ccgggcgcat catggccacc  39240
catccccggt ggtcggaccg gatgatcgcc tcggtggtcg gcacctccgc caggacggtc  39300
gccgagatcc gccgcgacgc cggcgccgcc ggggcggggg agcccacccg catcggccgg  39360
gacggcaggg tacggcccgt cgacgtgagc gagggccgca gactggccca cgacatgatc  39420
gtccgcgacc cgggcctgtc gctgcgccag gtcgcccgcg ccgccgggat ctcgccggag  39480
accgtcaggg acgtcagaca ccggatgctc cgcggtgagg acccggtgcc cgcgccgcgg  39540
ccgcggaccc tggtggagcg cggcgcggac cgccgggcgg agccggccgg gaaggccgcc  39600
gcgccgtgcg ggacggagcc gccgcccgcc gtcgtgatga agcggctgag ggccgatccg  39660
gcgctgcgtc tcaacgagaa cggacgcgac ctgctgcggc ttctggatat ccacacggtc  39720
cggctggagg actggaaccg cattatcgaa agcgtgccgc cgcaccgtct ggagacggtg  39780
gcgcagctgg cacgctcctg cgccgacaaa tggtccgaga tcgcgtcacg catcgaaagc  39840
aacgcatcac atctggccgg gtgaacgagg aaacacacga atccttcgag gagccgtcgg  39900
agaaagcggg acggcccgtc ggaacaccct tgtggagggg caatggagat acggtcgatc  39960
gatcacgtcg aattgttcgt cgaggacgcc caggacacgg ccggcaggct gtgcgactcc  40020
ttcggcttcg tccgcgtggg ccgcggcgcc gggaccaccg gactgcgcgg ctgcgagtcc  40080
gtcctgctgc gccagaacga catcgccctg ctgctgacca cggccaccga cgccgaccac  40140
cgtgccgccg agtacgtgaa gcagcacggg gacggggtcg cggtgatcgg gtgggatccc  40200
cgggtaccga gctcgaattc gccctatagt gagtcgtatt acaattcact ggccgtcgtt  40260
ttacaacgtc gtgactggga aaaccctggc gttacccaac ttaatcgcct tgcagcacat  40320
ccccctttcg ccagctggcg taatagcgaa gaggcccgca ccgatcgccc ttcccaacag  40380
ttgcgcagct gaatggcgaa tggcgcctga tgcggtattt tctccttacg catctgtgcg  40440
gtatttcaca ccgcatatgg tgcactctca gtacaatctg ctctgatgcc gcatagttaa  40500
gccagccccg acacccgcca acacccgctg acgcgaaccc cttgcggccg c           40551
```